US008642292B2

(12) United States Patent
Sandig et al.

(10) Patent No.: US 8,642,292 B2
(45) Date of Patent: Feb. 4, 2014

(54) PROCESS FOR PRODUCING MOLECULES CONTAINING SPECIALIZED GLYCAN STRUCTURES

(75) Inventors: Volker Sandig, Berlin (DE); Hans Henning von Horsten, Berlin (DE); Christiane Ogorek, Berlin (DE)

(73) Assignee: Probiogen AG, Berlin (DE)

( * ) Notice: Subject to any disclaimer, the term of this patent is extended or adjusted under 35 U.S.C. 154(b) by 0 days.

(21) Appl. No.: 13/496,997

(22) PCT Filed: Sep. 21, 2010

(86) PCT No.: PCT/EP2010/005772
§ 371 (c)(1),
(2), (4) Date: Apr. 26, 2012

(87) PCT Pub. No.: WO2011/035884
PCT Pub. Date: Mar. 31, 2011

(65) Prior Publication Data
US 2012/0214975 A1    Aug. 23, 2012

Related U.S. Application Data

(60) Provisional application No. 61/244,624, filed on Sep. 22, 2009.

(51) Int. Cl.
C12P 21/06 (2006.01)
C12N 15/00 (2006.01)
C12N 1/20 (2006.01)
C07K 1/00 (2006.01)

(52) U.S. Cl.
USPC .............. 435/69.1; 435/320.1; 435/252.3; 530/350

(58) Field of Classification Search
USPC .............. 435/69.1, 320.1, 252.3; 530/350
See application file for complete search history.

(56) References Cited

FOREIGN PATENT DOCUMENTS

| EP | 1 331 266 A1 | 7/2003 |
| EP | 1 642 971 A1 | 4/2006 |
| WO | WO 2006/133148 A2 | 12/2006 |

OTHER PUBLICATIONS

Satoh Mitsuo et al: "Non-fucosylated therapeutic antibodies as next-generation therapeutic antibodies.", Expert Opinion on Biological Therapy, Ashley, London, GB, vol. 6, No. 11, Nov. 1, 2006, pp. 1161-1173, ISSN: 1471-2598, DOI: DOI:10.1517/14712598.6.11.1161.

Katsuhiro Mori et al: "Non-fucosylated therapeutic antibodies: the next generation of therapeutic antibodies", Cytotechnology, Kluwer Academic Publishers, DO, vol. 55, No. 2-3, Oct. 31, 2007, pp. 109-114, ISSN: 1573-0778, DOI: DOI: 10.1007/S10616-007-9103-2.

Imai-Nishiya Harue et al: "Double knockdown of alpha 1,6-fucosyltransferase (FUT8) and GDP-mannose 4,6-dehydratase (GMD) in antibody-producing cells: a new strategy for generating fully non-fucosylated therapeutic antibodies with enhanced ADC", BMC Biotechnology, vol. 7, Nov. 2007, ISSN: 1472-6750.

Kanda et al: Establishment of a GDP-mannose 4,6-dehydratase (GMD) knockout host cell line: A new strategy for generating completely non-fucosylated recombinant therapeutics, Journal of Biotechnology, Elsevier Science Publishers, Amsterdam, NL, vol. 130, No. 3, Jun. 19, 2007, pp. 300-310, ISSN: 0168-1656, DOI: DOI:10.1016/J.JBIOTEC.2007.04.025.

Omasa T, et al. "Decrease in antithrombin III fucosylation by expressing GDP-fucose transportersiRNA in Chinese hamster ovary cells", Journal of Bioscience and Bioengineering, Elsevier, Amsterdam, NL, vol. 106, No. 2, Aug. 1, 2008, pp. 168-173, ISSN: 1389-1723; DOI: DOI:10.1263/JBB.106.168.

Shields, R. L. et al: "Lack of Fucose on Human IgG1 N-Linked Oligosaccharide Improves Binding to Human FcγRIII and Antibody-Dependent Cellular Toxicity", Journal of Biological Chemistry< American Society for Biochemistry and Molecular Biology<INC>, US, vol. 277, No. 30, Jul. 26, 2002, pp. 26733-26740, ISSN: 0021-9258; DOI: DOI:10.1074/JBC.M202069200.

Ohyama C, et al., "Molecular Cloning and Expression of GDP-D-mannose-4,6-dehydratase, a Key Enzyme for Fucose Metabolism Defective in Lec13 Cells", Journal of Biological Chemistry< American Society for Biochemistry and Molecular Biology, Inc>, US, vol. 273, No. 23, Jun. 5, 1998, pp. 14582-14587, ISSN: 0021-9258, DOI: DOI:10.1074/JBC.273.23.14582.

Maki Minna et al>: "Functional Expression of *Pseudomonas aeruginosa* GDP-4-keto-6-deoxy-D-mannose reductase which synthesizes BDP-rhamnose", European Journal of Biochemistry, vol. 269, No. 2, Jan. 2002, pp. 593-601, ISSN: 0014-2956.

Rocchetta Heather L. et al: "Synthesis of the A-band polysaccharide sugar D-rhamnose requires Rmd and WbpW: Identification of Multiple AlgA Homologues, WbpW and ORF488, in *Pseudomonas aeruginosa*", Molecular Microbiology, vol. 29, No. 6, Sep. 1998, pp. 1419-1434, ISSN: 0950-382X.

Kneidinger Bernd, et al.: "Identification of Two GDP-6-deoxy-D-lyxo-4-hexulose reductases Synthesizing GDP-D-rhamnose in *Aneurinibacillus thermoaerophilus* L420-91T", Journal of Biological Chemistry, vol. 276, No. 8, Feb. 23, 2001, pp. 5577-5583, ISSN: 0021-9258.

Yamane-Ohnuki, N. and Satch, M. et al., Production of Therapeutic Antibodies with Controlled Fucosylation, mAbs, May-Jun. 2009, vol. 1, pp. 230-236, claims 1-15, 21-27.

*Primary Examiner* — Maryam Monshipouri
(74) *Attorney, Agent, or Firm* — Faegre Baker Daniels LLP

(57) ABSTRACT

The present invention relates to cells for producing a molecule lacking fucose, having a reduced amount of fucose, or having other atypical sugars on its glycomoieties. It also relates to methods for producing a molecule lacking fucose, having a reduced amount of fucose, or having other atypical sugars on its glycomoieties using said cells and to molecules obtainable by said methods. The present invention further relates to molecules having an artificial glycosylation pattern.

24 Claims, 9 Drawing Sheets

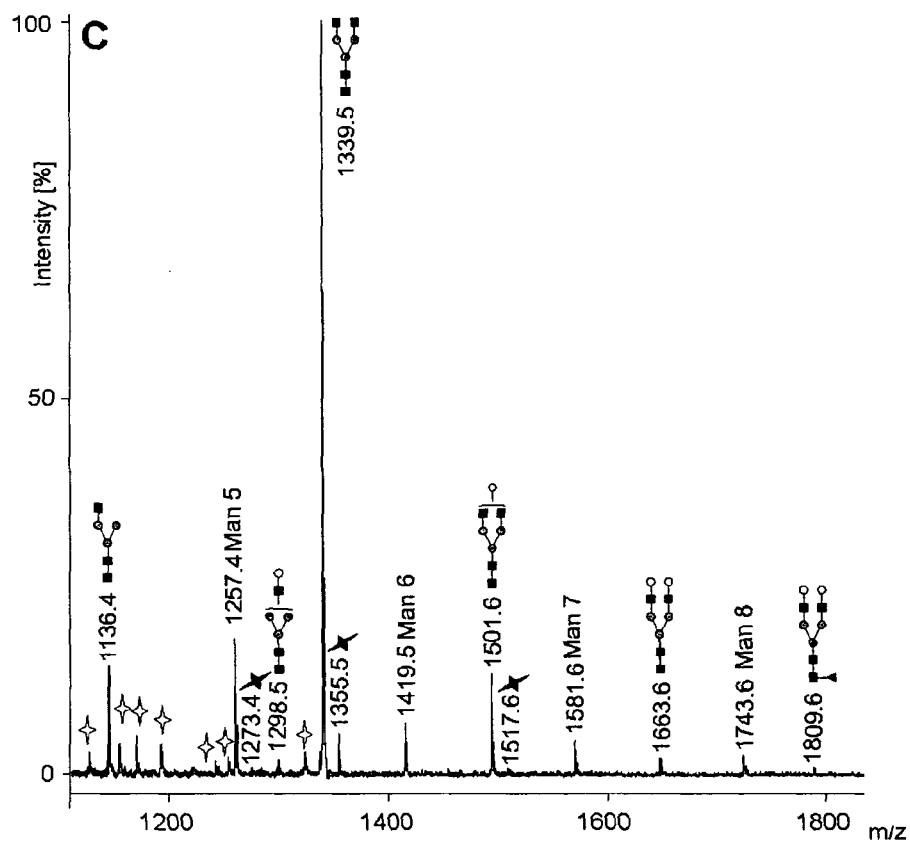
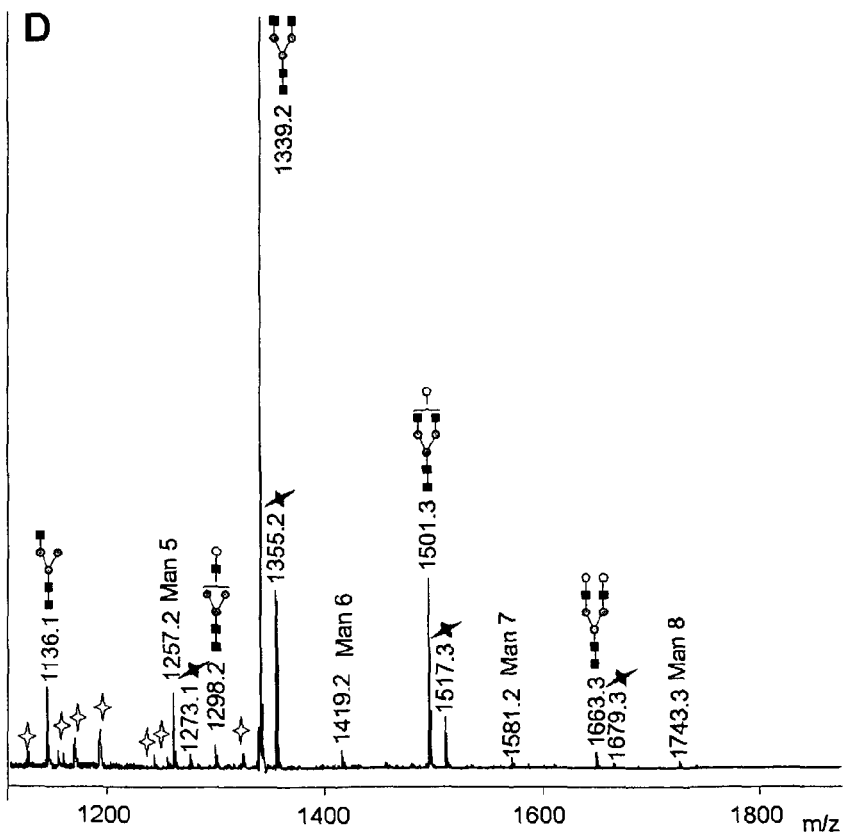

SEQUENCE LISTING

```
<160> NUMBER OF SEQ ID NOS: 7

<210> SEQ ID NO 1
<211> LENGTH: 304
<212> TYPE: PRT
<213> ORGANISM: Pseudomonas aeruginosa
<220> FEATURE:
<221> NAME/KEY: PEPTIDE
<222> LOCATION: (1)..(304)
<223> OTHER INFORMATION: GDP-6-deoxy-D-lyxo-4-hexulose reductase (RMD)

<400> SEQUENCE: 1

Met Thr Gln Arg Leu Phe Val Thr Gly Leu Ser Gly Phe Val Gly Lys
1               5                   10                  15

His Leu Gln Ala Tyr Leu Ala Ala Ala His Thr Pro Trp Ala Leu Leu
            20                  25                  30

Pro Val Pro His Arg Tyr Asp Leu Leu Glu Pro Asp Ser Leu Gly Asp
        35                  40                  45

Leu Trp Pro Glu Leu Pro Asp Ala Val Ile His Leu Ala Gly Gln Thr
    50                  55                  60

Tyr Val Pro Glu Ala Phe Arg Asp Pro Ala Arg Thr Leu Gln Ile Asn
65                  70                  75                  80

Leu Leu Gly Thr Leu Asn Leu Leu Gln Ala Leu Lys Ala Arg Gly Phe
                85                  90                  95

Ser Gly Thr Phe Leu Tyr Ile Ser Ser Gly Asp Val Tyr Gly Gln Val
            100                 105                 110

Ala Glu Ala Ala Leu Pro Ile His Glu Glu Leu Ile Pro His Pro Arg
        115                 120                 125

Asn Pro Tyr Ala Val Ser Lys Leu Ala Ala Glu Ser Leu Cys Leu Gln
    130                 135                 140

Trp Gly Ile Thr Glu Gly Trp Arg Val Leu Val Ala Arg Pro Phe Asn
145                 150                 155                 160

His Ile Gly Pro Gly Gln Lys Asp Ser Phe Val Ile Ala Ser Ala Ala
                165                 170                 175

Arg Gln Ile Ala Arg Met Lys Gln Gly Leu Gln Ala Asn Arg Leu Glu
            180                 185                 190

Val Gly Asp Ile Asp Val Ser Arg Asp Phe Leu Asp Val Gln Asp Val
        195                 200                 205

Leu Ser Ala Tyr Leu Arg Leu Leu Ser His Gly Glu Ala Gly Ala Val
    210                 215                 220

Tyr Asn Val Cys Ser Gly Gln Glu Gln Lys Ile Arg Glu Leu Ile Glu
225                 230                 235                 240

Leu Leu Ala Asp Ile Ala Gln Val Glu Leu Glu Ile Val Gln Asp Pro
                245                 250                 255

Ala Arg Met Arg Arg Ala Glu Gln Arg Arg Val Arg Gly Ser His Ala
            260                 265                 270

Arg Leu His Asp Thr Thr Gly Trp Lys Pro Glu Ile Thr Ile Lys Gln
        275                 280                 285
```

```
Ser Leu Arg Ala Ile Leu Ser Asp Trp Glu Ser Arg Val Arg Glu Glu
        290                 295                 300
```

<210> SEQ ID NO 2
<211> LENGTH: 294
<212> TYPE: PRT
<213> ORGANISM: Actinobacillus actinomycetemcomitans
<220> FEATURE:
<221> NAME/KEY: PEPTIDE
<222> LOCATION: (1)..(294)
<223> OTHER INFORMATION: GDP-6-deoxy-D-talose synthetase (GTS)

<400> SEQUENCE: 2

```
Met Lys Ile Leu Val Thr Gly Gly Ser Gly Phe Ile Gly Lys Asn Leu
  1               5                  10                  15

Ile Tyr Leu Leu Arg Glu Lys Arg Glu Phe Glu Val Phe Gly Ala Thr
             20                  25                  30

Val Glu Glu Thr Met Asp Leu Thr Asn Pro Cys Ser Val Gln Ser Val
         35                  40                  45

Leu Glu Lys Thr Lys Pro Asp Phe Ile Val His Leu Ala Ala Leu Thr
     50                  55                  60

Phe Val Pro Asn Asn Pro Ile Thr Phe Tyr Leu Val Asn Thr Ile
 65                  70                  75                  80

Gly Thr Glu Asn Leu Leu Arg Ser Ile Val Asp Leu Asn Val Ala Lys
                 85                  90                  95

Leu Gly Val Leu Cys Phe Ser Thr Ala Gly Ile Tyr Gly Ile Gln Glu
            100                 105                 110

Thr Lys Leu Leu Ser Glu Ser Leu Thr Pro Lys Pro Val Asn His Tyr
        115                 120                 125

Ser Met Ser Lys His Cys Met Glu His Ile Val Asn Lys Tyr Arg Cys
    130                 135                 140

Phe Arg Gly Ile Thr Val Val Arg Pro Phe Asn Val Leu Gly Leu Gly
145                 150                 155                 160

Gln Asn Ile Asn Phe Leu Val Pro Lys Met Val Ser Ala Phe Val Lys
                165                 170                 175

Lys Asp Lys Thr Ile Glu Leu Gly Asn Leu Asp Ser Val Arg Asp Phe
            180                 185                 190

Ile Ser Val Asn Asp Cys Cys Asp Ile Ile Tyr Arg Leu Ile Ser Lys
        195                 200                 205

Leu Ile Glu Asn Glu Thr Ile Asn Ile Cys Thr Gly Ile Gly Tyr Ser
    210                 215                 220

Val Tyr Gln Ile Phe Gln Leu Leu Cys Glu Ile Ser Met His Gln Met
225                 230                 235                 240

Glu Ile Lys Gln Asn Glu Leu Phe Val Arg His Asp Asp Ile Pro Gln
                245                 250                 255

Met Ile Gly Asp Pro Ser Lys Leu Leu Asn Val Leu Gly Asn Asp Tyr
            260                 265                 270

Arg Phe Thr Ser Val Arg Ala Ile Leu Glu Glu Met Tyr Lys Asn Arg
        275                 280                 285

Leu Leu Glu Leu Ser Ile
    290
```

<210> SEQ ID NO 3
<211> LENGTH: 367
<212> TYPE: PRT
<213> ORGANISM: Vibrio cholerae
<220> FEATURE:
<221> NAME/KEY: PEPTIDE
<222> LOCATION: (1)..(367)

<223> OTHER INFORMATION: GDP-perosamine synthetase (Per)

<400> SEQUENCE: 3

| Met | Ile | Pro | Val | Tyr | Glu | Pro | Ser | Leu | Asp | Gly | Asn | Glu | Arg | Lys | Tyr |
|---|---|---|---|---|---|---|---|---|---|---|---|---|---|---|---|
| 1 | | | | 5 | | | | | 10 | | | | | 15 | |

| Leu | Asn | Asp | Cys | Ile | Asp | Ser | Gly | Trp | Val | Ser | Ser | Arg | Gly | Lys | Tyr |
|---|---|---|---|---|---|---|---|---|---|---|---|---|---|---|---|
| | | | 20 | | | | | 25 | | | | | 30 | | |

| Ile | Asp | Arg | Phe | Glu | Thr | Glu | Phe | Ala | Glu | Phe | Leu | Lys | Val | Lys | His |
|---|---|---|---|---|---|---|---|---|---|---|---|---|---|---|---|
| | | 35 | | | | | 40 | | | | | 45 | | | |

| Ala | Thr | Thr | Val | Ser | Asn | Gly | Thr | Val | Ala | Leu | His | Leu | Ala | Met | Ser |
|---|---|---|---|---|---|---|---|---|---|---|---|---|---|---|---|
| | 50 | | | | | 55 | | | | | 60 | | | | |

| Ala | Leu | Gly | Ile | Thr | Gln | Gly | Asp | Glu | Val | Ile | Val | Pro | Thr | Phe | Thr |
|---|---|---|---|---|---|---|---|---|---|---|---|---|---|---|---|
| 65 | | | | | 70 | | | | | 75 | | | | | 80 |

| Tyr | Val | Ala | Ser | Val | Asn | Thr | Ile | Val | Gln | Cys | Gly | Ala | Leu | Pro | Val |
|---|---|---|---|---|---|---|---|---|---|---|---|---|---|---|---|
| | | | | 85 | | | | | 90 | | | | | 95 | |

| Phe | Ala | Glu | Ile | Glu | Gly | Glu | Ser | Leu | Gln | Val | Ser | Val | Glu | Asp | Val |
|---|---|---|---|---|---|---|---|---|---|---|---|---|---|---|---|
| | | | 100 | | | | | 105 | | | | | 110 | | |

| Lys | Arg | Lys | Ile | Asn | Lys | Lys | Thr | Lys | Ala | Val | Met | Ala | Val | His | Ile |
|---|---|---|---|---|---|---|---|---|---|---|---|---|---|---|---|
| | | 115 | | | | | 120 | | | | | 125 | | | |

| Tyr | Gly | Gln | Ala | Cys | Asp | Ile | Gln | Ser | Leu | Arg | Asp | Leu | Cys | Asp | Glu |
|---|---|---|---|---|---|---|---|---|---|---|---|---|---|---|---|
| | 130 | | | | | 135 | | | | | 140 | | | | |

| His | Gly | Leu | Tyr | Leu | Ile | Glu | Asp | Cys | Ala | Glu | Ala | Ile | Gly | Thr | Ala |
|---|---|---|---|---|---|---|---|---|---|---|---|---|---|---|---|
| 145 | | | | | 150 | | | | | 155 | | | | | 160 |

| Val | Asn | Gly | Lys | Lys | Val | Gly | Thr | Phe | Gly | Asp | Val | Ser | Thr | Phe | Ser |
|---|---|---|---|---|---|---|---|---|---|---|---|---|---|---|---|
| | | | | 165 | | | | | 170 | | | | | 175 | |

| Phe | Phe | Gly | Asn | Lys | Thr | Ile | Thr | Ser | Gly | Glu | Gly | Gly | Met | Val | Val |
|---|---|---|---|---|---|---|---|---|---|---|---|---|---|---|---|
| | | | 180 | | | | | 185 | | | | | 190 | | |

| Ser | Asn | Ser | Asp | Ile | Ile | Asp | Lys | Cys | Leu | Arg | Leu | Lys | Asn | Gln |
|---|---|---|---|---|---|---|---|---|---|---|---|---|---|---|
| | | 195 | | | | | 200 | | | | | 205 | | |

| Gly | Val | Val | Ala | Gly | Lys | Arg | Tyr | Trp | His | Asp | Leu | Val | Ala | Tyr | Asn |
|---|---|---|---|---|---|---|---|---|---|---|---|---|---|---|---|
| | 210 | | | | | 215 | | | | | 220 | | | | |

| Tyr | Arg | Met | Thr | Asn | Leu | Cys | Ala | Ala | Ile | Gly | Val | Ala | Gln | Leu | Glu |
|---|---|---|---|---|---|---|---|---|---|---|---|---|---|---|---|
| 225 | | | | | 230 | | | | | 235 | | | | | 240 |

| Arg | Val | Asp | Lys | Ile | Ile | Lys | Arg | Lys | Arg | Asp | Ile | Ala | Glu | Ile | Tyr |
|---|---|---|---|---|---|---|---|---|---|---|---|---|---|---|---|
| | | | | 245 | | | | | 250 | | | | | 255 | |

| Arg | Ser | Glu | Leu | Ala | Gly | Leu | Pro | Met | Gln | Val | His | Lys | Glu | Ser | Asn |
|---|---|---|---|---|---|---|---|---|---|---|---|---|---|---|---|
| | | | 260 | | | | | 265 | | | | | 270 | | |

| Gly | Thr | Phe | His | Ser | Tyr | Trp | Leu | Thr | Ser | Ile | Ile | Leu | Asp | Gln | Glu |
|---|---|---|---|---|---|---|---|---|---|---|---|---|---|---|---|
| | | 275 | | | | | 280 | | | | | 285 | | | |

| Phe | Glu | Val | His | Arg | Asp | Gly | Leu | Met | Thr | Phe | Leu | Glu | Asn | Asn | Asp |
|---|---|---|---|---|---|---|---|---|---|---|---|---|---|---|---|
| | 290 | | | | | 295 | | | | | 300 | | | | |

| Ile | Glu | Ser | Arg | Pro | Phe | Phe | Tyr | Pro | Ala | His | Thr | Leu | Pro | Met | Tyr |
|---|---|---|---|---|---|---|---|---|---|---|---|---|---|---|---|
| 305 | | | | | 310 | | | | | 315 | | | | | 320 |

| Glu | His | Leu | Ala | Glu | Lys | Thr | Ala | Phe | Pro | Leu | Ser | Asn | Ser | Tyr | Ser |
|---|---|---|---|---|---|---|---|---|---|---|---|---|---|---|---|
| | | | | 325 | | | | | 330 | | | | | 335 | |

| His | Arg | Gly | Ile | Asn | Leu | Pro | Ser | Trp | Pro | Gly | Leu | Cys | Asp | Asp | Gln |
|---|---|---|---|---|---|---|---|---|---|---|---|---|---|---|---|
| | | | 340 | | | | | 345 | | | | | 350 | | |

| Val | Lys | Glu | Ile | Cys | Asn | Cys | Ile | Lys | Asn | Tyr | Phe | Asn | Cys | Ile |
|---|---|---|---|---|---|---|---|---|---|---|---|---|---|---|
| | | 355 | | | | | 360 | | | | | 365 | | |

<210> SEQ ID NO 4
<211> LENGTH: 388
<212> TYPE: PRT
<213> ORGANISM: Escherichia coli
<220> FEATURE:
<221> NAME/KEY: PEPTIDE -continued

```
<222> LOCATION: (1)..(388)
<223> OTHER INFORMATION: GDP-4-keto-6-deoxymannose-3-dehydratase (ColD)

<400> SEQUENCE: 4

Met Ile Asn Tyr Pro Leu Ala Ser Ser Thr Trp Asp Asp Leu Glu Tyr
1               5                   10                  15

Lys Ala Ile Gln Ser Val Leu Asp Ser Lys Met Phe Thr Met Gly Glu
            20                  25                  30

Tyr Val Lys Gln Tyr Glu Thr Gln Phe Ala Lys Thr Phe Gly Ser Lys
        35                  40                  45

Tyr Ala Val Met Val Ser Ser Gly Ser Thr Ala Asn Leu Leu Met Ile
    50                  55                  60

Ala Ala Leu Phe Phe Thr Lys Lys Pro Arg Leu Lys Lys Gly Asp Glu
65                  70                  75                  80

Ile Ile Val Pro Ala Val Ser Trp Ser Thr Thr Tyr Tyr Pro Leu Gln
                85                  90                  95

Gln Tyr Gly Leu Arg Val Lys Phe Val Asp Ile Asp Ile Asn Thr Leu
            100                 105                 110

Asn Ile Asp Ile Glu Ser Leu Lys Glu Ala Val Thr Asp Ser Thr Lys
        115                 120                 125

Ala Ile Leu Thr Val Asn Leu Gly Asn Pro Asn Asn Phe Asp Glu
    130                 135                 140

Ile Asn Lys Ile Ile Gly Gly Arg Asp Ile Ile Leu Glu Asp Asn
145                 150                 155                 160

Cys Glu Ser Met Gly Ala Thr Phe Asn Asn Lys Cys Ala Gly Thr Phe
                165                 170                 175

Gly Leu Met Gly Thr Phe Ser Ser Phe Tyr Ser His His Ile Ala Thr
            180                 185                 190

Met Glu Gly Gly Cys Ile Val Thr Asp Asp Glu Gly Ile Tyr His Ile
        195                 200                 205

Leu Leu Cys Ile Arg Ala His Gly Trp Thr Arg Asn Leu Pro Lys Lys
    210                 215                 220

Asn Lys Val Thr Gly Val Lys Ser Asp Asp Gln Phe Glu Glu Ser Phe
225                 230                 235                 240

Lys Phe Val Leu Pro Gly Tyr Asn Val Arg Pro Leu Glu Met Ser Gly
                245                 250                 255

Ala Ile Gly Ile Glu Gln Leu Lys Lys Leu Pro Arg Phe Ile Ser Val
            260                 265                 270

Arg Arg Lys Asn Ala Glu Tyr Phe Leu Asp Lys Phe Lys Asp His Pro
        275                 280                 285

Tyr Leu Asp Val Gln Gln Glu Thr Gly Glu Ser Ser Trp Phe Gly Phe
    290                 295                 300

Ser Phe Ile Ile Lys Lys Asp Ser Gly Val Ile Arg Lys Gln Leu Val
305                 310                 315                 320

Glu Asn Leu Asn Ser Ala Gly Ile Glu Cys Arg Pro Ile Val Thr Gly
                325                 330                 335

Asn Phe Leu Lys Asn Thr Asp Val Leu Lys Tyr Phe Asp Tyr Thr Val
            340                 345                 350

His Asn Asn Val Asp Asn Ala Glu Tyr Leu Asp Lys Asn Gly Leu Phe
        355                 360                 365

Val Gly Asn His Gln Ile Glu Leu Phe Asp Glu Ile Asp Tyr Leu Arg
    370                 375                 380

Glu Val Leu Lys
385
```

```
<210> SEQ ID NO 5
<211> LENGTH: 321
<212> TYPE: PRT
<213> ORGANISM: Cricetulus griseus
<220> FEATURE:
<221> NAME/KEY: PEPTIDE
<222> LOCATION: (1)..(321)
<223> OTHER INFORMATION: GDP-Fucose synthetase (GST) (Fx protein)

<400> SEQUENCE: 5

Met Gly Glu Pro Gln Gly Ser Arg Arg Ile Leu Val Thr Gly Gly Ser
1               5                   10                  15

Gly Leu Val Gly Arg Ala Ile Gln Lys Val Val Ala Asp Gly Ala Gly
            20                  25                  30

Leu Pro Gly Glu Glu Trp Val Phe Val Ser Ser Lys Asp Ala Asp Leu
        35                  40                  45

Thr Asp Ala Ala Gln Thr Gln Ala Leu Phe Gln Lys Val Gln Pro Thr
    50                  55                  60

His Val Ile His Leu Ala Ala Met Val Gly Gly Leu Phe Arg Asn Ile
65                  70                  75                  80

Lys Tyr Asn Leu Asp Phe Trp Arg Lys Asn Val His Ile Asn Asp Asn
                85                  90                  95

Val Leu His Ser Ala Phe Glu Val Gly Thr Arg Lys Val Val Ser Cys
            100                 105                 110

Leu Ser Thr Cys Ile Phe Pro Asp Lys Thr Thr Tyr Pro Ile Asp Glu
        115                 120                 125

Thr Met Ile His Asn Gly Pro Pro His Ser Ser Asn Phe Gly Tyr Ser
130                 135                 140

Tyr Ala Lys Arg Met Ile Asp Val Gln Asn Arg Ala Tyr Phe Gln Gln
145                 150                 155                 160

His Gly Cys Thr Phe Thr Ala Val Ile Pro Thr Asn Val Phe Gly Pro
                165                 170                 175

His Asp Asn Phe Asn Ile Glu Asp Gly His Val Leu Pro Gly Leu Ile
            180                 185                 190

His Lys Val His Leu Ala Lys Ser Asn Gly Ser Ala Leu Thr Val Trp
        195                 200                 205

Gly Thr Gly Lys Pro Arg Arg Gln Phe Ile Tyr Ser Leu Asp Leu Ala
210                 215                 220

Arg Leu Phe Ile Trp Val Leu Arg Glu Tyr Asn Glu Val Glu Pro Ile
225                 230                 235                 240

Ile Leu Ser Val Gly Glu Glu Asp Glu Val Ser Ile Lys Glu Ala Ala
                245                 250                 255

Glu Ala Val Val Glu Ala Met Asp Phe Cys Gly Glu Val Thr Phe Asp
            260                 265                 270

Ser Thr Lys Ser Asp Gly Gln Tyr Lys Lys Thr Ala Ser Asn Gly Lys
        275                 280                 285

Leu Arg Ala Tyr Leu Pro Asp Phe Arg Phe Thr Pro Phe Lys Gln Ala
290                 295                 300

Val Lys Glu Thr Cys Ala Trp Phe Thr Asp Asn Tyr Glu Gln Ala Arg
305                 310                 315                 320

Lys

<210> SEQ ID NO 6
<211> LENGTH: 314
<212> TYPE: PRT
<213> ORGANISM: Cricetulus griseus
<220> FEATURE:
```

<221> NAME/KEY: PEPTIDE
<222> LOCATION: (1)..(314)
<223> OTHER INFORMATION: GDP-Fucose synthetase Cys109Ser-
      (GFS-Cys109Ser) mutant

<400> SEQUENCE: 6

Met Arg Ile Leu Val Thr Gly Gly Ser Gly Leu Val Gly Arg Ala Ile
1               5                   10                  15

Gln Lys Val Val Ala Asp Gly Ala Gly Leu Pro Gly Glu Glu Trp Val
            20                  25                  30

Phe Val Ser Ser Lys Asp Ala Asp Leu Thr Asp Ala Ala Gln Thr Gln
        35                  40                  45

Ala Leu Phe Gln Lys Val Gln Pro Thr His Val Ile His Leu Ala Ala
    50                  55                  60

Met Val Gly Gly Leu Phe Arg Asn Ile Lys Tyr Asn Leu Asp Phe Trp
65                  70                  75                  80

Arg Lys Asn Val His Ile Asn Asp Asn Val Leu His Ser Ala Phe Glu
                85                  90                  95

Val Gly Thr Arg Lys Val Val Ser Cys Leu Ser Thr Ser Ile Phe Pro
            100                 105                 110

Asp Lys Thr Thr Tyr Pro Ile Asp Glu Thr Met Ile His Asn Gly Pro
        115                 120                 125

Pro His Ser Ser Asn Phe Gly Tyr Ser Tyr Ala Lys Arg Met Ile Asp
    130                 135                 140

Val Gln Asn Arg Ala Tyr Phe Gln Gln His Gly Cys Thr Phe Thr Ala
145                 150                 155                 160

Val Ile Pro Thr Asn Val Phe Gly Pro His Asp Asn Phe Asn Ile Glu
                165                 170                 175

Asp Gly His Val Leu Pro Gly Leu Ile His Lys Val His Leu Ala Lys
            180                 185                 190

Ser Asn Gly Ser Ala Leu Thr Val Trp Gly Thr Gly Lys Pro Arg Arg
        195                 200                 205

Gln Phe Ile Tyr Ser Leu Asp Leu Ala Arg Leu Phe Ile Trp Val Leu
    210                 215                 220

Arg Glu Tyr Asn Glu Val Glu Pro Ile Ile Leu Ser Val Gly Glu Glu
225                 230                 235                 240

Asp Glu Val Ser Ile Lys Glu Ala Ala Glu Ala Val Val Glu Ala Met
                245                 250                 255

Asp Phe Cys Gly Glu Val Thr Phe Asp Ser Thr Lys Ser Asp Gly Gln
            260                 265                 270

Tyr Lys Lys Thr Ala Ser Asn Gly Lys Leu Arg Ala Tyr Leu Pro Asp
        275                 280                 285

Phe Arg Phe Thr Pro Phe Lys Gln Ala Val Lys Glu Thr Cys Ala Trp
    290                 295                 300

Phe Thr Asp Asn Tyr Glu Gln Ala Arg Lys
305                 310

<210> SEQ ID NO 7
<211> LENGTH: 307
<212> TYPE: PRT
<213> ORGANISM: Escherichia coli
<220> FEATURE:
<221> NAME/KEY: PEPTIDE
<222> LOCATION: (1)..(307)
<223> OTHER INFORMATION: GDP-L-colitose synthase (ColC)

<400> SEQUENCE: 7

Met Lys Ile Leu Leu Thr Gly Ser Thr Gly Met Val Gly Arg Asn Ile

-continued

```
1               5                   10                  15
Val Asp Asn Asn Asn Ser Asn Lys Tyr Glu Leu Leu Cys Pro Thr Ser
            20                  25                  30

Ser Glu Leu Asn Leu Leu Asp Asn Lys Ala Val His Asp Tyr Ile Thr
            35                  40                  45

Cys His Ser Pro Asp Leu Ile Ile His Ala Ala Gly Leu Val Gly Gly
        50              55                  60

Ile Gln Ala Asn Ile Lys Arg Pro Val Asp Phe Leu Val Ser Asn Leu
65                  70                  75                  80

Lys Met Gly Val Asn Ile Val Asn Glu Ala Lys Asn Cys Gly Val Lys
                85                  90                  95

Asn Phe Ile Asn Leu Gly Ser Ser Cys Met Tyr Pro Lys Gly Ile Asp
                100                 105                 110

Thr Ala Ile Ser Glu Asp Ala Leu Leu Thr Gly Lys Leu Glu His Thr
            115                 120                 125

Asn Glu Gly Tyr Ala Leu Ala Lys Ile Thr Val Ala Lys Leu Cys Glu
        130                 135                 140

Tyr Ile Thr Lys Glu Ser Glu Gly Tyr His Tyr Lys Thr Ile Ile Pro
145                 150                 155                 160

Cys Asn Leu Tyr Gly Lys Tyr Asp Lys Phe Asp Glu His Ser Ser His
                165                 170                 175

Met Ile Pro Ala Val Ile Asn Arg Ile His Asn Ala Lys Val Asn Asn
            180                 185                 190

Ile Lys Leu Ile Glu Ile Trp Gly Asp Gly Glu Ser Arg Arg Glu Phe
        195                 200                 205

Met Tyr Ala Glu Asp Phe Ala Asn Phe Ile Tyr Gln Ala Ile Pro Asn
    210                 215                 220

Ile Gln Arg Leu Pro Cys Met Leu Asn Val Gly Leu Gly His Asp Phe
225                 230                 235                 240

Ser Ile Asn Asp Tyr Tyr Lys Val Ile Ala Glu Glu Ile Gly Tyr Lys
            245                 250                 255

Gly Ser Phe Thr His Asp Leu Thr Lys Pro Val Gly Met Arg Arg Lys
            260                 265                 270

Leu Val Asp Ile Thr Leu Leu Ser Glu Phe Gly Trp Lys Tyr Gln Phe
        275                 280                 285

Glu Leu Arg Asp Gly Ile Lys Glu Thr Tyr Lys Tyr Tyr Leu Glu Asn
        290                 295                 300

Val Tyr Lys
305
```

PROCESS FOR PRODUCING MOLECULES CONTAINING SPECIALIZED GLYCAN STRUCTURES

CROSS REFERENCE TO RELATED APPLICATIONS

This application is a 371 national stage application of International Application No. PCT/EP2010/005772, with an International Filing Date of Sep. 21, 2010, which claims priority to U.S. Application No. 61/244,624, filed on Sep. 22, 2009, both of which are incorporated herein by reference in their entirety.

The present invention relates to cells for producing a molecule lacking fucose, having a reduced amount of fucose, or having other atypical sugars on its glycomoieties. It also relates to methods for producing a molecule lacking fucose, having a reduced amount of fucose, or having other atypical sugars on its glycomoieties using said cells and to molecules obtainable by said methods. The present invention further relates to molecules having an artificial glycosylation pattern.

BACKGROUND OF THE INVENTION

Therapeutic glycosylated molecules intended for use in humans should have complex glycosylation patterns similar to those found in humans. Therefore, animal cells are generally used to produce therapeutic glycosylated molecules, such as proteins, or lipids, where it is desirable that the glycosylated molecules have a complex, human-like glycosylation pattern. The structure and complexity of glycans severely affects in vivo function of the biomolecule via modulation of half life, receptor binding, induction or suppression of immune reactions.

Sugar chains of glycolipids are complex and can contain a significant amount of Fucose (PNAS 1985; 82: 3045-3049.). Sugar chains of glycoproteins are roughly divided into two types, namely sugar chains which bind to asparagine (N-glycoside-linked sugar chain) and sugar chains which bind to other amino acid such as serine, threonine (O-glycoside-linked sugar chain), based on the binding form to the protein moiety.

N-glycoside-linked sugar chains have various structures (Biochemical Experimentation Method 23-Method for Studying Glycoprotein Sugar Chain (Gakujutsu Shuppan Center), edited by Reiko Takahashi (1989)), but it is known that they have a basic common core structure. The sugar chain terminus which binds to asparagine is called a reducing end, and the opposite side is called a non-reducing end. N-glycoside-linked sugar chain includes a high mannose type in which mannose alone binds to the non-reducing end of the core structure; a complex type in which the non-reducing end side of the trimannose core typically has at least one galactose-N-acetylglucosamine (hereinafter referred to as Gal-GlcNAc) attached to each of the two (1,3 and 1,6) mannose arms The non-reducing end side of Gal-GlcNAc may contain galactose and sialic acid, bisecting N-acetylglucosamine or the like. In a hybrid type the non-reducing end side of the core structure has branches of both of the high mannose type and complex type. In glycans from vertebrate cells fucose may be attached to the antennary GlcNAc via an alpha 1,3 linkage (terminal fucose) or to the asparagine-linked GlcNAc via an alpha 1,6 linkage (core fucose). Insect cells produce glycans which may contain 1,3 linked core fucose.

The oligosaccharide moiety of N-glycosylated proteins is initially biosynthesized from lipid-linked oligosaccharides to form a $Glc_3Man_9GlcNAc_2$-pyrophosphoryl-dolichol which is then transferred to asparagine occurring in the tripeptide sequence Asn-X-Ser or Thr, where X could be any amino acid except Pro, of a protein in the endoplasmic reticulum (ER). Afterwards, the protein is transported to the Golgi-apparatus, where the oligosaccharide portion is further processed in the following sequence: First, all three glucose (Glc) residues are removed by glucosidases I and II to yield $Man_9GlcNAc_2$-protein. The $Man_9GlcNAc_2$ structure may be further processed by the removal of a number of mannose (Man) residues. Initially, four α-1,2-linked mannoses are removed to give a $Man_5GlcNAc_2$-protein which is then lengthened by the addition of a N-acetylglucosamine (GlcNAc) residue. This new structure, the $GlcNAcMan_5GlcNAc_2$-protein, is the substrate for mannosidase II which removes the α-1,3- and α-1,6-linked mannoses. Thereafter, the other sugars, GlcNAc, galactose, fucose and sialic acid, are added sequentially to give the complex types of structures often found on N-glycosylated proteins.

An IgG molecule, for example, contains a N-linked oligosaccharide covalently attached at the conserved Asn297 of each of the CH2 domains in the Fc region. The oligosaccharides found in the Fc region of serum IgGs are mostly biantennary glycans of the complex type. Variations of IgG glycosylation patterns include the attachment of terminal sialic acid (NeuAc), a third GlcNac arm (bisecting GlcNAc), a terminal galactosylation (G), and α-1,6-linked core fucosylation (F) to the core structure: 2× N-Acetylglucosamin (GlcNAc) and 3× mannose (Man) ($GlcNAc_2Man_3$). The exact pattern of glycosylation depends on the structural properties of IgG subcomponents, in particular, CH2 and CH3 domains (Lund et al. (2000) Eur. J. Biochem., 267: 7246-7257).

Animal and human cells have fucosyltransferases that add a fucose residue to the GlcNAc residue at the reducing end of the N-glycans on a protein or to other nascent glycostructures on glycolipids. Fucosylation of protein- or lipid-bound glycomoieties requires a nucleotide sugar, GDP-L-fucose, as a donor and also the presence of particular fucosyl transferases, which transfer the fucosyl residue from the donor to the acceptor molecule (Becker and Lowe, 1999). In eukaryotic cells GDP-L-fucose can be synthesized via two different pathways, either by the more prominent fucose de novo pathway or by the minor salvage pathway (Becker and Lowe, 1999). The salvage Pathway or "scavenger" pathway is a minor source of GDP-L-fucose (circa 10%) which can easily be blocked by omission of free fucose and fucosylated glycoproteins from the culture medium. The salvage pathway starts from extracellular Fucose which can be transported into the cytosolic compartment via fucose-specific plasma membrane transporters. Alternatively, fucose cleaved from endocytosed glycoproteins can enter the cytosol. Cytosolic L-fucose is phosphorylated by fucokinase to fucose-1-phosphate and then converted by GDP-Fucose Pyrophosphorylase to GDP-L-fucose (FIG. 1, right hand panel). Cell culture experiments suggest that the salvage pathway makes a relatively minor contribution to the cytosolic GDP-L-fucose pools (Becker and Lowe, 1999).

The more prominent fucose de novo pathway starts from GDP-D-mannose and consists of a GDP-mannose dehydratase (GMD) and GDP-keto-deoxy-mannose-epimerase/GDP-keto-deoxy-galactose-reductase (GMER, also known as Fx in humans), both located in the cytoplasm, which in concert converts GDP-mannose to GDP-L-fucose (FIG. 1, left hand panel). Later, GDP-L-fucose is transported into the Golgi via a GDP-fucose transporter located in the membrane of the Golgi apparatus. Once GDP-L-fucose has entered the Golgi luminal compartment, fucosyltransferases can covalently link GDP-L-fucose to nascent glycomoieties within the Golgi. In particular, Fucosyltransferase (Fut8) transfers the fucose residue by means of an 1,6-linkage to the 6 position of the GlcNAc residue at the reducing end of the N-glycan. The lack of fucose on glycoproteins has been shown to have specific advantages. For example, in monoclonal antibodies, immunoglobulins, and related molecules, it has been shown that absense of the core fucose sugar from the N-glycan attached to Asn297 of the Fc portion (CH2 domain) of immunoglobulins increases or alters its binding to Fc receptors. Different types of constant regions bind different Fc receptors. Examples include the binding of IgG1 Fc domains to cognate Fc receptors CD16 (FcγRIII), CD32 (FcγRII-B1 and -B2), or CD64 (FcγRI), the binding of IgA Fc domains to the cognate Fc receptor CD89 (FcαRI), and the binding of IgE domains to cognate Fc receptors FcεFR1 or CD23. Binding to the FcγRIII which is present on the surface of an NK Cells is strongly increased. (Shields et al. JBC 277 (30): 26733. (2002)).

A dominating mode of action of therapeutic antibodies is Antibody Dependent cytotoxicity (hereinafter referred to as "ADCC activity"). The antibody binding to a target cell (a tumor cell or a cell infected with a pathogen) with its Fab portion is recognised in its Fc portion by the Fc receptor of an effector cell, typically an NK cell. Once bound the effector cell releases cytokines such as IFN-γ, and cytotoxic granules containing perforin and granzymes that enter the target cell inducing cell death. The binding affinity to FcγRIII is critical for antibodies acting through ATCC. Carriers of a low affinity allele of the receptor respond poorly to therapeutic antibodies such as Rituximab (Cartron et al. Blood 99: 754-758).

Consequently, higher affinity to FcγRIII mediated by the absense of core fucose on the Fc glycan can increase the potency or reduce the effective dose of biotherapeutic product with major implications for clinical benefit and cost.

In order to modify the sugar chain structure of the produced glycoprotein, various methods have been attempted, such as 1) application of an inhibitor against an enzyme relating to the modification of a sugar chain, 2) homozygous knock out of a gene involved in sugar synthesis or transfer 3) selection of a mutant, 3) introduction of a gene encoding an enzyme relating to the modification of a sugar chain, and the like. Specific examples are described below.

Examples of inhibitors against enzymes relating to the modification of a sugar chains include castanospermin and N-methyl-1-deoxynojirimycin which are inhibitors of glycosidase I, bromocondulitol which is an inhibitor of glycosidase II, 1-deoxynojirimycin and 1,4-dioxy-1,4-imino-D-mannitol which are inhibitors of mannosidase I, swainsonine which is an inhibitor of mannosidase II and the like. Examples of an inhibitor specific for a glycosyltransferase include deoxy derivatives of substrates against N-acetylglucosamine transferase V (GnTV) and the like Mutants of enzymes relating to the modification of sugar chains have been mainly selected and obtained from a lectin-resistant cell line. For example, CHO cell mutants have been obtained from a lectin-resistant cell line using a lectin such as WGA (wheat-germ agglutinin derived from *T. vulgaris*), ConA (cocanavalin A derived from *C. ensiformis*), RIC (a toxin derived from *R. communis*), L-PHA (leucoagglutinin derived from *P. vulgaris*), LCA (lentil agglutinin derived from *L. culinaris*), PSA (pea lectin derived from *P. sativum*) or the like.

Furthermore, several methods for producing recombinant antibodies lacking fucose have been reported. One of the most important enzymes that enable core fucosylation of N-glycomoieties is α-1,6-fucosyltransferase 8 (Fut8). Said enzyme catalyzes the binding of fucose to the 6-position of N-acetylglucosamine in the reducing end through an α-bond in a N-glycoside-linked sugar chain pentacore of a complex type N-glycan (WO 00/61739). Antibodies with reduced fucose content have also been achieved using a cell in which the expression of fucose transporter genes is artificially suppressed (US 20090061485). The introduction of RNA capable of suppressing the function of α-1,6-fucosyltransferase has also been described to lead to the production of antibody molecules lacking fucose (EP 1 792 987 A1).

Many of the proposed cells or methods for producing molecules having a modified glycosylation pattern, which can be used for therapeutic indications, have significant drawbacks. For example, the treatment of antibodies with enzymes that remove glycosylations, e.g. fucosidases to remove fucose residues, involves additional manufacturing steps with are expensive, time-consuming and which have potentially significant economic and drug consistency risks. Further, the molecular engineering of cell lines to knock-out key enzymes involved in the synthesis of glycoproteins is tedious, expensive and not always crowned with success. In addition, said cell lines have the disadvantage that they do not allow the "tunable" production of molecules with varying ADCC or CDC potency to optimize efficacy and safety for a therapeutic use. The treatment of cell lines with RNAi or antisense molecules to knock-down the level of key enzymes involved in the synthesis of glycoproteins can have unpredictable off-target effects, is costly and appears to be impractical for implementation at manufacturing-scale.

Thus, there is a need for novel advantageous cells and methods for the production of molecules with a modified glycosylation pattern having improved properties for therapeutic uses.

The present invention provides cells for the production of molecules having a modified glycosylation pattern, i.e. molecules which lack fucose, have a reduced amount of fucose or have other atypical sugars on their glycan structures. It also provides methods for the production of molecules having a modified glycosylation pattern, i.e. molecules which lack fucose, have a reduced amount of fucose or have other artificial sugars on their glycan structures, using said cells. Said molecules have improved properties for therapeutic uses, e.g. increased ADCC or CDC activity, enhanced ability to inhibit signalling events, increased ability to induce apoptosis, and/or increased ability for immune therapy. In addition, the cells and methods provided by the present invention allow the tunable, reliable, inexpensive and straight forward production of molecules having a modified glycosylation pattern, i.e. molecules lacking fucose, having a reduced amount of fucose or having other artificial sugars on their glycan structures. Furthermore, the present invention provides methods which are suitable for manufacturing scale-up.

In many cases, considerable time has been invested and huge efforts have been made to generate and develop effective producer cell lines that express the transgene of interest at desirable levels. In cases where the transgene of interest is a therapeutic antibody that could benefit from enhanced ADCC effector function, it would be desirable to further manipulate the producer cell line in such a way that the high producer cell is incapable of attaching core-fucose to the N-glycomoieties or is capable of attaching artificial sugars to the N-glycomoieties.

The present invention provides an expression unit which can easily be applied to already existing genetically engineered cells in a way that renders them incapable to attach fucose to nascent glycostructures of glycoproteins or that render them capable to attach other artificial sugars than fucose to nascent glycostructures of glycoproteins, e.g. in order to produce antibodies having an improved ADCC activity.

SUMMARY OF THE INVENTION

In a first aspect, the present invention relates to a vertebrate cell for producing a molecule, which naturally comprises fucose on its glycomoieties, lacking fucose or having a reduced amount of fucose on its glycomoieties comprising at least one enzyme which uses GDP-6-deoxy-D-lyxo-4-hexulose as a substrate, wherein the enzyme does not catalyze the reaction which converts GDP-6-deoxy-D-lyxo-4-hexulose into GDP-L-fucose.

In a second aspect, the present invention relates to a method for producing a molecule, which naturally comprises fucose on its glycomoieties, lacking fucose or having a reduced amount of fucose on its glycomoieties comprising the steps of:
  i) providing a vertebrate cell according to the first aspect,
  ii) isolating the molecule which is capable of being a substrate for a fucosyltransferase, preferably a protein or lipid, from the cell in i).

In a third aspect, the present invention relates to a molecule lacking fucose or having a reduced amount of fucose on its glycomoieties obtainable by the method of the second aspect.

In a fourth aspect, the present invention relates to a molecule which comprises glycomoieties containing D-rhamnose, D-perosamine, deoxy-D-talose, 6-deoxy-D-altrose, 4-keto-3,6-dideoxy-D-mannose, and/or L-colitose obtainable by the method of the second aspect.

In a fifth aspect, the present invention relates to a composition comprising glycoproteins which comprise
  i) between 70 and 95% of G0-GlcNac, G0, G1, and/or G2 complex type N-glycans, and
  ii) between 5 and 30% high mannose type N-glycans,
wherein the complex type N-glycans are free of fucose or substantially free of fucose.

In a sixth aspect, the present invention relates to a protein or lipid which comprises glycomoieties containing D-rhamnose, D-perosamine, deoxy-D-talose, 6-deoxy-D-altrose, 4-keto-3,6-dideoxy-D-mannose, and/or L-colitose.

In a seventh aspect, the present invention relates to an expression unit comprising:
  i) one or more vertebrate expression control sequences, and
  ii) a polynucleotide comprising a nucleic acid sequence encoding an enzyme which uses GDP-6-deoxy-D-lyxo-4-hexulose as a substrate,
  wherein the enzyme does not catalyze the reaction which converts GDP-6-deoxy-D-lyxo-4-hexulose into GDP-L-fucose.

In an eighth aspect, the present invention relates to an eukaryotic cell for producing a protein, which normally comprises fucose on its glycomoieties, lacking fucose or having a reduced amount of fucose on its glycomoieties comprising:
  i) a first polynucleotide comprising a nucleic acid sequence encoding an enzyme which uses GDP-6-deoxy-D-lyxo-4-hexulose as a substrate, and
  ii) a second polynucleotide comprising a nucleic acid sequence encoding a protein,
  wherein the enzyme does not catalyze the reaction which converts GDP-6-deoxy-D-lyxo-4-hexulose into GDP-L-fucose.

In a ninth aspect, the present invention relates to a method for producing a protein, which normally comprises fucose on its glycomoieties, lacking fucose or having a reduced amount of fucose on its glycomoieties comprising:
  i) providing an eukaryotic cell according to the eight aspect,
  ii) expressing the enzyme encoded by the first polynucleotide and the protein encoded by the second polynucleotide in said cell, and
  iii) isolating the protein from said cell.

In a tenth aspect, the present invention relates to a protein lacking fucose or having a reduced amount of fucose on its glycomoieties obtainable by the method of the ninth aspect.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

The term "comprise" or variations such as "comprises" or "comprising" according to the present invention means the inclusion of a stated integer or group of integers but not the exclusion of any other integer or group of integers. The term "consisting essentially of" according to the present invention means the inclusion of a stated integer or group of integers, while excluding modifications or other integers which would materially affect or alter the stated integer. The term "consisting of" or variations such as "consists of" according to the present invention means the inclusion of a stated integer or group of integers and the exclusion of any other integer or group of integers.

In the context of the present invention, the term "oligopeptide" refers to a short peptide-linked chain of amino acids, e.g. one that is typically less than about 50 amino acids long and more typically less than about 30 amino acids long.

The terms "polypeptide" and "protein" are used interchangeably in the context of the present invention and refer to a long peptide-linked chain of amino acids, e.g. one that is typically 50 amino acids long or longer than 50 amino acids.

The term "polypeptide fragment" as used in the context of the present invention refers to a polypeptide that has a deletion, e.g. an amino-terminal deletion, and/or a carboxy-terminal deletion, and/or an internally deletion compared to a full-length polypeptide.

In the context of the present invention, the term "fusion protein" refers to a polypeptide comprising a polypeptide or polypeptide fragment coupled to heterologous amino acid sequences. Fusion proteins are useful because they can be constructed to contain two or more desired functional elements from two or more different proteins.

The terms "antibody", "immunoglobulin", "Ig" and "Ig molecule" are used interchangeably in the context of the present invention. The CH2 domain of each heavy chain contains a single site for N-linked glycosylation at an asparagine residue linking an N-glycan to the antibody molecule, usually at residue Asn-297 (Kabat et al., Sequence of proteins of immunological interest, Fifth Ed., U.S. Department of Health and Human Services, NIH Publication No. 91-3242). Included within the scope of the term are classes of Igs, namely, IgG, IgA, IgE, IgM, and IgD. Also included within the scope of the terms are the subtypes of IgGs, namely, IgG1, IgG2, IgG3 and IgG4. The terms are used in their broadest sense and include monoclonal antibodies (including full length monoclonal antibodies), polyclonal antibodies, single chain antibodies, and multispecific antibodies (e.g. bispecific antibodies).

The term "antibody fragment" as used in the context of the present invention refers to a fragment of an antibody that contains at least the portion of the CH2 domain of the heavy chain immunoglobulin constant region which comprises an N-linked glycosylation site of the CH2 domain and is capable of specific binding to an antigen, i.e. chains of at least one $V_L$ and/or $V_H$-chain or binding part thereof.

The terms "Fc domain" and "Fc region" refer to a C-terminal portion of an antibody heavy chain that interacts with cell surface receptors called Fc receptors and some proteins of the complement system. This property allows antibodies to activate the immune system.

In the context of the present invention, the term "glycoprotein" refers to proteins that contain oligosaccharide chains (glycans) covalently attached to their polypeptide sidechains. The carbohydrate is attached to the protein in a co-translational or posttranslational modification. This process is known as glycosylation such as N-glycosylation or O-glycosylation.

"N-glycosylation" means the addition of sugar chains which to the amide nitrogen on the side chain of asparagine. "O-glycosylation" means the addition of sugar chains on the hydroxyl oxygen on the side chain of hydroxylysine, hydroxyproline, serine, or threonine.

The term "glycolipid" as used in the context of the present invention refers to carbohydrate-attached lipids. They occur where a carbohydrate chain is associated with phospholipids on the exoplasmic surface of the cell membrane. The carbohydrates are found on the outer surface of all eukaryotic cell membranes. The carbohydrate structure of the glycolipid is controlled by the glycosyltransferases that add the lipids and glycosylhydrolases that modify the glycan after addition. Glycolipids also occur on the surface of enveloped viruses including those used as attenuated life vaccines.

The terms "glycan" or "glycomoiety" are used interchangeably in the context of the present invention to refer to a polysaccharide or oligosaccharide. The term "oligosaccharide" means a saccharide polymer containing a small number (typically three to ten) of component sugars, also known as simple sugars or monosaccharides. The term "polysaccharide" means a polymeric carbohydrate structure, formed of repeating units (either mono- or disaccharides, typically >10) joined together by glycosidic bonds. Glycans can be found attached to proteins as in glycoproteins or attached to lipids as in glycolipids. The terms encompass N-glycans, such as high mannose type N-glycans, complex type N-glycans or hybrid type N-glycans, O-glycans or In the context of the present invention, the following monosaccharides are abbreviated as follows: Glucose=Glc, Galactose=Gal, Mannose=Man, Fucose=Fuc or F, N-acetylgalactosamine=GalNAc, or N-acetylglucosamine=GlcNAc.

An "N-glycan" means an N-linked polysaccharide or oligosaccharide. An N-linked oligosaccharide is for example one that is or was attached by an N-acetylglucosamine residue linked to the amide nitrogen of an asparagine residue in a protein. The predominant sugars found on N-glycoproteins are glucose, galactose, mannose, fucose, N-acetylgalactosamine (GalNAc), N-acetylglucosamine (GlcNAc) and sialic acid (e.g., N-acetyl-neuraminic acid (NANA)). The processing of the sugar groups occurs co-translationally in the lumen of the ER and continues in the Golgi apparatus for N-linked glycoproteins. N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). N-glycans differ with respect to the number of branches (antennae) comprising peripheral sugars (e.g., GlcNAc, galactose, fucose and sialic acid) that are added to the $Man_3GlcNAc_2$ core structure which is also referred to as the "trimannose core", the "pentasaccharide core" or the "paucimannose core". N-glycans are classified according to their branched constituents (e.g., high mannose, complex or hybrid).

A "high mannose type N-glycan" means an N-linked polysaccharide or oligosaccharide which has five mannose residues ($Man_5$), or more mannose residues (e.g. $Man_6$, $Man_7$, or $Man_8$).

A "complex type N-glycan" means a N-linked polysaccharide or oligosaccharide which typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex type N-glycans in the context of the present invention may contain zero (G0), one (G1), or two (G2) galactoses as well as one fucose attached to the first GlcNAc on the reducing end (denoted as G0F, G1F, G2F, respectively).

A "hybrid type N-glycan" means a N-linked polysaccharide or oligosaccharide which has at least one GlcNAc on the terminal of the 1,3 mannose arm of the trimannose core and zero or more mannoses on the 1,6 mannose arm of the trimannose core.

The abbreviations used in the context of the present invention to describe the glycostructures are defined as follows:
core=$Man_3GlcNAc_2$
G0=$GlcNAc_2Man_3GlcNAc_2$
G0-GlcNAc=G0-structure missing one GlcNAc (i.e. $GlcNAcMan_3GlcNAc_2$)
G1=G0-structure containing one additional Galactose residue (i.e. Gal $GlcNAc_2Man_3GlcNAc_2$)
G2=G0-structure containing two additional Galactose residues (i.e. $Gal_2$ $GlcNAc_2Man_3GlcNAc_2$)
G0F=G0-Structure containing an additional fucose-residue which is connected to the first GlcNAc-residue of the pentasaccharide core (i.e. $GlcNAc_2Man_3GlcNAc_2$ Fuc)
G0F-GlcNAc=G0-GlcNAc-structure containing an additional fucose-residue which is connected to the first GlcNAc-residue of the pentasaccharide core (i.e. $GlcNAcMan_3GlcNAc_2Fuc$)
G1F=G1-structure containing an additional fucose-residue which is connected to the first GlcNAc-residue of the pentasaccharide core (i.e. $GalGlcNAc_2Man_3GlcNAc_2$ Fuc)
G2F=G2-structure containing an additional fucose-residue which is connected to the first GlcNAc-residue of the pentasaccharide core (i.e. $Gal_2GlcNAc_2Man_3GlcNAc_2Fuc$)
Man4=core-structure containing one additional Mannose residue (i.e. $ManMan_3GlcNAc_2$)
Man5=core-structure containing two additional Mannose residues (i.e. $Man_2Man_3GlcNAc_2$)
Man6=core-structure containing three additional Mannose residues (i.e. $Man_3Man_3GlcNAc_2$)
Man7=core-structure containing four additional Mannose residues (i.e. $Man_4Man_3GlcNAc_2$)
Man8=(core-structure containing five additional Mannose residues (i.e. $Man_5Man_3GlcNAc_2$)

An "O-glycan" means an O-linked polysaccharide or oligosaccharide. O-Linked glycans are usually attached to the peptide chain through serine or threonine residues. O-Linked glycosylation is a true post-translational event which occurs in the Golgi apparatus and which does not require a consensus sequence and no oligosaccharide precursor is required for protein transfer. The most common type of O-linked glycans contain an initial GalNAc residue (or Tn epitope), these are commonly referred to as mucin-type glycans. Other O-linked glycans include glucosamine, xylose, galactose, fucose, or manose as the initial sugar bound to the Ser/Thr residues. O-Linked glycoproteins are usually large proteins (>200 kDa) that are commonly bianttennary with comparatively less branching than N-glycans.

The term "a molecule which naturally comprises fucose on its glycomoieties" as used in the context of the present invention refers to any compound which upon production in a eukaryotic cell, preferably vertebrate cell, capable of adding fucose to glycomoieties, i.e. with an unaltered ability to add fucose to glycomoieties, comprises glycomoieties comprising at least one fucose residue. Such molecules comprise at least one or more sequence motifs recognized by a glycan transferring enzyme, e.g. comprising an Asp, Ser or Thr residue, preferably a tripeptide sequence Asn-X-Ser/Thr, wherein X is any amino acid except Pro. Preferred examples of eukaryotic cells (e.g. vertebrate cells) that produce molecules comprising glycomoieties with fucose are CHO, AGE1.HN, AGE1.CR, AGE1.CR.PIX, or AGE1.CS. Preferably such compounds are proteins fusion proteins or lipids. Preferably the proteins are of eukaryotic, preferably vertebrate most preferably of mammalian origin or derived therefrom.

The term "a molecule lacking fucose on its glycomoieties" in the context of the present invention means that on a molecule which naturally comprises fucose on its glycomoieties, no detectable amount of fucose is present. Expressed in terms of purity, "a molecule lacking fucose on its glycomoieties" means that a molecule which naturally comprises fucose on its glycomoieties is to 100% free of the sugar residue fucose on its glycomoieties.

The term "a molecule with a reduced amount of fucose on its glycomoieties" refers to a molecule, wherein the amount of fucose on the glycomoieties is reduced from the number (n) when expressed in a cell capable of adding fucose to glycomoieties, i.e. with an unaltered ability to add fucose to glycomoieties. Thus, the reduced state is n−x, wherein n has the meaning indicated above and x is an integer of 1 to (n−1). Preferably, if n is 2 in the natural state it is reduced to 1. Similarly, if n is 3 in the natural state, it is preferably reduced to 2, or 1; if n is 4 in the natural state, it is preferably reduced to 3, 2, or 1; if n is 5 in the natural state, it is preferably reduced to 4, 3, 2, or 1; or if n is 6 in the natural state, it is preferably reduced to 5, 4, 3, 2, or 1.

The term "a composition of molecules with a reduced amount of fucose on their glycomoieties" is used in the context of the present invention to indicate that molecules of a composition which naturally comprises fucose on its glycomoieties have a reduced number of fucose on their glycomoieties. Such comparison is preferably carried out using molecules produced by the cell lines indicated above. Expressed in terms of reduction it means that of a given number of molecules of a composition, preferably of 1, 10, 100 or 1000 pmol of molecules of a composition, the number of fucose residues is reduced between 10% to 95%, preferably about 15%, about 20%, about 25%, about 30%, about 35%, 40%, about 45%, about 50%, about 55%, about 60%, about 65%, about 70%, about 75%, about 80%, about 85%, about 86%, about 87%, about 88%, about 89%, about 90%, about 91%, about 92%, about 93%, or about 94%. The overall reduction may be due to an increase of molecules in the composition lacking fucose on its glycomoieties and/or having a reduced amount of fucose on their glycomoieties.

The term "a composition of molecules which are substantially free of fucose on their glycomoieties" is used in the context of the present invention to indicate that molecules of a composition, which naturally comprises fucose on their glycomoieties, are essentially devoid of the sugar residue fucose on their glycomoieties. Expressed in terms of purity, the term "a composition of molecules which are substantially free of fucose on their glycomoieties" means that of a given number of molecules of a composition, preferably of 1, 10, 100 or 1000 pmol of molecules of a composition, at least about 95%, about 96%, about 97%, about 98%, about 99%, about 99.1%, about 99.2%, about 99.3%, about 99.4%, about 99.5%, about 99.6%, about 99.7%, about 99.8%, or at least about 99.9% of said molecules are free of the sugar residue fucose on their glycomoieties.

The skilled person can easily determine experimentally the reduced amount of fucose on the glycomoieties of a particular molecule, e.g. an antibody molecule, by (i) cultivating cells of the present invention under conditions wherein the molecule of interest is produced, (ii) isolating said molecule from said cells and (iii) analysing the sugar chain structure of said molecule with respect to the fucose residues attached to its glycomoieties and calculating the mean value of fucose residues present on the sugar chain structure of said molecule, and (iv) comparing the result with the result of the same molecule, e.g. an antibody molecule, produced in cells, wherein the molecule is produced with a fucose-unreduced glycosylation pattern. Preferably, the cells used in the two experiments are identical but for the difference that one cell comprises at least one enzyme which uses GDP-6-deoxy-D-lyxo-4-hexulose as a substrate, wherein the enzyme does not catalyze the reaction which converts GDP-6-deoxy-D-lyxo-4-hexulose into GDP-L-fucose. Preferably both cells are cultivated under the identical culture conditions to exclude variations in fucosylation that may be due to differences in culture conditions.

The sugar chain structure in a molecule, e.g. antibody molecule, can simply be analyzed by the two dimensional sugar chain mapping method (Anal. Biochem., 171, 73 (1988), Biochemical Experimentation Methods 23—Methods for Studying Glycoprotein Sugar Chains (Japan Scientific Societies Press) edited by Reiko Takahashi (1989)). The structure deduced by the two dimensional sugar chain mapping method can be determined by carrying out mass spectrometry such as MALDI (Matrix Assisted Laser Desorption/Ionisation)-TOF-MS of each sugar chain.

Fucosylation of molecules, e.g. proteins or lipids, comprising glycomoieties in eukaryotic cells (e.g. vertebrate cells) requires a nucleotide sugar, GDP-L-fucose, as a donor and also the presence of particular fucosyltransferases, which transfer the fucosyl residue from the donor to the acceptor molecule. In eukaryotic cells (e.g. vertebrate cells) GDP-L-fucose can be synthesized via two different pathways, either by the more prominent fucose de novo pathway or by the minor salvage pathway.

The inventors of the present invention have found that the presence of an enzyme (deflecting enzyme) in a eukaryotic cell (e.g. a vertebrate cell) which effectively utilizes GDP-6-deoxy-D-lyxo-4-hexulose as a substrate, but which does not catalyse the reaction which converts GDP-6-deoxy-D-lyxo-4-hexulose into GDP-L-fucose, leads to the production of a molecule, e.g. protein or lipid, lacking fucose or with a reduced amount of fucose on its glycomoieties. The term "GDP-6-deoxy-D-lyxo-4-hexulose" is synonym with the term "GDP-4-keto-6-deoxy-D-mannose". Both terms are used interchangeably herein.

Thus, in a first aspect, the present invention provides a (modified) vertebrate cell for producing a molecule, which naturally comprises fucose on its glycomoieties, lacking fucose or with a reduced amount of fucose on its glycomoieties comprising at least one enzyme which uses GDP-6-deoxy-D-lyxo-4-hexulose as a substrate, wherein the enzyme does not catalyze the reaction which converts GDP-6-deoxy-D-lyxo-4-hexulose into GDP-L-fucose.

The enzyme present in the vertebrate cell of the first aspect of the invention can be any enzyme which uses GDP-6-deoxy-D-lyxo-4-hexulose as a substrate under the proviso that said enzyme does not catalyze the reaction which converts GDP-6-deoxy-D-lyxo-4-hexulose into GDP-L-fucose. Rather said enzyme converts GDP-6-deoxy-D-lyxo-4-hexulose into a product that can no longer be utilized for GDP-L-fucose synthesis in a vertebrate cell. The enzyme which is comprised in the vertebrate cell of the first aspect of the present invention is an enzyme which is normally not present in the vertebrate cell, i.e. a heterologous or artificial enzyme, e.g. an enzyme from an organism of another kingdom, such as from prokaryotes, preferably bacteria. Alternatively said enzyme can also be an enzyme which is normally present in a vertebrate cell, but which does not covert the substrate GDP-6-deoxy-D-lyxo-4-hexulose into GDP-L-fucose but rather into a different product, e.g. due to the presence of mutations.

The enzyme, which is present in the vertebrate cell of the first aspect of the present invention, has been introduced into the vertebrate cell, for example, via protein microinjection, protein electroporation or protein lipofection. It is also possible to introduce the nucleic acid sequence encoding the enzyme, preferably integrated in an expression vector, into the vertebrate cell, for example via DNA microinjection, DNA electroporation or DNA lipofection, which is subsequently transcribed and translated into the respective protein in the vertebrate cell. The person skilled in the art is well informed about molecular biological techniques, such as microinjection, electroporation or lipofection, for introducing proteins or nucleic acid sequences encoding proteins into a vertebrate cell and knows how to perform these techniques.

It is preferred that two or more enzymes, i.e. 2, 3, 4, 5, 6 or 7, which use GDP-6-deoxy-D-lyxo-4-hexulose as a substrate and which do not catalyze the conversion of GDP-6-deoxy-D-lyxo-4-hexulose into GDP-L-fucose are present in a vertebrate cell to effectively block the fucose de novo pathway in said cell.

Preferably, the enzyme which uses GDP-6-deoxy-D-lyxo-4-hexulose as a substrate is selected from the group consisting of GDP-6-deoxy-D-lyxo-4-hexulose reductase (synonym with GDP-4-keto-6-deoxy-D-mannose reductase, abbreviated RMD), GDP-perosamine synthetase (Per), GDP-6-deoxy-D-talose synthetase (GTS), GDP-Fucose synthetase Cys109Ser-(GFS-Cys109Ser) mutant, GDP-4-keto-6-deoxymannose-3-dehydratase (ColD), preferably GDP-4-keto-6-deoxymannose-3-dehydratase (ColD) in combination with GDP-L-colitose synthase (ColC), and variants thereof, preferably the enzyme is from bacteria or derived from such a bacterial enzyme. More preferably, the enzyme which uses GDP-6-deoxy-D-lyxo-4-hexulose as a substrate is a GDP-6-deoxy-D-lyxo-4-hexulose reductase (RMD), GDP-Fucose synthetase Cys109Ser-(GFS-Cys109Ser) mutant, and/or a GDP-perosamine synthetase (Per).

GDP-6-deoxy-D-lyxo-4-hexulose reductase (RMD) reduces the substrate GDP-6-deoxy-D-lyxo-4-hexulose to GDP-D-rhamnose. GDP-D-Rhamnose is a nucleotide sugar donor for D-rhamnosylation in bacteria and does not occur in vertebrates. Vertebrate cells also lack specific rhamnosyltransferases so that GDP-D-Rhamnose can not be incorporated into nascent glycostructures of glycoproteins or glycolipids within vertebrate cells.

The enzyme GDP-6-deoxy-D-talose synthetase (GTS) reduces the substrate GDP-6-deoxy-D-lyxo-4-hexulose to GDP-deoxy-D-talose. GDP-deoxy-D-talose is a nucleotide sugar donor for 6-deoxy-D-talosylation in bacteria and does not occur in vertebrates. Vertebrate cells also lack specific deoxytalosyltransferases so that GDP-deoxy-D-talose can not be incorporated into nascent glycostructures within vertebrate cells.

Further, the enzyme GDP-perosamine synthetase (Per) reduces and transaminates the substrate GDP-6-deoxy-D-lyxo-4-hexulose to GDP-D-perosamine. GDP-D-perosamine is a nucleotide sugar donor for perosaminylation in bacteria, e.g. E. coli. GDP-D-perosamine is normally not present in vertebrate cells. Vertebrate cells also lack specific perosaminyltransferases so that GDP-D-perosamine can not be attached to nascent glycostructures within vertebrate cells.

Therefore, the heterologous enzymes GTS and/or Per (i) deplete the substrate GDP-6-deoxy-D-lyxo-4-hexulose in the vertebrate cell, and (ii) lead to the synthesis of artificial products (i.e. GDP-deoxy-D-talose in the case of GTS and GDP-D-perosamine in the case of Per) which can no longer be utilized for GDP-L-fucose synthesis. Accordingly, the molecules, which normally comprise fucose on their glycomoieties, produced in the vertebrate cell comprising GTS and/or Per, lack fucose or with a reduced amount of fucose on their glycomoieties.

The enzyme GDP-4-keto-6-deoxymannose-3-dehydratase (ColD) uses the substrate GDP-6-deoxy-D-lyxo-4-hexulose and converts it into GDP-4-keto-3,6-dideoxy-D-mannose. As the intermediate GDP-4-keto-3,6-dideoxy-D-mannose can be instable in vertebrate cells, ColD is preferably used in combination with the enzyme GDP-L-colitose synthase (ColC). The enzyme ColC belongs to the class of GDP-4-dehydro-6-deoxy-D-mannose epimerases/reductases. The enzyme ColC further converts the intermediate GDP-4-keto-3,6-dideoxy-D-mannose into the stabile end-product GDP-L-colitose. Both products can not be incorporated into nascent glycostructures within vertebrate cells as said cells lack the respective glycosyltransferase to transfer GDP-4-keto-3,6-dideoxy-D-mannose and/or GDP-L-colitose to the glycomoieties of molecules present in said cells. Thus, it is preferred that ColD is present in the vertebrate cell in combination with ColC.

The enzyme GDP-Fucose synthetase (GFS) (also known as GDP-4-keto-6-deoxy-D-mannose epimerase/reductase, GMER) converts GDP-4-keto-6-deoxy-D-mannose into GDP-L-fucose in vertebrate cells. The GFS reaction involves epimerizations at both C-3" and C-5" followed by an NADPH-dependent reduction of the carbonyl at C-4. An active site mutant, preferably GFS-Cys109Ser, is used in the present invention, which converts GDP-4-keto-6-deoxy-D-mannose into a product different from GDP-L-fucose, namely GDP-6-deoxy-D-altrose (see Lau S. T. B., Tanner, M. E. 2008. Mechanism and active site residues of GDP-Fucose Synthase, Journal of the American Chemical Society, Vol. 130, No. 51, pp. 17593-17602).

Preferably, two or more enzymes, i.e. 2, 3, 4, 5, 6, or 7, selected from the group consisting of GDP-6-deoxy-D-lyxo-4-hexulose reductase (RMD), GDP-perosamine synthetase (Per), GDP-6-deoxy-D-talose synthetase (GTS), GDP-Fucose synthetase Cys109Ser-(GFS-Cys109Ser) mutant, GDP-4-keto-6-deoxymannose-3-dehydratase (ColD), preferably GDP-4-keto-6-deoxymannose-3-dehydratase (ColD) in combination with GDP-L-colitose synthase (ColC), and variants thereof are present in the vertebrate cell.

A RMD, Per, GTS, GFS-Cys109Ser, ColD, or ColC enzyme variant which is preferred in the present invention differs from the RMD, Per, GTS, GFS-Cys109Ser, ColD, or ColC enzyme from which it is derived by up to 150 (i.e. up to 1, 2, 3, 4, 5, 6, 7, 8, 9, 10, 11, 12, 13, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, or 150) amino acid changes in the amino acid sequence (i.e. exchanges, insertions, deletions, N-terminal truncations and/or C-terminal truncations). The amino acid exchanges may be conservative or non-conservative. A RMD, Per, GTS, GFS-Cys109Ser, ColD, or ColC enzyme variant, which is preferred in the present invention can alternatively or additionally be characterised by a certain degree of sequence identity to the RMD, Per, GTS, GFS-Cys109Ser, ColD, or ColC enzyme from which it is derived. Thus, the RMD, Per, GTS, GFS-Cys109Ser, ColD, or ColC enzyme variants, which are preferred in the present invention have a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference RMD, Per, GTS, GFS-Cys109Ser, ColD, or ColC enzyme. Preferably, the sequence identity is over a continuous stretch of 40, 45, 50, 60, 70, 80, 90, 100, 150, 200, 250, 300 or more amino acids, preferably over the whole length of the respective reference RMD, Per, GTS, GFS-Cys109Ser, ColD, or ColC enzyme. It is particularly preferred that the sequence identity is at least 80% over the whole length, is at least 85% over the whole length, is at least 90% over the whole length, is at least 95% over the whole length, is at least 98% over the whole length, or is at least 99.5% over the whole length of the respective reference RMD, Per, GTS, GFS-Cys109Ser, ColD, or ColC enzyme. It is also particularly preferred that the sequence identity is at least 80% over at least 200 or 250 amino acids, is at least 85% over at least 200 or 250 amino acids, is at least 90% over at least 200 or 250 amino acids, is at least 95% over at least 200 or 250 amino acids, is at least 98% over at least 200 or 250 amino acids, or is at least 99.5% over at least 200 or 250 amino acids of the respective reference RMD, Per, GTS, GFS-Cys109Ser, ColD, or ColC enzyme.

A fragment (or deletion variant) of the RMD, Per, GTS, GFS-Cys109Ser, ColD, or ColC enzyme has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, or 150 amino acids at its N-terminus and/or at its C-terminus and/or internally.

Additionally, a RMD, Per, GTS, GFS-Cys109Ser, ColD, or ColC enzyme having above indicated degree of relatedness to the reference enzyme is only regarded as a variant, if it exhibits the relevant biological activity to a degree of at least 30% of the activity of the respective reference enzyme. The relevant "biological activity" in the context of the present invention is the "enzyme activity", i.e. the activity of the RMD, Per, GTS, GFS-Cys109Ser, ColD, or ColC enzyme variant to utilized the substrate GDP-6-deoxy-D-lyxo-4-hexulose and covert it into GDP-D-rhamnose, GDP-D-perosamine, GDP-deoxy-D-talose, GDP-6-deoxy-D-altrose, GDP-4-keto-3,6-dideoxy-D-mannose or GDP-L-colitose, respectively. The skilled person can readily assess whether a RMD, Per, GTS, GFS-Cys109Ser, ColD, or ColC enzyme variant has an enzyme activity of at least 30% of the enzyme activity of the respective reference RMD, Per, GTS, GFS-Cys109Ser, ColD, or ColC enzyme. Suitable assays, e.g. enzyme activity assays, for determining the "enzyme activity" enzyme variant compared to the enzyme activity of the respective reference enzyme are known to the person skilled in the art.

Preferably, the enzyme GDP-6-deoxy-D-lyxo-4-hexulose reductase (RMD) is from *Pseudomonas aeruginosa* (SEQ ID NO: 1). The enzyme GDP-6-deoxy-D-talose synthetase (GTS) is preferably from *Actinobacillus actinomycetemcomitans* (SEQ ID NO: 2). It is preferred that the enzyme GDP-perosamine synthetase (Per) is from *Vibrio cholerae* (SEQ ID NO: 3). Preferably, the GDP-4-keto-6-deoxymannose-3-dehydratase (ColD) is from *E. coli* (SEQ ID NO: 4). The use of GDP-L-colitose synthase (ColC) from *E. coli* is also preferred (SEQ ID NO: 7). The wild-type GDP-Fucose synthetase (GFS) is from *Cricetulus griseus* (Chinese hamster) (SEQ ID NO: 5). The GDP-Fucose synthetase Cys109Ser-(GFS-Cys109Ser) mutant from *Cricetulus griseus* (Chinese hamster) has the amino acid sequence of SEQ ID NO: 6.

As mentioned above, the invention encompasses variants of the enzymes using GDP-6-deoxy-D-lyxo-4-hexulose as a substrate. Thus, the present invention also covers variants of the above mentioned sequence identifier numbers, i.e. SEQ ID NO: 1 variants, SEQ ID NO: 2 variants, SEQ ID NO: 3 variants, SEQ ID NO: 3 variants, SEQ ID NO: 4 variants, SEQ ID NO: 5 variants, SEQ ID NO: 6 variants, and SEQ ID NO: 7 variants. As to the structural and/or functional definition of said variants, it is referred to the aforementioned paragraphs.

Preferably, the nucleic acid sequences of RMD, Per, GTS, ColD, ColC, or GFS-Cys109Ser are codon-optimized. The term "codon-optimized" as used in the context of the present invention means, for example, the removal of internal Tata boxes, chi sites, ribosome entry sites, RNA instability motifs, repeat sequences, intense RNA secondary structures and cryptic splice sites as well as the use of codons of higher utilization in eukaryotic (e.g. vertebrate) cells or of highly expressed genes in eukaryotic (e.g. vertebrate) cells.

It is further preferred that additionally the fucose salvage pathway is blocked in the vertebrate cell. Thus, it is preferred to use growth media free of fucose and of fucosylated glycoproteins, when culturing the cells of the present invention.

The vertebrate cell further or alternatively to the enzyme comprises GDP-D-rhamnose, GDP-D-perosamine, GDP-deoxy-D-talose, GDP-6-deoxy-D-altrose, GDP-4-keto-3,6-dideoxy-D-mannose, and/or GDP-L-colitose to inhibit or prevent GDP-L-fucose synthesis as the inventors of the present invention have unexpectedly noticed that the supplementation, particularly the cytosolic supplementation, e.g. by intracytoplasmic injection, of the artificial sugars GDP-D-rhamnose, GDP-D-perosamine, GDP-deoxy-D-talose, GDP-6-deoxy-D-altrose, GDP-4-keto-3,6-dideoxy-D-mannose, and/or GDP-L-colitose positively contributes to the inhibition of fucose transfer in vertebrate cells. The supplementation of the artificial sugar(s) GDP-6-deoxy-D-altrose, GDP-D-rhamnose, and for GDP-D-perosamine is (are) particularly preferred.

It is preferred that the enzyme which uses GDP-6-deoxy-D-lyxo-4-hexulose as a substrate and which does not catalyze the reaction which converts GDP-6-deoxy-D-lyxo-4-hexulose into GDP-L-fucose is expressed from a nucleic acid sequence transiently present or stably maintained in the vertebrate cell either episomally or chromosomally.

The nucleic acid sequence encoding the enzyme, preferably GDP-6-deoxy-D-lyxo-4-hexulose reductase (RMD), GDP-perosamine synthetase (Per), GDP-6-deoxy-D-talose synthetase (GTS), GDP-Fucose synthetase Cys109Ser-(GFS-Cys109Ser) mutant, GDP-4-keto-6-deoxymannose-3-dehydratase (ColD), or GDP-L-colitose synthase (ColC) is integrated in an expression vector, which is used to transform the cell.

Suitable expression vectors comprise plasmids cosmids, bacterial artificial chromosomes (BAC) and viral vectors. Preferably, non-viral expression vectors are used.

The expression of the nucleic acid encoding the enzyme is controlled by expression control sequences.

The terms "expression control sequences" refers to nucleotide sequences which are affect the expression in eukaryotic cells (e.g. vertebrate cells) of coding sequences to which they are operably linked. Expression control sequences are sequences which control the transcription, e.g. promoters, TATA-box, enhancers; post-transcriptional events, e.g. polyadenylation; and translation of nucleic acid sequences.

Preferred promoters are constitutive promoters including the cytomegalovirus hCMV immediate early gene promoter, the early or late promoters of SV40 or regulated promoters including the CUP-1 promoter, the tet-repressor as employed, for example, in the tet-on or tet-off systems, the promoter for 3-phosphoglycerate kinase (PGK), the promoters of acid phosphatase, and the promoters of the yeast α- or α-mating factors, e.g the constitutive CMV immediate early gene promoter, the early or late SV 40 promoter, the polyhedrin promoter, retroviral LTRs, PGK promoter, elongation factor 1-α (EF 1-α), EF2 and phosphoenolpyruvate carboxy kinase (PEPCK). Particularly preferred promoters are promoters which support only intermediate or weak expression of the enzyme to avoid potential toxicity problems. The expression strength of a given promoter can be normalized by comparing the expression to the expression strength of the strong constitutive promoter directing expression of endogenous GAPDH. A promoter directing expression of the enzyme at a strength of 10% to 1% of GAPDH is considered a promoter directing intermediate expression and a promoter with directing expression of the enzyme at a strength of less than 1% is considered a weak promoter. Expression strength can be assessed by art know methods including, e.g. real time PCR.

Marker tags can also be used in the embodiments of the present invention. Preferably, the nucleic acid sequence of the marker tag is operably linked to the nucleic acid sequence encoding the protein (e.g. enzyme, antibody) to be tagged. Preferably the marker tag is a fluorescent protein selected from the group consisting of GFP and variants thereof; including, but not limited to, GFP. As used herein "operably linked" means that one nucleic acid is linked to a second nucleic acid in such a way that in-frame expression of a corresponding fusion protein can be affected avoiding frameshifts or stop codons. These terms also mean the linking of expression control sequences to a coding nucleic acid sequence of interest (e.g. enzyme, antibody) to effectively control the expression of said sequence. These terms also refer to the linking of nucleic acid sequences encoding an affinity tag or marker tag to a coding nucleic acid sequence of interest (e.g. enzyme, antibody).

It is preferred that the nucleic acid sequence encoding the enzyme RMD, Per, GTS, GFS-Cys109Ser, ColD or ColC in the expression vector is operably inked to vertebrate specific expression control sequences, which allow the expression of the nucleic acid sequence encoding the enzyme RMD, Per, GTS, GFS-Cys109Ser, ColD or ColC in the vertebrate cell.

As a result, the enzyme(s) RMD, Per, GTS, GFS-Cys109Ser, and/or ColD, ColD preferably in combination with ColC, are expressed in the vertebrate cell of the present invention in yields optimal for the desired effect. Depending on the nature of the enzyme and the cell used for expression these yields may be high moderate or low. It is easy for those skilled in the art to choose appropriate vertebrate specific expression control sequences to achieve high, moderate or low level of expression.

The expression of the enzyme(s) RMD, Per, GTS, GFS-Cys109Ser, and/or ColD, ColD preferably in combination with ColC, in the vertebrate cell has the effect that it effectively blocks the GDP-L-fucose synthesis and, thus, leads to the production of molecules, which naturally comprise fucose on their glycomoieties, but which due to their expression lack fucose or have a reduced amount of fucose on their glycomoieties.

For long-term, high-yield production of a recombinant proteins stable expression is preferred. For example, eukaryotic cells (e.g. vertebrate cells) that stably express nucleic acids encoding the enzyme which uses GDP-6-deoxy-D-lyxo-4-hexulose as a substrate, wherein the enzyme does not catalyze the reaction which converts GDP-6-deoxy-D-lyxo-4-hexulose into GDP-L-fucose and the protein, e.g. an antibody, may be engineered. Rather than using expression vectors that contain viral origins of replication, eukaryotic cells (e.g. vertebrate cells) can be transformed with vectors controlled by appropriate expression control sequences (e.g., promoter, enhancer, sequences, transcription terminators, polyadenylation sites, etc.) and optionally a selectable marker. Following the introduction of foreign DNA, transformed cells may be detected by analysing nucleic acids from such cells, by detecting the effect of expression (e.g. the lack of fucose using lectin binding) or may be selected by applying selective pressure. Suitable selection systems are well known in the art.

Preferably, the vertebrate cell further comprises at least one (acceptor) molecule which is capable of being a substrate for a fucosyltransferase. The term "(acceptor) molecule capable of being a substrate for a fucosyltransferase" as used in the context of the present invention refers to any compound of interest, e.g. a protein, a polypeptide, an oligopeptide, a lipid, a lipid fragment, or a fusion protein, having or comprising glycomoieties to which at least one fucose residue is attached, if produced in a cell having an unaltered fucosylation activity. Such a compound is a suitable substrate for a fucosyltransferase. A preferred acceptor molecule is accordingly a glycoprotein, a glycopolypeptide, a glycooligopeptide, a glycolipid, a glycolipid fragment, or a glycosylated fusion protein. The term "(acceptor) molecule capable of being a substrate for a fucosyltransferase" as used in the context of the present invention also refers to any protein or lipid, so long as it is a prospective glycoprotein or glycolipid to which at least one fucose residue can be attached, i.e. a protein or lipid to which oligosaccharide structures are linked comprising a monosaccharide to which fucose can be attached by the fucosyltransferase after its production by the vertebrate cell. Preferably the protein is not of prokaryotic origin. It is particularly preferred that the protein is a mammalian protein or derived therefrom.

The presence of a molecule capable of being a substrate for a fucosyltransferase, e.g. a protein or lipid comprising glycomoieties to which at least one fucose residue can be attached, in a vertebrate cell of the invention, leads to the production of this molecule that does not comprise fucose on its glycomoieties or that it has a reduced amount of fucose on its glycomoieties, in spite of the fact that fucose residues can be attached.

It is preferred that the molecule capable of being a substrate for a fucosyltransferase is a protein, preferably an endogenous or exogenous protein. The term "exogenous protein" means any protein that is either coming from the outside of the respective cell or that is expressed inside the cell from a nucleic acid introduced into the respective cell. The term "endogenous protein" refers to any protein that is encoded by the genome of the cell. Preferably, the protein of interest, namely the prospective glycoprotein, is recombinantly expressed in the vertebrate cell. It is preferred that said protein is expressed from a nucleic acid sequence transiently present or stably maintained in the vertebrate cell. Suitable expression vectors and expression control sequences have been described above with respect to the enzyme. These can equally be used in the context of the expression of the nucleic acid encoding the protein of interest.

Thus, in a preferred embodiment of the present invention, the vertebrate cell comprises (i) at least one polynucleotide comprising a nucleic acid sequence encoding the enzyme GDP-6-deoxy-D-lyxo-4-hexulose reductase (RMD), GDP-perosamine synthetase (Per), GDP-6-deoxy-D-talose synthetase (GTS), GDP-Fucose synthetase Cys109Ser-(GFS-Cys109Ser) mutant, GDP-4-keto-6-deoxymannose-3-dehydratase (ColD), or GDP-L-colitose synthase (ColC), operably linked to vertebrate specific expression control sequences, which allow the expression of the nucleic acid sequence encoding the respective enzyme, and (ii) at least one polynucleotide comprising a nucleic acid sequence encoding the protein of interest, namely the prospective glycoprotein, e.g. an antibody, such as IgG1, operably linked to vertebrate specific expression control sequences, which lead to expression of the nucleic acid sequence encoding the protein of interest, e.g. an antibody, such as IgG1, in said cell.

As a result, (i) the enzyme(s) RMD, Per, GTS, GFS-Cys109Ser, and/or ColD, ColD preferably in combination with ColC, and (ii) the protein(s) of interest, namely the prospective glycoprotein(s), e.g. an antibody, such as IgG1, are expressed in the vertebrate cell of the present invention.

Preferably, in the first aspect of the invention the protein is an antibody, an antibody fragment, a fusion protein, a virus protein, a virus protein fragment, an antigen, or a hormone. Most preferably, the antibody or the antibody fragment is selected from the group consisting of IgG, preferably IgG1, IgG2, IgG3, IgG4, IgM, IgA, IgD and IgE. Most preferably, the fusion protein comprises the Fc region of an antibody, e.g. the Fc region of IgG, such as the Fc region of IgG1, IgG2, IgG3, IgG4, IgM, IgA, IgD or IgE. Most preferably, the hormone is the Follicle-stimulating hormone (FSH), gonadotropic hormone, thyroid-stimulating hormone, interleukine-2, interleukin-6, interleukine-10, interleukin-11, soluble interleukin-4, erythropoietin, or thrombopoietin. Preferably, the virus protein or virus protein fragment is comprised in the envelope membrane of an enveloped virus. It is particularly preferred that the virus protein is G or F protein from Respiratory Syncytial Virus and that the virus protein fragment is the extracellular fragment of said protein.

A further aspect of the invention is a virus comprising said virus protein or virus protein fragment.

It is preferred that the molecule capable of being a substrate for a fucosyltransferase is a lipid. Preferably, the lipid is a glyceroglycolipid, most preferably a galactolipid, a sulfolipid (SQDG), or a glycosphingolipids, most preferably a cerebroside (e.g. a galactocerebroside or a glucocerebroside), a ganglioside, a globoside, a sulfatide or a glycophosphinogolipid. It is particularly preferred that the lipid is comprised in the envelope membrane of an enveloped virus.

The glycosphingolipid (GSL) is particularly preferred. Glycosphingolipids contain a hydrophobic ceramide anchor N-acylsphingosine and a hydrophilic head-group composed of saccharides. They are normally found at the outer surface of cell membranes. The composition of the saccharide-moiety is cell type specific and depends on the developmental stage of the organism or can change with the oncogenic state of a cell.

Most preferably, the virus protein and/or lipid are comprised in the envelope of an enveloped virus.

As already mentioned above, the protein can be a virus protein which is comprised in the envelope membrane of an enveloped virus. The lipid can also be lipid comprised in the envelope membrane of an enveloped virus.

A further aspect of the invention is a virus comprising said lipid.

The above mentioned virus can be introduced into the vertebrate cell via virus infection. The virus can also be introduced into the vertebrate cell by introducing nucleic acids encoding all or part of the virus to be produced. In the case it will be necessary to provide proteins required for replication, assembly etc., this is usually achieved by using viral producer cell lines capable of expressing one or more virus proteins. For example HEK293, Per.C6 and AGE1.HN cells express adenovirus E1A proteins and are, thus, capable of complementing DNA lacking E1 coding regions.

Preferably, the vertebrate cell is a mammalian, a fish, an amphibian, a reptilian cell or an avian cell.

It is particularly preferred that i) the mammalian cell is a human, hamster, canine or monkey cell, preferably a Chinese hamster ovary cell (CHO), an African green monkey kidney cell (VERO-76) (ATCC CRL- 1587), a human cervical carcinoma cell (HeLa) (ATCC CCL 2), a Madin Darbin canine kidney cell (MDCK) (ATCC CCL 34), a human PER.C6 cell (commercial cell of Crucell, Leiden, The Netherlands), or a human (*homo sapiens*) AGE1.HN cell (commercial cell of ProBioGen, Berlin, Germany);

ii) the fish cell is a *Ictalurus punctatus* (channel catfish) ovary (CCO) cell (ATCC CRL-2772), iii) the amphibian cell is a *Xenopus laevis* kidney cell (ATCC CCL-102);

iv) the reptilian cell is a *Iguana iguana* heart cells (IgH-2) (ATCC CCL-108); or v) the avian cell is an avian retina cell AGE1.CR or AGE1.CR.PIX, or an avian somite cell AGE1.CS (all cells derived from Muscovy duck, *Cairina moschata*). These cell lines are all commercially available from ProBioGen AG.

The cell line AGE1.CR.PIX (17a11b) was deposited by ProBioGen AG, Goethestr. 54, 13086 Berlin, Germany with the DSMZ-Deutsche Sammlung von Mikroorganismen und Zellkulturen GmbH, Mascheroder Weg 1b, 38124 Braunschweig, Germany on Nov. 24, 2005 under accession number DSM ACC2749. The cell line AGE1.HN (NC5T11#34) was deposited by ProBioGen AG, Goethestr. 54, 13086 Berlin, Germany with the DSMZ-Deutsche Sammlung von Mikroorganismen und Zellkulturen GmbH, Mascheroder Weg 1b, 38124 Braunschweig, Germany on Nov. 4, 2005 under accession number DSM ACC2744. The cell line AGE1.CR.PIX (17a11b) is derived from embryonic retina cells of Muscovy duck (*Cairina moschata*). The cell line AGE1.HN (NC5T11#34) is derived from a periventricular neural region of a human (*Homo sapiens*) fetus. Both cell lines are immortalized by stable integration and expression of adenovirus E1A and E1B proteins.

Another preferred vertebrate cell is the avian EB14 cell which is a commercial cell of VIVALIS (Nantes, France). Other preferred vertebrate cells are summarized in the following Table 1:

dideoxy-D-mannose, or GDP-L-colitose as said sugars are normally not synthesized or present in vertebrate cells. Thus, even if the artificial sugars GDP-D-rhamnose, GDP-D-perosamine, GDP-deoxy-D-talose, GDP-6-deoxy-D-altrose, GDP-4-keto-3,6-dideoxy-D-mannose, or GDP-L-colitose are unnaturally produced in the vertebrate cell according to the first aspect of the present invention, they can not be incorporated into nascent glycostructures of proteins or lipids.

The inventors of the present invention, however, have unexpectedly found that the artificial sugars GDP-D-rhamnose, GDP-D-perosamine, GDP-deoxy-D-talose, GDP-6-deoxy-D-altrose, GDP-4-keto-3,6-dideoxy-D-mannose, or GDP-L-colitose can be integrated into glycan structures of proteins or lipids under the proviso that the respective heterologous glycosyltransferase, and optionally a respective heterologous GDP-Deoxyhexose sugar nucleotide transporter is (are) also present in the vertebrate cell.

Accordingly, in a preferred embodiment, the vertebrate cell according to the first aspect of the present invention further comprises at least one glycosyltransferase for GDP-D-rhamnose, GDP-D-perosamine, GDP-deoxy-D-talose, GDP-6-deoxy-D-altrose, GDP-4-keto-3,6-dideoxy-D-mannose, or GDP-L-colitose, preferably encoded by a nucleic acid comprised in the vertebrate cell and operably linked to vertebrate specific expression control sequences, which allow the expression of said nucleic acid sequence, and optionally at least one GDP-deoxyhexose sugar nucleotide transporter for GDP-D-rhamnose, GDP-D-perosamine, GDP-deoxy-D-talose, GDP-6-deoxy-D-altrose, GDP-4-keto-3,6-dideoxy-D-mannose, or GDP-L-colitose, preferably encoded by a nucleic acid comprised in the vertebrate cell and operably linked to vertebrate specific expression control sequences, which allow the expression of said nucleic acid sequence. In a more preferred embodiment, the vertebrate cell according to

TABLE 1

| CELL LINE | DEPOSITION NUMBER | ORIGIN |
|---|---|---|
| NS0 | ECACC No. 85110503 | Mouse Myeloma |
| Sp2/0-Ag14 | ATCC CRL-1581 | Mouse Myeloma |
| BHK21 | ATCC CCL-10 | Baby Hamster Kindney |
| BHK TK⁻ | ECACC No. 85011423 | Baby Hamster Kindney |
| HaK | ATCC CCL-15 | |
| 2254-62.2 (BHK-21 derivative) | ATCC CRL-8544 | Baby Hamster Kindney |
| CHO wild type | ECACC 00102307 | Chinese Hamster Ovary; *Cricetulus griseus* |
| CHO-K1 | ATCC CCL-61 | Chinese Hamster Ovary; *Cricetulus griseus* |
| CHO-DUKX (=CHO duk⁻, CHO/dhfr⁻) | ATCC CRL-9096 | Chinese Hamster Ovary; *Cricetulus griseus* |
| CHO-DUKX B11 | ATCC CRL-9010 | Chinese Hamster Ovary; *Cricetulus griseus* |
| CHO-DG44 | not deposited at ATCC (Urlaub et al., 1983) | Chinese Hamster Ovary; *Cricetulus griseus* |
| CHO Pro-5 | ATCC CRL-1781 | Chinese Hamster Ovary; *Cricetulus griseus* |
| V79 | ATCC CCC-93 | |
| B14AF28-G3 | ATCC CCL-14 | |
| HEK 293 | ATCC CRL-1573 | Human Embryo Kidney |
| COS-7 | ATCC CRL-1651 | |
| U266 | ATCC TIB-196 | |
| HuNS1 | ATCC CRL-8644 | |
| CHL | ECACC No. 87111906 | |

Vertebrate cells naturally do not comprise a glycosyltransferase for GDP-D-rhamnose, GDP-D-perosamine, GDP-deoxy-D-talose, GDP-6-deoxy-D-altrose, GDP-4-keto-3,6- the first aspect of the present invention further comprises a glycosyltransferase for GDP-D-rhamnose, GDP-D-perosamine, and/or GDP-6-deoxy-D-altrose.

It is particularly preferred that two or more, e.g. 2, 3, 4, 5, 6, or 7, of the above mentioned glycosyltransferases, and optionally two or more, e.g. 2, 3, 4, 5, 6, or 7, of the above mentioned GDP-deoxyhexose sugar nucleotide transporter are present in the vertebrate cell, e.g. eukaryotic cell.

Suitable systems for transient or stable expression of such nucleic acids are known to the skilled person and preferred ones are described above and can similarly be used in the context of expressing glycosyltransferase, and optionally GDP-deoxyhexose sugar nucleotide transporter.

Preferably, the glycosyltransferase for GDP-D-rhamnose, GDP-D-perosamine, GDP-deoxy-D-talose, GDP-6-deoxy-D-altrose, GDP-4-keto-3,6-dideoxy-D-mannose, or GDP-L-colitose is recombinantly expressed in the vertebrate cell. The glycosyltransferase for GDP-D-rhamnose, GDP-D-perosamine, GDP-deoxy-D-talose, GDP-6-deoxy-D-altrose, GDP-4-keto-3,6-dideoxy-D-mannose, or GDP-L-colitose can be expressed from a nucleic acid sequence transiently present or stably maintained in the vertebrate cell. It is also preferred that the above mentioned GDP-deoxyhexose sugar nucleotide transporter is recombinantly expressed in the vertebrate cell. Said GDP-deoxyhexose sugar nucleotide transporter can be expressed from a nucleic acid sequence transiently present or stably maintained in the vertebrate cell.

Thus, in another preferred embodiment of the present invention, the vertebrate cell comprises (i) at least one polynucleotide comprising a nucleic acid sequence encoding the enzyme GDP-6-deoxy-D-lyxo-4-hexulose reductase (RMD), GDP-perosamine synthetase (Per), GDP-6-deoxy-D-talose synthetase (GTS), GDP-Fucose synthetase Cys109Ser-(GFS-Cys109Ser) mutant, GDP-4-keto-6-deoxymannose-3-dehydratase (ColD), or GDP-L-colitose synthase (ColC) operably linked to vertebrate specific expression control sequences, (ii) at least one polynucleotide comprising a nucleic acid sequence encoding a protein of interest, namely a prospective glycoprotein, e.g. an antibody, such as IgG1, operably linked to vertebrate specific expression control sequences, which allow the expression of the nucleic acid sequence encoding said protein in said cell, and (iii) at least one polynucleotide comprising a nucleic acid sequence encoding the glycosyltransferase for GDP-D-rhamnose, GDP-D-perosamine, GDP-deoxy-D-talose, GDP-6-deoxy-D-altrose, GDP-4-keto-3,6-dideoxy-D-mannose, or GDP-L-colitose operatively linked to vertebrate specific expression control sequences, which allow the expression of the nucleic acid sequence encoding said protein in said cell, and optionally (iv) at least one polynucleotide comprising a nucleic acid sequence encoding the GDP-deoxyhexose sugar nucleotide transporter for GDP-D-rhamnose, GDP-D-perosamine, GDP-deoxy-D-talose, GDP-6-deoxy-D-altrose, GDP-4-keto-3,6-dideoxy-D-mannose, or GDP-L-colitose operatively linked to vertebrate specific expression control sequences, which allow the expression of the nucleic acid sequence encoding said protein in said cell.

As a result, (i) the enzyme(s), (ii) the protein(s) of interest, (iii) the glycosyltransferase(s), and optionally (iv) the GDP-deoxyhexose sugar nucleotide transporter are overexpressed in the vertebrate cell of the present invention.

Said protein(s) are further modified by the co-expressed glycosyltransferase(s), which make(s) use of the end-product(s) of the enzyme(s), namely GDP-D-rhamnose, GDP-D-perosamine, GDP-deoxy-D-talose, GDP-6-deoxy-D-altrose, GDP-4-keto-3,6-dideoxy-D-mannose, and/or GDP-L-colitose, and integrate them into the glycostructures of the protein(s) lacking fucose or with a reduced amount of fucose on its glycomoieties. This leads to the generation of new artificial protein(s) which comprise D-rhamnose, D-perosamine, deoxy-D-talose, 6-deoxy-D-altrose, 4-keto-3,6-dideoxy-D-mannose, and/or L-colitose on their glycomoieties.

Preferably, the above mentioned GDP-deoxyhexose sugar nucleotide transporter are Golgi GDP-deoxyhexose sugar nucleotide transporter, namely transporter which allow the transport of the above mentioned nucleotide sugars across the Golgi membrane of a vertebrate cell, e.g. eukaryotic cell.

The (modified) vertebrate cell according to the present invention can be used to produce enveloped viruses comprising envelope surface glycoproteins or glycolipids having no fucose on its glycomoieties or with a reduced amount of fucose on its glycomoieties.

Preferably, the enveloped virus is used entirely or in part as an active component of a viral vaccine. The term "viral vaccine" means a preparation of a weakened or killed virus that upon administration stimulates antibody production or cellular immunity against the virus but is incapable of causing severe infections.

The (modified) vertebrate cell according to the present invention can also be used to produce enveloped viruses comprising envelope surface glycoproteins or glycolipids which comprise D-rhamnose, D-perosamine, deoxy-D-talose, 6-deoxy-D-altrose, 4-keto-3,6-dideoxy-D-mannose, and/or L-colitose on its glycomoieties.

In a second aspect, the present invention relates to a method for producing a molecule, which naturally comprises fucose on its glycomoieties, lacking fucose or with a reduced amount of fucose on its glycomoieties comprising the steps of:

i) providing a vertebrate cell according to first aspect, ii) isolating the molecule which is capable of being a substrate for a fucosyltransferase, preferably a protein or lipid, from the cell in i).

Preferably, upon step i), the molecule which is capable of being a substrate for a fucosyltransferase, e.g. a protein, is expressed in the cell in i).

Said molecules, e.g. proteins or lipids lacking fucose or with a reduced amount of fucose on their glycomoieties, can be readily isolated in step ii) from the vertebrate cell.

Various isolation procedures are known in the art for molecules enclosed inside eukaryotic cells (e.g. vertebrate cells) or secreted from such cells comprising the modified molecules, e.g. proteins lacking fucose or with a reduced amount of fucose on its glycomoieties.

Such methods typically involve cell harvest, disintegration and fractionation/purification in the case of intracellular molecules and generation of a cell free culture supernatant followed by purification of secreted molecules.

An extraction procedure that is useful according to the invention does not interfere with modified molecules to be isolated. For example, extraction is preferably performed in the absence of strong detergents and reducing agents, or any agent that may induce protein denaturation.

In a third aspect, the present invention provides a molecule lacking fucose or with a reduced amount of fucose on its glycomoieties obtainable by the method of the second aspect. Preferably, this molecule is a lipid or protein.

It is particularly preferred that the protein is an antibody, a hormone, an antigen or a virus protein as set out above with respect to the first aspect.

It is particularly preferred that the lipid is a glyceroglycolipid, most preferably a galactolipid, a sulfolipid (SQDG), or a glycosphingolipids, most preferably a cerebroside (e.g. a galactocerebroside or a glucocerebroside), a ganglioside, a globoside, a sulfatide or a glycophosphingolipid. Preferably, the lipid, e.g. ganglioside, is comprised in the membrane of an enveloped virus.

Most preferably, the virus protein and/or lipid are comprised in the envelope of an enveloped virus.

In a further aspect, the present invention provides a composition of molecules according to the third aspect.

In a fourth aspect, the present invention provides a molecule comprising glycomoieties containing D-rhamnose, D-perosamine, deoxy-D-talose, 6-deoxy-D-altrose, 4-keto-3,6-dideoxy-D-mannose, and/or L-colitose obtainable by the method of the second aspect.

It is preferred that this molecule comprises no or a reduced amount L-fucose on its glycomoieties. Preferably, this molecule is a lipid or protein. Additionally vertebrate cells are provided, preferably tumor cells that express such modified molecules, preferably lipids and/or proteins. Particularly preferred are tumor cells containing glycans comprising D-rhamnose. D-rhamnose is a building block of *Ganoderma lucidum* polysaccharides. These polysaccharides are used in traditional Chinese medicine to enhance the activity of immunological effector cells: NK cells and lymphokine activated killer cells are activated and phagocytosis and cytotoxicity of macrophages are increased (Zhu et al., 2007, Journal of Ethnopharmacology 111 (2), 219-226). Such cells may be used to increase the immune response against a given tumor cell, e.g. as in an active immunization approach.

In a further aspect, the present invention provides a composition of molecules according to the fourth aspect.

In a fifth aspect, the present invention provides a composition comprising glycoproteins which comprise i) between 70 and 95%, i.e. 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, and 95%, preferably 80% of G0-GlcNac, G0, G1, and/or G2 complex type N-glycans, and ii) between 5 and 30%, i.e. 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, and 30%, preferably 20% high mannose type N-glycans, wherein the complex type N-glycans of the glycoproteins are free of fucose or substantially free of fucose. Preferably the glycoproteins of the composition are the above indicated preferred glycoproteins, in particular antibodies.

It is particularly preferred that of the complex type N-glycans within the composition 70% to 80%, preferably about 75% are G0 and 20% to 30%, preferably about 25% are G0-GlcNac, G1 and/or G2 complex type N-glycans, and/or that of the high mannose type N-glycans 45% to 55%, preferably about 50% are man5 glycans and 45 to 55%, preferably about 50% are man6, man7 and/or man8 N-glycans. It is understood that the numbers in each case add up to 100%.

It is also particularly preferred that of the complex type N-glycans within the composition 70% to 90%, preferably about 80% are G0 and 10% to 30%, preferably about 20% are G0-GlcNac, G1 and/or G2 complex type N-glycans, and/or that of the high mannose type N-glycans 60% to 85%, preferably about 70% are man5 glycans and 15 to 40%, preferably about 30% are man6, man7 and/or man8 N-glycans. It is understood that the numbers in each case add up to 100%.

The glycoproteins are preferably those indicated as preferred in the context of the first aspect of the invention, in particular antibodies, e.g. IgG1s, IgG2s, IgG3s or IgG4s, wherein these antibodies preferably have a higher ADCC activity than an antibody composition produced in a parent, non-modified cell (e.g. eukaryotic cell, such as vertebrate cell)

ADCC is the dominating mechanism by which antibodies directed against tumor (cancer) cells exhibit their effect). ADCC can also be used to eliminate specific immune cells to interrupt pathogenesis in autoimmune disease.

Various diseases including viral and bacterial infections can be prevented and treated by suppressing proliferation of cells infected with a virus or bacterium using the antibody having high ADCC activity according to the present invention.

In a sixth aspect, the present invention provides a protein, preferably a non-prokaryotic protein, preferably a virus or mammalian protein, or a lipid, preferably a non-prokaryotic lipid, e.g. a glycosphingolipid, which comprises glycomoieties containing D-rhamnose, D-perosamine, deoxy-D-talose, 6-deoxy-D-altrose, 4-keto-3,6-dideoxy-D-mannose, and/or L-colitose. Preferably, the virus protein and/or lipid are comprised in the envelope of an enveloped virus. Alternatively, eukaryotic, preferably vertebrate more preferably mammalian and most preferably human cells (allogenic or autologous tumor cells) are provided comprising such proteins and/or lipids.

Preferably, the protein or lipid comprises D-rhamnose, D-perosamine, deoxy-D-talose, 6-deoxy-D-altrose, 4-keto-3,6-dideoxy-D-mannose, and/or L-colitose, more preferably D-rhamnose and/or D-perosamine, on its glycomoieties and no or a reduced amount of L-fucose on its glycomoieties. It is clear that the proteins of the sixth aspect may also have all the properties, which are the consequence of using the preferred and particularly preferred aspects of the methods of the present invention.

It is known that artificial sugars, such as D-rhamnose, D-perosamine, deoxy-D-talose, 6-deoxy-D-altrose, 4-keto-3,6-dideoxy-D-mannose, and/or L-colitose, confer resistance to cationic peptides, e.g. polymyxin B, defensins, etc., for example, by neutralizing the charge on the bacterial surface (see Breazeale et al., 2003, The Journal of Biological Chemistry, 278, 24731-24739).

Defensins are small cysteine-rich cationic proteins found, for example, in eukaryotes (e.g. vertebrates). They are active against bacteria, fungi and many enveloped and non-enveloped viruses. They consist of 18-45 amino acids including 6 (in vertebrates) to 8 conserved cysteine residues. Eukaryotic (e.g. vertebrate) cells of the immune system contain these peptides to assist in killing phagocytised bacteria, for example in neutrophil granulocytes and almost all epithelial cells.

Thus, the establishment of enveloped viruses comprising virus proteins containing D-rhamnose, D-perosamine, deoxy-D-talose, 6-deoxy-D-altrose, 4-keto-3,6-dideoxy-D-mannose, and/or L-colitose, preferably the cationic amino sugar D-perosamine, on their glycomoieties is highly useful, for example, in the gene therapy as vectors, as these viruses would be resistant against attacks of defensins and other cationic peptides of the congenital immune defence. The production of viruses or virus glycoproteins containing one or more of the sugar residues D-rhamnose, D-perosamine, deoxy-D-talose, 6-deoxy-D-altrose, 4-keto-3,6-dideoxy-D-mannose, and/or L-colitose on its glycomoieties would be highly useful to induce a superior immune response. These sugar residue are naturally not present on mammalian glycoproteins. However, they are frequent on glycoproteins and lipopolisacharides of bacteria. *Pseudomonas aeruginosa* the origin of the RMD sequence is one of the most important bacterial pathogens encountered by immunocompromised hosts and patients with cystic fibrosis (CF).

Particularly, the establishment of proteins containing the sugar residue D-perosamine or enveloped viruses comprising virus proteins containing the sugar residue D-perosamine is, due to the cationicity of D-perosamine, favoured. A virus which comprises glycoproteins containing the sugar residue D-perosamine in its envelope has a cationic surface charge which can protect said virus against the congenital immune defence.

In an seventh aspect, the present invention provides an expression unit which comprises one or more vertebrate expression control sequences operatively linked to a (first) polynucleotide comprising a nucleic acid sequence encoding an enzyme which uses GDP-6-deoxy-D-lyxo-4-hexulose as a substrate, wherein the enzyme does not catalyze the reaction which converts GDP-6-deoxy-D-lyxo-4-hexulose into GDP-L-fucose.

The expression unit can be any expression system known to the person skilled in the art in which the one or more vertebrate expression control sequences and a (first) polynucleotide which comprises a nucleic acid sequence encoding an enzyme which uses GDP-6-deoxy-D-lyxo-4-hexulose as a substrate can be integrated, e.g. a plasmid, a cosmid, a virus etc.

Preferably, the one or more vertebrate expression control sequences comprised in the expression unit are operatively linked to the (first) polynucleotide comprising a nucleic acid sequence encoding an enzyme which uses GDP-6-deoxy-D-lyxo-4-hexulose as a substrate to allow the expression of the nucleic acid sequence encoding an enzyme which uses GDP-6-deoxy-D-lyxo-4-hexulose as a substrate in the vertebrate cell, e.g. CHO or HeLa cell.

Preferably, the expression vector, e.g. plasmid vector, allows the transient expression of a nucleic acid sequence encoding an enzyme which uses GDP-6-deoxy-D-lyxo-4-hexulose as a substrate in the cytoplasm of a vertebrate cell or allows the stable expression of a nucleic acid sequence encoding an enzyme which uses GDP-6-deoxy-D-lyxo-4-hexulose as a substrate in the vertebrate cell after integration of said sequence in the genome of said cell.

It is particularly preferred that the enzyme which uses GDP-6-deoxy-D-lyxo-4-hexulose as a substrate is selected from the group consisting of GDP-6-deoxy-D-lyxo-4-hexulose reductase (RMD), GDP-perosamine synthetase (Per), GDP-6-deoxy-D-talose synthetase (GTS), GDP-Fucose synthetase Cys109Ser-(GFS-Cys109Ser) mutant, GDP-4-keto-6-deoxymannose-3-dehydratase (ColD), preferably GDP-4-keto-6-deoxymannose-3-dehydratase (ColD) in combination with GDP-L-colitose synthase (ColC), and variants thereof.

Preferably, the expression unit further comprises a (second) polynucleotide comprising a nucleic acid sequence encoding a glycosyltransferase for GDP-D-rhamnose, GDP-D-perosamine, GDP-deoxy-D-talose, GDP-6-deoxy-D-altrose, GDP-4-keto-3,6-dideoxy-D-mannose, or GDP-L-colitose, preferably operatively linked to one or more vertebrate expression control elements, e.g. a promoter, and preferably comprised on an expression vector, e.g. plasmid vector, to allow the expression of the nucleic acid sequence encoding said glycosyltransferase in the vertebrate cell, e.g. CHO cell, HeLa cell or a tumor cell, preferably an autologous tumor cell, and optionally a (third) polynucleotide comprising a nucleic acid sequence encoding a GDP-deoxyhexose sugar nucleotide transporter for GDP-D-rhamnose, GDP-D-perosamine, GDP-deoxy-D-talose, GDP-6-deoxy-D-altrose, GDP-4-keto-3,6-dideoxy-D-mannose, or GDP-L-colitose, preferably operatively linked to one or more vertebrate expression control elements, e.g. a promoter, and preferably comprised on an expression vector, e.g. plasmid vector, to allow the expression of the nucleic acid sequence encoding said GDP-deoxyhexose sugar nucleotide transporter in the vertebrate cell, e.g. CHO cell, HeLa cell or a tumor cell, preferably an autologous tumor cell.

Said first, second, and optionally third polynucleotide can be integrated separately into expression vectors, e.g. transient expression vectors or vectors which integrate into the genome of the cell. Alternatively, said first, second, and optionally third polynucleotide can be comprised on one expression vector. The expression may be driven from one promoter, two promoters, or three promoters. In the former case it is preferred that the proteins encoded by the first, second, and optionally third polynucleotide are transcribed as a single transcript and are only separated by an IRES.

In a preferred embodiment of the invention, the expression unit comprises one or more vertebrate expression control sequences operatively linked to a first polynucleotide comprising a nucleic acid sequence encoding the enzyme RMD, one or more vertebrate expression control sequences operatively linked to a second polynucleotide comprising a nucleic acid sequence encoding a glycosyltransferase for GDP-D-rhamnose, and optionally one or more vertebrate expression control sequences operatively linked to a third polynucleotide comprising a nucleic acid sequence encoding a GDP-deoxyhexose sugar nucleotide transporter for GDP-D-rhamnose, preferably comprised on one expression vector, on two expression vectors, or on three expression vectors, respectively.

In another preferred embodiment of the invention, the expression unit comprises one or more vertebrate expression control sequences which control the expression of the nucleic acid sequence encoding the enzyme RMD comprised within a first polynucleotide, the nucleic acid sequence encoding a glycosyltransferase for GDP-D-rhamnose comprised within a second polynucleotide, and optionally the nucleic acid sequence encoding a GDP-deoxyhexose sugar nucleotide transporter for GDP-D-rhamnose within a third polynucleotide, wherein the first, second, and optionally third polynucleotide are separated from each other by an IRES, preferably comprised on an expression vector.

The expression unit according to the seventh aspect of the invention can also be used in medicine, in particular in the preparation of a vaccine for therapy or prophylaxis of diseases benefiting from immune stimulation, in particular tumors.

Additionally, in the context of the seventh aspect all further preferred and particularly preferred embodiments of the first aspect of the invention, in particular relating to the polynucleotides comprising various nucleic acids to be expressed, expression control elements, e.g. driving moderate or low expression of the enzyme which uses GDP-6-deoxy-D-lyxo-4-hexulose, are equally preferred in the context of the seventh aspect.

In many cases, considerable time has been used and huge effort has been made by biopharmaceutical companies to generate and develop effective pharmaceutical producer cell lines that express the transgene of interest at desirable levels. In cases where the transgene of interest is a therapeutic antibody that could benefit from enhanced ADCC effector function, it is highly desirable to further manipulate the producer cell line in such a way that the high producer cell is incapable of attaching core-fucose to the N-glycomoieties or is capable of attaching artificial sugars to the N-glycomoieties.

Preferably, as already mentioned above, the expression unit further comprises a second polynucleotide which comprises a nucleic acid sequence encoding a glycosyltransferase for GDP-D-rhamnose, GDP-D-perosamine, GDP-deoxy-D-talose, GDP-6-deoxy-D-altrose, GDP-4-keto-3,6-dideoxy-D-mannose, or GDP-L-colitose, and optionally a third polynucleotide which comprises a nucleic acid sequence encoding a GDP-deoxyhexose sugar nucleotide transporter for GDP-D-rhamnose, GDP-D-perosamine, GDP-deoxy-D-talose, GDP-6-deoxy-D-altrose, GDP-4-keto-3,6-dideoxy-D-mannose, or GDP-L-colitose. It is preferred that the second polynucleotide which comprises a nucleic acid sequence encoding a glycosyltransferase for GDP-D-rhamnose, GDP-D-perosamine, GDP-deoxy-D-talose, GDP-6-deoxy-D-altrose, GDP-4-keto-3,6-dideoxy-D-mannose, or GDP-L-colitose is operably linked to one or more vertebrate expression control sequences to allow the expression of the nucleic acid sequence encoding said glycosyltransferase in the vertebrate cell, e.g. HeLa or CHO cell. It is also preferred that the third polynucleotide which comprises a nucleic acid sequence encoding a GDP-deoxyhexose sugar nucleotide transporter for GDP-D-rhamnose, GDP-D-perosamine, GDP-deoxy-D-talose, GDP-6-deoxy-D-altrose, GDP-4-keto-3,6-dideoxy-D-mannose, or GDP-L-colitose is operably linked to one or more vertebrate expression control sequences to allow the expression of the nucleic acid sequence encoding said GDP-deoxyhexose sugar nucleotide transporter in the vertebrate cell, e.g. HeLa or CHO cell.

The ratio of the expression of the different nucleic acid sequences to each other depends both on the copy number and on the site of integration in the genome of the vertebrate cell. By means of standard screening processes, it is possible to isolate cell clones which express the individual gene products in the desired ratio.

Said preferred expression unit can easily be applied to already existing cell lines (e.g. CHO, HeLa) in a way that renders them capable to attach other artificial sugars than fucose (e.g. D-rhamnose, D-perosamine, deoxy-D-talose, or 6-deoxy-D-altrose) to nascent glycostructures of glycoproteins or glycolipids. This expression unit can also easily be applied to already genetically engineered cell lines (e.g. CHO IgG1) in a way that renders them capable to attach other artificial sugars than fucose (e.g. D-rhamnose) to nascent glycostructures of glycoproteins, e.g. in order to produce antibodies having an artificial glycosylation structure, such as IgG1/+D-rhamnose.

Preferably, the expression unit comprises a further polynucleotide (either as a second, third, or fourth polynucleotide) which comprises a nucleic acid sequence encoding a protein of interest, e.g. IgG1. It is preferred that the further polynucleotide, which comprises a nucleic acid encoding a protein of interest, e.g. IgG1, is operably linked to expression control sequences allowing the expression of the nucleic acid sequence encoding said protein in a vertebrate cell, e.g. HeLa or CHO cell.

In the context of the expression unit of the sevenths aspect of the present invention all elements, preferably enzyme coding nucleic acids, expression control elements, nucleic acid sequence encoding an enzyme, which uses GDP-6-deoxy-D-lyxo-4-hexulose as a substrate and wherein the enzyme does not catalyze the reaction which converts GDP-6-deoxy-D-lyxo-4-hexulose into GDP-L-fucose, taught in the first and second aspect of the invention are similarly preferred.

In an eights aspect, the present invention relates to an (modified) eukaryotic cell for producing a protein, which normally comprises fucose on its glycomoieties, lacking fucose or having a reduced amount of fucose on its glycomoieties comprising:
 i) a first polynucleotide which comprises a nucleic acid sequence encoding an enzyme which uses GDP-6-deoxy-D-lyxo-4-hexulose as a substrate, and
 ii) a second polynucleotide which comprises a nucleic acid sequence encoding a protein,
wherein the enzyme does not catalyze the reaction which converts GDP-6-deoxy-D-lyxo-4-hexulose into GDP-L-fucose.

In the context of the eukaryotic cell all preferred and particularly preferred embodiments previously described in the context of the vertebrate cell of the first aspect of the invention are similarly preferred.

Preferably, the eukaryotic cell is a vertebrate, e.g. mammalian, a fish, an amphibian, a reptilian cell or an avian cell, preferably as outlined above with respect of the first aspect of the invention, or an insect cell. Insect cells, e.g. Sf9 or Hi5 cells, used in conjunction with the baculovirus expression system are preferred for producing glycoproteins because of high yields and speed. However, glycoproteins from insect cells may contain core alpha 1,3-fucose. The sugar residue contributes to a major extend to antibodies against insect derived glycoproteins, in particular IgE antibodies. They are the basis of allergic reactions to insect glycoproteins.

Insect cells comprising at least one enzyme which uses GDP-6-deoxy-D-lyxo-4-hexulose as a substrate, wherein the enzyme does not catalyze the reaction which converts GDP-6-deoxy-D-lyxo-4-hexulose into GDP-L-fucose will lack fucose or have reduced fucose on its glycans. This will reduce or eliminate allergic reactions to such glyoproteins.

The above mentioned (modified) eukaryotic cell may also comprise more than one polynucleotide which comprises a nucleic acid sequence encoding an enzyme which uses GDP-6-deoxy-D-lyxo-4-hexulose as a substrate, e.g. polynucleotides which comprise nucleic acid sequences encoding different enzymes which use GDP-6-deoxy-D-lyxo-4-hexulose as a substrate (see first aspect of the present invention).

In a ninth aspect, the present invention relates to a method for producing a protein, which normally comprises fucose on its glycomoieties, lacking fucose or with a reduced amount of fucose on its glycomoieties comprising the steps of:
 i) providing an eukaryotic cell according to the eights aspect,
 ii) expressing the enzyme encoded by the first polynucleotide and the protein encoded by the second polynucleotide in said cell, and
 iii) isolating the protein from said cell.

In the context of the method using the eukaryotic cell of the present invention all preferred and particularly preferred embodiments previously described in the context of the vertebrate cell of the first aspect of the invention and the method of the second aspect of the present invention are similarly preferred in the context of the ninth aspect of the invention.

In a tenth aspect the present invention relates to a proteins lacking fucose of having a reduced amount of fucose on its glycomoieties obtainable by the method of the ninth aspect.

Various modifications and variations of the invention will be apparent to those skilled in the art without departing from the scope of invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art in the relevant fields are intended to be covered by the present invention.

The following figures and examples are merely illustrative of the present invention and should not be construed to limit the scope of the invention as indicated by the appended claims in any way.

EXAMPLES

1. Experimental Part
1.1 Materials and Methods
1.1.1 Cell Lines

The recombinant CHO/DG44 cell line CHO-IgG was established earlier in our laboratory by stable transfection of the dihydrofolate reductase-deficient CHO cell line, CHO/DG44 (Urlaub et al., 1986, Proc Natl Acad Sci USA. 83 (2): 337-341) with an expression vector containing an antibody expression cassette comprising nucleotide sequences encoding light and heavy chain of a therapeutic monoclonal antibody (Trastuzumab (Herceptin®)). Generation of the cell line RMD-CHO-IgG started from the existing CHO-IgG cell line. Both cell lines were maintained in serum-free medium

1.1.2 Gene Optimization and Synthesis

The amino acid sequence for the oxidoreductase Rmd (Pseudomonas aeruginosa PAO1; 304 amino acids) (GenBank Accession No. GenBank: AAG08839.1) was reverse translated and the resulting nucleotide sequence optimized by knockout of cryptic splice sites and RNA destabilizing sequence elements, optimisation for increased RNA stability and adaptation of codon usage to match the requirements of CHO cells (Cricetulus griseus).

1.1.3 Construction of the RMD Expression Plasmid

The synthesized RMD-construct was cut with EcoRI and Bgl II and dephoshorylated with calf intestinal phosphatase. The digested and dephosphorylated insert was ligated into a pre-digested bicistronic expression vector which allows coordinated co-expression of RMD and green fluorescent protein from a bicistronic message (gfp). The expression plasmid is equipped with a Neomycin resistance gene allowing for direct selection of cells that have stably integrated the bicistronic expression cassette. General procedures for constructing expression plasmids are described in Sambrook, J., E. F. Fritsch and T. Maniatis: Cloning I/II/III, A Laboratory Manual New York/Cold Spring Harbor Laboratory Press, 1989, Second Edition.

Figure 2:
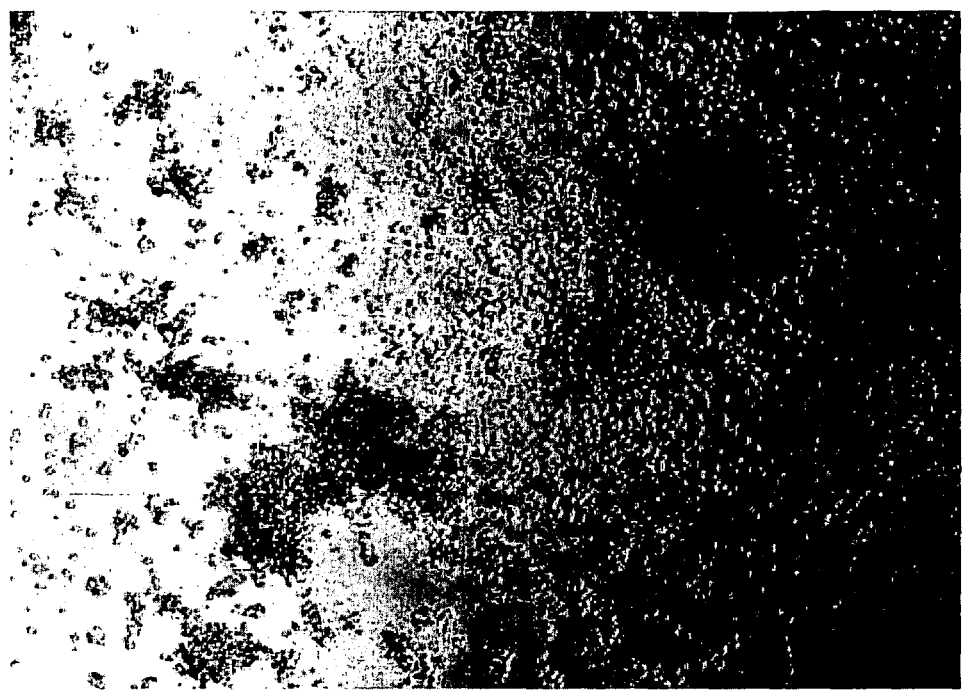
FIG. 2 shows GFP-fluorescence of RMD-CHO-IgG cells that stably overexpress the RMD transgene.
Figure 2:

1.1.4 Conversion of Antibody-Producing CHO-IgG Cells into Cells Secreting Non-Fucosylated Antibodies CHO-IgG cells stably expressing the IgG1-type therapeutic antibody Trastuzumab were stably transfected with the RMD-gfp transgene by electroporation according to the manufacturer's instructions (MicroPorator, PEQLAB Biotech, Germany). 24 h after electroporation transfectants were selected in alpha-MEM containing the antibiotic G418. The G418-resistant clones were then isolated by limiting dilution cloning, i.e. they were resuspended in this selective medium and seeded into 96 well plates at dilutions where the likelihood of obtaining a colony from a single cell is greater 95% based on poisson statistics. To assure monoclonality, cells grown within the 96 wells were isolated and again seeded into 96 well plates at limiting dilution. After these two rounds of single cell cloning, a couple of the isolated single cell clones were expanded into larger volumes. Afterwards, they were adapted to growth in suspension. Using the described electroporation protocol a transformation efficiency of approximately 2000 per $2\times10^6$ electroporated cells was achieved as assessed from gfp-fluorescence distribution in the culture dishes (FIG. 2).

1.1.5 Clone Screening by Fluorescence Microscopy

Figure 3:
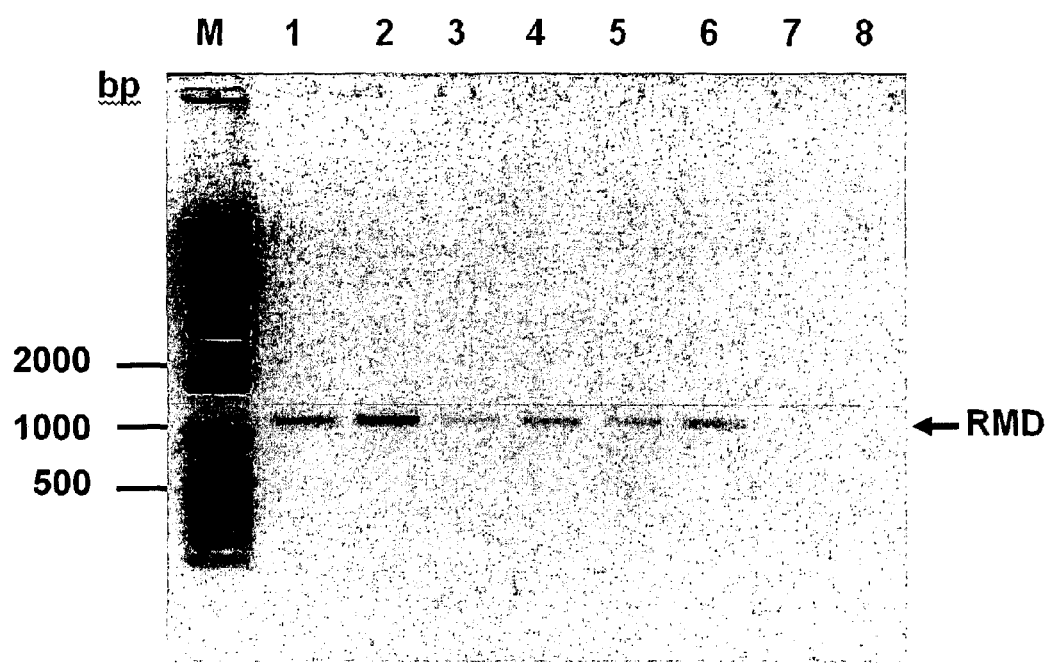
FIG. 3 shows a RT-PCR analysis of clones expressing the RMD-Transgene. Lane M=bp-DNA-Marker, Lane 1: RMD-CHO-IgG clone 1; Lane 2: RMD-CHO-IgG clone 2; Lane 3: RMD-CHO-IgG clone 3; Lane 4: RMD-CHO-IgG clone 4; Lane 5: RMD-CHO-IgG clone 5; Lane 6: RMD-CHO-IgG clone 6; Lane 7: CHO-IgG parental clone; Lane 8: negative PCR control. The RMD band is visible in all RMD-tranfected clones.

Single cell clones were seeded into 96 well plates and screened for successful RMD-integration by monitoring of GFP-fluorescence with an Olympus IX-50 (Olympus Optical Co., Europe) fitted with a cmount adapter. For GFP-scan a fluorescence-filter at 200-fold extension was used versus phase contrast. Images were edited by Viewfinder lite application. Additionally, mRNA expression of the RMD transgene was confirmed by RT-PCR analysis. Successful expression of the RMD transgene was confirmed by RT-PCR using an RMD-specific set of primers (FIG. 3).

1.1.6 Production of Unmodified and Glycoengineered IgG1 by Serum Free Batch Culture in Shaker Tubes In order to compare the glycostructures of antibodies produced by RMD-modified CHO producer clones (RMD-CHO-IgG) with the glycostructure of IgG1-type antibodies secreted from unmodified CHO antibody producer cells (CHO-IgG), both cell lines were used to produce IgG1 antibodies in the culture supernatant. RMD-CHO-IgG and CHO-IgG antibody producer clones were inoculated at $2\times10^5$ cells/ml in a fucose-deficient growth medium. The shaker tubes were incubated at 180 rpm, 37° C., 7.5% pCO2. The culture was stopped after 7 days when the cells still showed a vitality >80%. Viable cell density was measured with an automatic cell counter, Vi-CELL™ XR (Beckman Coulter, Fullerton, Calif.), using trypan blue exclusion. The pattern of declining viability over the duration of the fed batch assay as well as the average specific productivity (qp) between days 3 and 10 of the Fed batch shaker assay remained comparable between the two different clones. Cells were then pelleted by centrifugation for 10 at 5000 rpm and the supernatant was transferred into a separate vial. RMD-CHO IgG and unmodified CHOIgG cells were cultured alike. The antibody concentration in the culture supernatants was measured on the Gyrolab Workstation (Gyros AB, Sweden) by a Sandwich Immuno Assay specific for human IgG1. Both clones grew logarithmically, yielded comparative IgG-titers at the respective sampling dates and had a comparative initial doubling time. Both clones retained the morphology typical of Chinese Hamster Ovary cells.

1.1.7 Purification of IgG1 by Protein A Affinity Chromatography

Following sterile filtration by 0.2 μm filter, the supernatant was loaded onto a Protein-A-Sepharose mini column. 0.5 ml column support material with a total capacity of 10 mg were used. The column was equilibrated with 5 column volumes of 20 mM sodium phosphate, pH 7.0 at gravity flow. After protein binding at a slow flow rate, the column was washed twice with the equilibration buffer. Then the antibody was eluted with 4 column volumes 0.1 M glycine buffer, pH 3.0 at gravity flow. Fractions of 1 ml were collected and immediately neutralized with 1 M Tris-HCl, pH 9. Integrity and purity of each purified IgG1 was confirmed by reducing SDS-PAGE analysis. The purity was >90% and integrity of the eluted antibodies were confirmed by reducing SDS-PAGE analysis.

1.1.8 Preparation of Antibody Derived N-linked Oligosaccharides

100 μg of each antibody were used for mass spectrometric characterization of N-linked oligosaccharides. Proteins were digested with trypsin (0:2 mg/ml, 16 h, 37° C.) before the N-Glycanes were released by incubation with 1 unit of peptide-N-glycosidase F (PNGaseF, Roche Diagnostics) for 18 h at 37° C. Released N-glycans were recovered by two-step chromatography on RP-(Sep-Pak C18-) columns followed by carbograph extract-clean columns (Wuhrer et al., 2006, Glycobiology 16 (2006), pp. 991-1006). 50% of each N-glycan pool was digested with 10 mU Neuraminidase 18 h at 37° C. and 50% were permethylated with methyl iodide as described by Ciucanu and Kerek (Ciucanu and Kerek, 1984, Carbohydr Res. 1984: 131:209).

1.1.9 Analysis of N-linked Oligosaccharides by MALDI-TOF-MS

Figure 4:
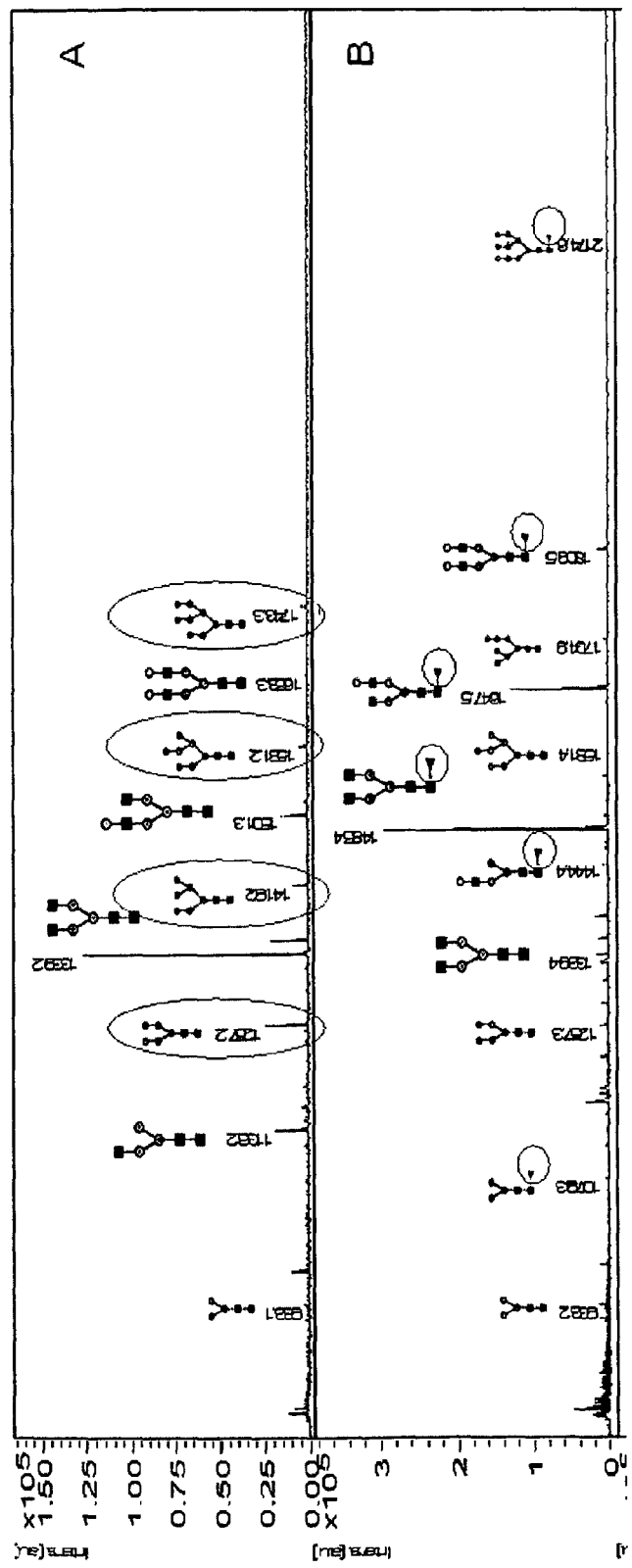
FIG. 4 shows a synoptic comparison of MALDI MS profiles of permethylated N-glycans released from IgG1 of CHO-IgG (B) and RMD-CHO-IgG (A) cells. Antibody Fc oligosaccharides released by PNGase F digestion were analyzed using an UltraFlex III TOF/TOF mass spectrometer equipped with a smartbeam-II™ laser. The m/z value peaks correspond to the sodium-associated oligosaccharide ion. All labelled [M+Na]+ molecular ion signals could be assigned as annotated. A 164 Da shift of the major m/z-peaks in the MALDI-spectrum shown in panel A is indicative of the loss of Fucose. The schematic oligosaccharide structure of each peak is illustrated above each annotated peak. The N-Glycostructures obtained from a therapeutic IgG1 antibody expressed in RMD-CHO-IgG cells that stably overexpresses the RMD transgene are completely void of attached Fucose-Residues and contain a comparatively larger amount of high mannose structures based on MALDI-Peak relative intensities (Panel A; prominent High Mannose structures encircled) while the N-Glycostructures obtained from a therapeutic IgG1 antibody expressed in the unmodified CHO-IgG parental cells are core-fucosylated and contain significantly lower amounts of high mannose structures. (Fucose residues=black triangles encircled; Panel B).

N-glycans released from each purified IgG1 were analyzed by an UltraFlex III TOF/TOF mass spectrometer (Bruker Daltonik GmbH, Bremen, Germany) equipped with a smartbeam-II™ laser. Measurements were carried out in the positive ion mode. Positive ions were subjected to an accelerating voltage of 25 kV and an extraction delay of 10 ns and analysed in a reflectron mode. For analysis, the desialylated glycans were dissolved in $H_2O$ and the permethylated glycans were dissolved in 70% (v/v) acetonitrile. 0.5 μl samples were mixed 1:1 (v/v) with Arabinosazone (2 mg/ml) dissolved in 80% EtOH on a target and left to dry at room temperature. An external calibration with a dextran ladder was used. Spectra were analyzed using Glyco-peakfinder (Maas et al., 2007, Proteomics 7, 4435-4444). Identified glycan structures were built with the GlycoWorkbench software (Ceroni et al., 2008, J. Proteome Res. 7(4) 1650-1659). The oligosaccharide profile analysis of products purified from the final culture medium confirmed that the N-linked Fc oligosaccharides of the products were of the high-mannose as well as of the biantennary complex type, and that the IgG1 product secreted from the RMD-CHO-IgG clone fully lacked core fucosylation. Glycostructure analysis showed that the ratio of non-fucosylated oligosaccharides of the antibodies produced by the RMD co-expressing clones had increased significantly in each case (i.e., up to 99%, 95%, 97%, and 98%), compared to those of the parental CHO-IgG clones (FIG. 4). The N-Glycostructures obtained from the IgG1 antibody product expressed in RMD-CHO-IgG cells are almost completely void of attached Fucose-Residues and contain a comparatively larger amount of high mannose structures based on MALDI-Peak relative intensities (FIG. 4, Panel A; prominent High Mannose structures encircled), while the NGlycostructures obtained from a therapeutic IgG1 antibody expressed in unmodified CHO-IgG cells are core-fucosylated and contain significantly lower amounts of high mannose structures (Fucose residues=triangles encircled; FIG. 4, Panel B).

2. Experimental Part 2.2 Materials and Methods 2.2.1 Cell Lines, Gene Optimization and Synthesis, Construction of the RMD Expression Plasmid, Conversion of Antibody-Producing CHO-IgG Cells into Cells Secreting Non-Fucosylated Antibodies, Clone Screening by Fluorescence Microscopy and RT-PCR As to the CHO-IgG cell line used in order to produce the RMD-CHO-IgG cell line, the gene optimization and synthesis of RMD, the construction of the RMD expression plasmid, the conversion of antibody-producing CHO-IgG cells into cells secreting non-fucosylated antibodies, the clone screening by fluorescence microscopy for successful RMD-integration and the RT-PCR for successful mRNA expression of the RMD transgene, it is referred to items 1.1.1 to 1.1.5 as mentioned above (1. Experimental part).

2.2.2 Fed-Batch Culture

IgG were produced using both CHO and RMD-CHO cells (clones H1, H2 and H3) in order to compare their N-glycan structures. Cells were seeded at $4 \times 10^5$ cells/ml into 500 ml shake flasks in 100 ml of serum-free medium (custom formulation for ProBioGen; SAFC Bioscience, Lenexa, Kans.) supplemented with 4 mM glutamine but without antibiotics or MTX. Cultures were agitated at 180 rpm in 37° C. and 7.5% $CO_2$. Cells were fed with 1.75 ml of PBG-Feed Mix per 100 ml culture volume on culture day 4. Cell density and viability were determined by trypan-blue exclusion using an automated ViCell cell quantification system (Beckman Coulter, Brea, Calif.). Aliquots of cell culture supernatant were collected on days 3, 5 and 7 in order to determine IgG concentrations, which were measured by Gyrolab sandwich immuno assay. The culture was stopped after 7 days when cells still showed vitality higher than 80%. The cell culture supernatant was collected and sterile-filtered.

2.2.3 IgG1 Specific Gyrolab Sandwich Immuno Assay

IgG1 concentration was determined by a sandwich immuno assay performed on a Gyrolab Workstation (Gyros AB, Uppsala, Sweden). The assay included sequential addition of biotinylated capture antibody, which recognizes epitopes on the Fc-part of IgG, cell culture supernatant samples or polyclonal human IgG reference standard and an Alexa Fluor 647-labelled detection antibody, which binds epitopes in the Fab domain of IgG. Samples and standards were measured in triplicate. The mean OD, standard deviation (SD), and % coefficient of variation (% CV) were calculated automatically by the Gyrolab evaluator software after each run. The described IgG1 Gyrolab sandwich immuno assay was pre-validated based on the premise that the residuals for each calibration standard meet an acceptance limit of 20% relative error (RE).

2.2.4 IgG Purification Using Protein A Affinity Chromatography

The cell culture supernatant was loaded on a 0.5 ml Protein A-Sepharose column, pre-equilibrated with 20 mM sodium phosphate, pH 7.0. After washing the column with two bed volumes of equilibration buffer, the antibody was eluted with 4-column volumes 0.1 M glycine pH 3.0. Fractions were collected and immediately neutralized with 1 M Tris-HCl, pH 9. Integrity and purity of each purified IgG was confirmed by reducing SDS-PAGE analysis. The protein concentration of the purified IgG was determined by Gyrolab sandwich immuno assay.

2.2.5 Processing of IgG N-Glycans

IgGs (100 µg) were digested with trypsin for 16 h at 37° C. The reaction was terminated by heating the sample for 5 min at 95° C. Antibodies were further digested with 1 U PNGase F for 18 h at 37° C. Released N-glycans were isolated and desalted on reverse-phase Sep-Pak $C_{18}$ cartridges followed by carbograph extract-clean columns. Each N-glycan pool was digested with 10 mU Neuraminidase for 18 h at 37° C.

2.2.6 Mass Spectrometry

N-glycans were analyzed on an UltraFlex III TOF/TOF mass spectrometer (Bruker Daltonik GmbH, Bremen, Germany) equipped with a smartbeam-II™ laser and a LIFT-MS/MS facility. Spectra were recorded in a reflector mode at an accelerating voltage of 25 kV and an extraction delay of 10 ns. Measurements were carried out in the positive-ion mode. External calibration was performed using a dextran ladder. Desialylated N-glycans were dissolved in $H_2O$. 0.5 µl samples were mixed 1:1 (v/v) with D-arabinosazone (5 mg/ml) dissolved in 70% aqueous ethanol on a steel target (Chen et al. 1997). Spectra were analyzed using Glyco-Peakfinder [Maas et al., 2007]. Identified glycan structures were built with the GlycoWorkbench software [Ceroni et al., 2008].

2.2.7 Fc-Gamma Receptor IIIA (FcγRIIIA) Specific Binding Assay

The FcγRIIIA-binding activity of the IgG samples was analyzed by an FcγRIIIA specific binding assay as described by Niwa et al., 2004 with slight modifications. A histidine (HIS)-tagged FcγRIIIA (F158) (22 kDa; 158F; R&D Systems, Minneapolis, Minn.) was used in combination with an anti-tetraHIS monoclonal antibody (Qiagen, Hilden, Germany) for receptor binding. Immunoplates (Maxisorp, Thermo, Waltham, Mass.) were coated with anti-tetraHIS antibody and blocked with blocking reagent (Roche Diagnostics, Penzberg, Germany). Subsequently, recombinant HIS-tagged FcγRIIIA was added to the immunoplates. Coated plates were then incubated with serial sample dilutions and controls so that they could bind the immobilized FcγRIIIA receptor. After a wash step, bound IgGs were detected by an anti-human IgG peroxidase-conjugated mAb (Dianova, Hamburg, Germany) and the amount of bound IgG was quantified via peroxidase activity. After each incubation step the immunoplate was washed 3 times with PBS containing 0.2% Tween-20. Tetramethylbenzidine (TMB; Seramun, Heidesee, Germany) was used as a chromogenic substrate, the reaction was terminated using 1 M sulfuric acid and finally, absorption was detected at 450 nm (Infinite F200 Reader, Tecan, Crailsheim, Germany). Based on the concentration dependent absorption data, full curve fits were conducted using a 4-parameter logistic curve model (Magellan Software 6.1, Tecan). The intra-serial precision for this FcγRIIIA binding assay was determined to be within 15% CV.

2.2.8 Antibody-Dependent Cellular Cytotoxicity (ADCC) Assay

Primary human NK cells were isolated from peripheral blood mononuclear cells (PBMCs). PBMCs were separated from whole blood of healthy human donors by density gradient centrifugation and NK cells were subsequently isolated by negative magnetic bead separation (Miltenyi, Bergisch Gladbach, Germany). The purity of the isolated NK cells was confirmed by flow cytometry (PE-conjugated CD16 and Alexa488-conjugated CD56 antibodies, BD, San Jose, Calif.). The cell lines BT-474 (Lasfargues et al., 1978, invasive ductal carcinoma of the breast, human, CLS, Eppelheim, Germany) and SK-BR-3 (Zabrecky et al., 1991, adenocarcinoma of the breast, human, ATCC, Manassas, Va.) were used as target cells. Both cell lines were confirmed positive for the Her2/neu marker by flow cytometry (data not shown). The target cell lines were revitalised from a research cell bank 3 days prior to inoculation. Antibody-dependent NK cell induced target cell lysis was quantified by release of a vital stain (Calcein A M, Life Technologies, Carlsbad, Calif.). Target cells were stained according to the manufacturers protocol and seeded at $2\times10^4$ viable cells/well in 50 μL RPMI1640 (Life Technologies) +10% FCS (Biochrom, Berlin, Germany) in 96-well micro titer plates. Serial 1:3 dilutions of antibodies in RPMI1640+10% FCS were prepared. 50 μL/well of each dilution was pipetted with n=3 and pre-incubated with the target cells for 30 min at 37° C. prior to NK cell inoculation. At the end of the antibody pre-incubation, effector cells were seeded at an effector to target cell ratio (E:T) of 5:1. The plates were subsequently centrifuged at 200 g for 3 min and incubated for 4 h at 37° C. and 5% $CO_2$. For each cell line, a spontaneous target cell lysis control (w/o NK cells), an antibody-independent target cell lysis control (w/NK cells) and a total target cell lysis control (induced by saponin) were induced. The total lysis in the control wells was induced by adding 15 μL/well 0.1 mg/mL saponin in RPMI1640+10% FCS 15 min before the end of the incubation period. In all other wells, 15 μLRPMI1640+10% FCS were added. The release of calcein AM was quantified by fluorescence detection in the culture supernatant. The plates were centrifuged (150 g; 3 min) and 100-μL supernatant from each well were transferred into a 96-well black fluorescence plate (Thermo). The mean fluorescence intensity (MFI) was detected using an Infinite F200 reader (Tecan, 485/535 nm excitation/emission filter). Curve fitting was done using a 4-parameter logistic dose-response model (Magellan software version 6.1). The specific cell lysis was calculated as follows: Specific cell lysis [%]=[MFI (sample)−MFI (spontaneous)]/[MFI (total)−MFI (spontaneous)]×100. Whereas MFI (sample) is the mean fluorescence intensity released by specific target cell lysis, MFI (spontaneous) is the gradual release of the fluorescent dye by the target cells, and MFI (total) is mean fluorescence intensity obtained after detergent induced total target cell lysis.

2.2.9 Monosaccharide Analysis and Rhamnose Determination

Cells ($3\times10^7$) were separated from the supernatant by centrifugation at 100 g for 5 min. They were subsequently lysed by 3 freeze-thaw cycles. Cell membranes were then separated from cytosolic fractions at 21 000 g for 30 min at 4° C. Cell culture supernatants, cell membranes, cytosolic fractions as well as IgG N-glycans were hydrolyzed in 2 N TFA for 4 h at 100° C. After evaporation under reduced atmosphere, samples were analyzed by HPAEC-PAD on a PA-1 column using a Dionex ICS-3000 and 2-deoxyribose was used as the internal standard. Neutral monosaccharides were separated by isocratic elution with 2.25 mM NaOH. Postcolumn addition of 200 mM NaOH enabled amperometric detection. Since HPAEC-PAD does not allow assignment of enantiomeric identity (Horton, D. 2004), L-rhamnose was used as a standard to determine the retention time expected for D-rhamnose. The LOD for rhamnose was determined as described in Chapter 6.3 of the ICH harmonized tripartite guideline for validation of analytical procedures (ICHQ2 (R1)).

2.3 Results

2.3.1 Heterologous Expression of the RMD Transgene

To evaluate the effects of RMD-transgene expression on the levels of fucosylation of secreted IgG, a vector equipped with a bicistronic expression cassette comprising the genes for GDP-6-deoxy-D-lyxo-4-hexulose reductase (RMD) and green fluorescent protein (gfp) was generated and introduced into a CHO/DG44 clone that had previously been engineered for overexpression and secretion of a biosimilar version of the IgG1-type therapeutic antibody Trastuzumab (Herceptin®, Roche). G418-resistant clones expressing the transgene were identified by their gfp-mediated green fluorescence and appeared within 2 weeks of transfection. A transformation efficiency of approximately 80% was achieved by electroporation as assessed from gfp-fluorescence distribution (data not shown but comparable with data shown in FIG. 2). Successful expression of the RMD transgene was confirmed by RT-PCR using an RMD-specific set of primers (data not shown but comparable with data shown in FIG. 3). The modified CHO cells expressing the RMD transgene are named RMD-CHO.

2.3.2 Serum Free Fed-Batch Culture of CHO and RMD-CHO Antibody Producing Cells Serum-free fed-batch culture of the unmodified parental CHO and the transfected RMD-CHO cells producing IgG was carried out in 50 ml bioreactor tubes containing a fucose-deficient growth medium supplemented with L-glutamine. Bioreactor tubes were inoculated at a starting cell density of $4\times10^5$ cells/ml and then incubated at 180 rpm, 37° C., 7.5% $pCO_2$. Performance of the fed-batch cultures was monitored for 14 days and was compared side-by-side. Comparative analysis of parallel fed bach cultures of CHO and RMD-CHO cells showed no significant deviations over a course of 14 days. Initial doubling rates, proliferation rates and IgG-titers at the respective sampling dates were congruent for both cell lines. Both clones retained the morphology typical of CHO cells. The pattern of declining viability over the duration of the fed batch assay as well as the average specific productivity ($q_p$) between days 3 and 10 of the Fed batch shaker assay remained comparable for the two different clones (data not shown).

2.3.3 N-Glycan Analysis of IgG Produced from CHO and RMD-CHO Cells

Figure 5:
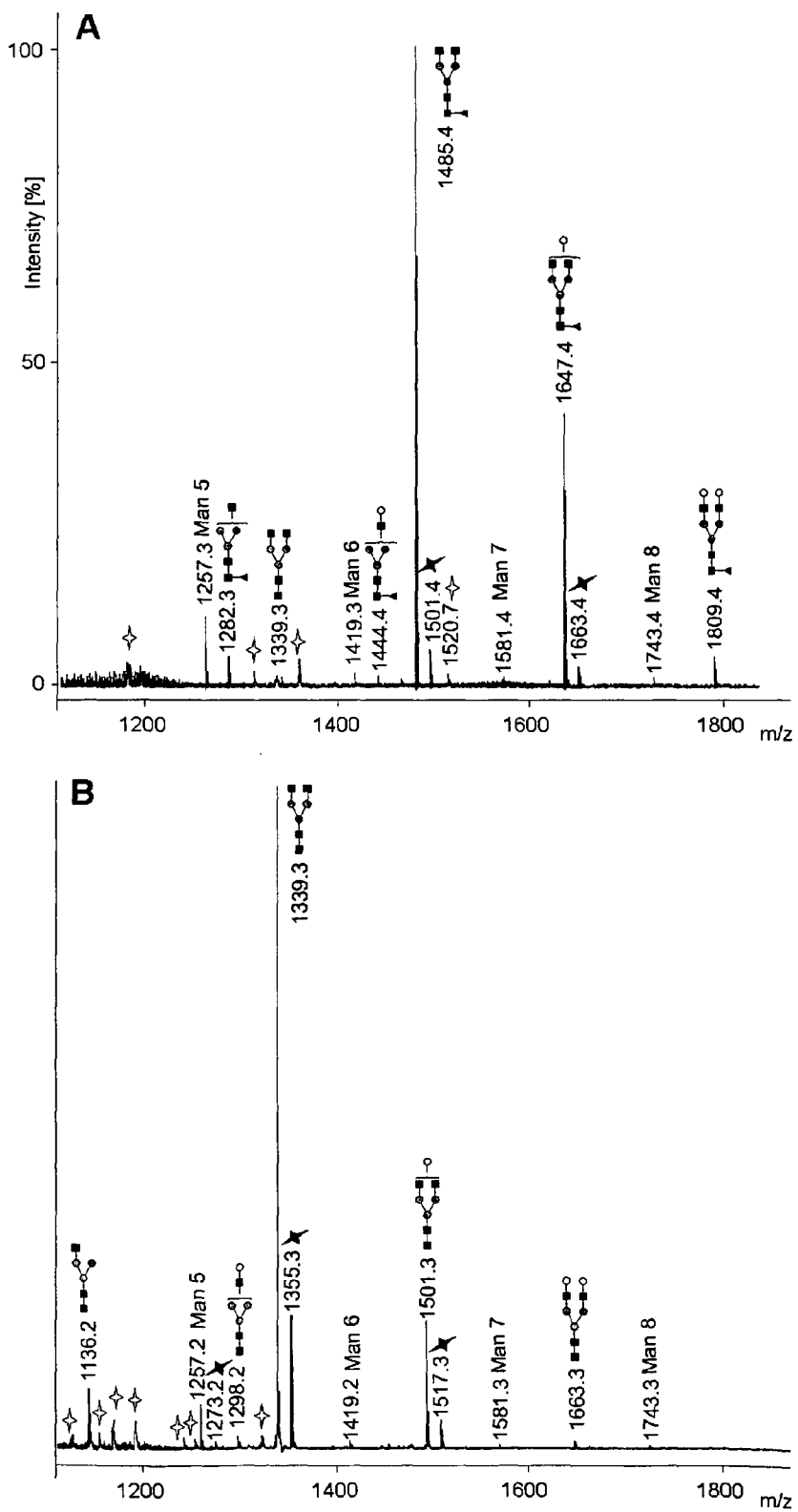
FIG. 5 shows a MALDI-TOF spectra of desialylated IgG N-glycans produced using (A) WT CHO cells; (B) RMD-CHO clone H1; (C) RMD-CHO clone H2; (D) RMD-CHO clone H3. All molecular ions are present in either sodiated [M+Na$^+$] or potassiated [M+K$^+$] form (black cross). Dark grey circle, Man; light grey circle, Gal; black square, GlcNAc; black triangle, Fuc; white cross, does not contain any carbohydrate material.

CHO and RMD-CHO cells were grown in a batch culture. Three different RMD-CHO clones producing IgG were used, namely H1, H2 and H3. Cells were inoculated at a starting cell density of $4\times10^5$ cells/mL and grown for 7 days in bioreactor tubes at 180 rpm, 37° C., 7.5% $pCO_2$. Supernatants were harvested on day 7 and IgG samples were purified by protein A affinity chromatography. Purity and integrity of the eluted antibodies were confirmed by reducing SDS-PAGE. N-glycans, released using PNGase F, were desialylated and subsequently analyzed by MALDI-TOF-MS. Relative quantification of signal intensities of N-glycans was performed as it was demonstrated earlier to give reliable results when compared to chromatographic methods (Wada et al., 2007). High-mannose as well as of complex-type diantennary N-glycan structures were detected in all the samples (FIG. 5). Monofucosylated agalactosylated/monogalactosylated/digalactosylated diantennary N-glycans were the three most abundant N-glycan structures found in wild type (WT) IgG (FIG. 5 A). The presence of core-fucose in those peaks, namely at m/z 1485.4, 1647.4 and 1809.4, was confirmed by MALDI-TOF/TOF. A diagnostic fragment ion dHex$_1$HexNAc$_2$ was observed in every spectrum at m/z 592.8. In the IgG samples that were produced from RMD-CHO cells, only trace amounts of fucose were observed (FIG. 5 B, C, D) representing a maximum of 2% of the total N-glycan pool (sample H2). Simultaneously, sample H2 contained a larger amount of high-mannose structures than WT IgG.

2.3.4 IgG1-Fc Binding Activity of IgG Produced from CHO and RMD-CHO Cells

Figure 6:
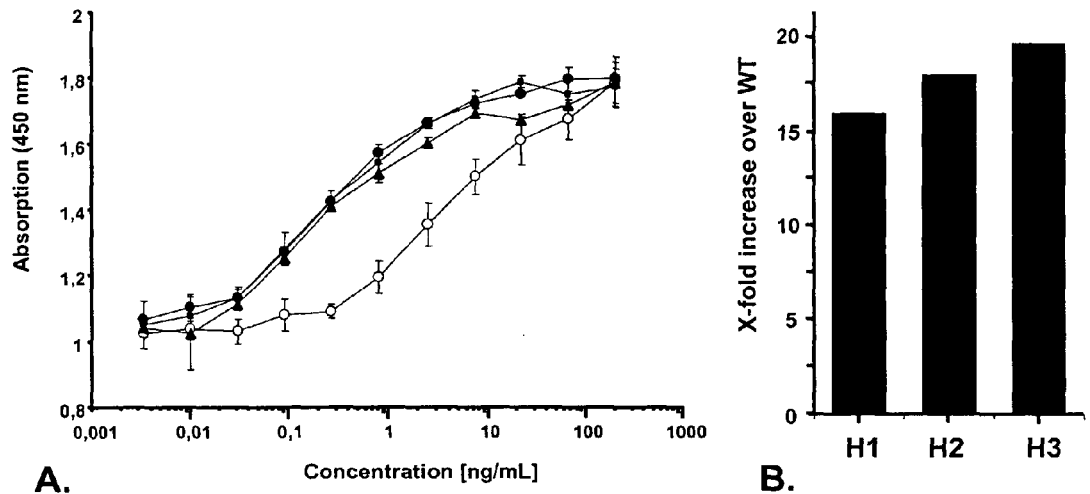
FIG. 6 shows in (A) binding curves of FcgRIIIa-His (Phe158) to WT IgG and afucosylated IgG in the absence of plasma. FcγRIIIa-binding was detected by an ELISA using FcγRIIIa-His as a capture reagent, anti-human IgG peroxidase-conjugated antibody as a detection reagent and Tetramethylbenzidine (TMB) as a chromogenic substrate. Points indicate the median absorption of peroxidase reacted TMB at 450 nm, n=2. Bars indicate SD. Open circles=wild type fucosylated IgG (WT), closed circles=afucosylated IgG derived from clone H1 (H1); closed squares=afucosylated IgG derived from clone H2 (H2); upward pointing closed triangles=afucosylation IgG derived from clone H3 (H3). It shows in (B) relative fold increase in FcγRIII-binding of afucosylated IgG over WT IgG. The relative fold increase in FcγRIII-binding was calculated from EC$_{50}$ values. WT, wild type fucosylated IgG; H1, afucosylated IgG derived from clone H1; H2, afucosylated IgG derived from clone H2; H3, afucosylated IgG derived from clone H3.

Since the comparatively weak interaction ($K_d$~1 μM) between IgG1 and its cognate Fc receptor FcγRIIIa is one of the major factors that contribute to the ADCC effector function (Sondermann et al., 2000), an FcγRIIIa binding assay is an indirect measure to predict ADCC activity of IgG1 monoclonal antibody samples. FcγRIIIa binding of afucosylated IgG secreted from RMD-CHO cells was greatly increased with equivalent binding at ~16-fold less protein to FcγRIIIa-158F when compared with fucosylated IgG secreted from the wild type CHO cells (FIG. 6 A, B). The data are reported in FIG. 6 B as relative fold-increase in binding of afucosylated IgG using the fucosylated IgG as a reference.

2.3.5 ADCC Activity of Afucosylated IgG Produced Using RMD-CHO Cells

Figure 7:
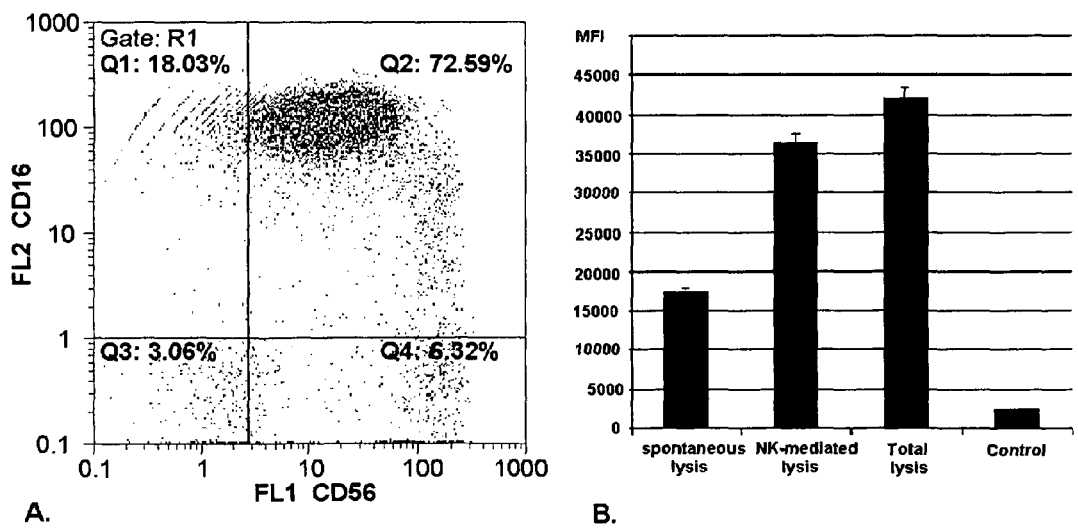
FIG. 7 shows the preparation and analysis of NK-Cells for ADCC-activity assays. (A) Dot Plot showing the level of purity of the isolated primary NK cells used in the ADCC assays. Primary NK-cells were isolated from whole blood from a healthy human donor by magnetic bead separation. The isolated NK cells were then analyzed for purity by flow cytometry using antibodies against the NK-cell markers CD 16 and CD56. (B) Performance of the isolated NK cells. In order to determine the cytolytic activity of the isolated NK cells, the calcein AM stained K562 target cells were incubated either alone, with NK-cells or with the cell lysing agent saponin for 4 hrs. Mean fluorescence intensity (MFI) released from the incubated target cells indirectly indicates the extent of cell lysis. The MFI observed for NK-mediated cell lysis subtracted from the MFI obtained for spontaneous cell lysis indicates the maximum possible specific MFI to be observed in the ADCC assay. Note that NK-mediated lysis does not completely reach the MFI-level obtained from total lysis.
Figure 8:
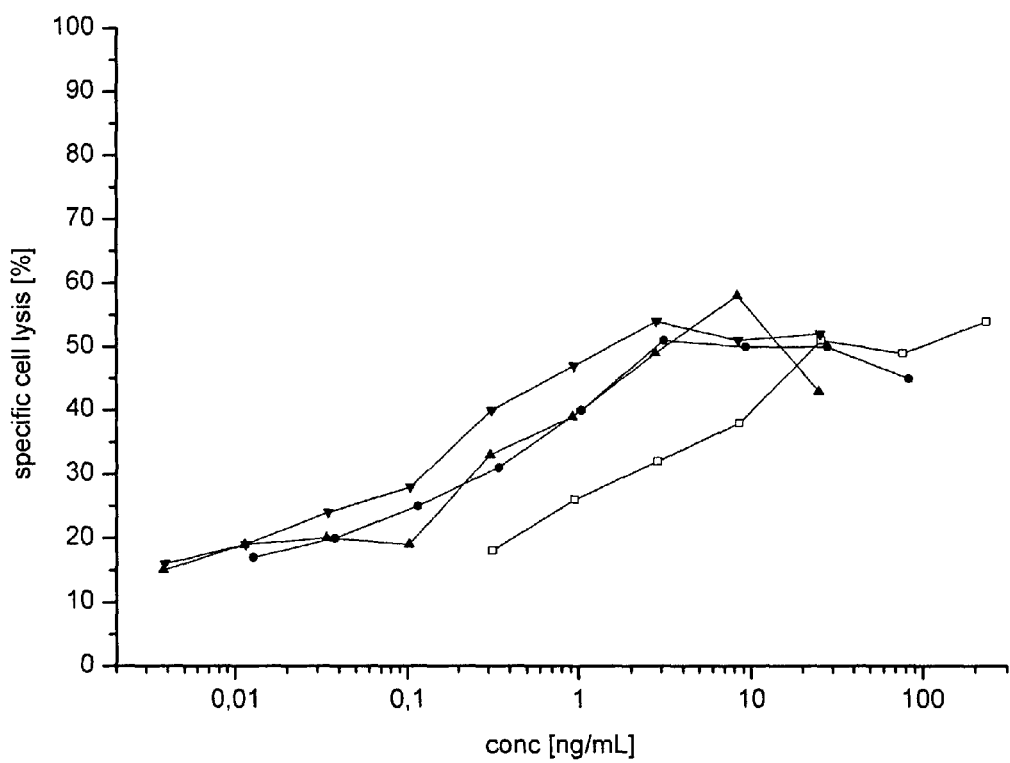
FIG. 8 shows in vitro ADCC-activity of afucosylated and fucosylated IgG derived from CHO and RMD-CHO. Points indicate mean specific cell lysis (%) at a given IgG concentration (%), n=4; bars indicate +/−SD, Wild Type IgG (open squares), afucosylated IgG derived from clone H1 (closed circles), afucosylated IgG derived from clone H2 (downward pointing closed triangle) and afucosylated IgG derived from clone H3 (upward pointing closed triangle). Comparable data were obtained when SK-BR-3 cells were used as target cells (data not shown).

To analyze ADCC activity, isolated NK-cells and HER2-expressing target cells were co-incubated with serial dilutions of afucosylated and fucosylated IgG. As a prerequisite for the assay, NK cells were isolated from whole blood samples at a purity level of 73% (FIG. 7). The technical NK cellular cytotoxicity control showed a specific lysis activity of 77% for the donor material used for the ADCC-assay (FIG. 7). The HER2-expressing target cell line BT-474 (isolated from a human, invasive ductal carcinoma of the breast) was used in the ADCC assay. The BT-474 target cell line is also attacked by NK cells by mechanisms other than ADCC. BT-474 cells show a mean value of 16% antibody-independent cell lysis (data not shown). Data for specific cell lysis induced by IgG samples are displayed in FIG. 8. All three afucosylated IgG samples (H1-H3) induced an increased ADCC-response compared to the WT antibody (FIG. 8). The afucosylated IgG sample H2 induced the highest ADCC-response (FIG. 8). Similar results were obtained when SK-BR-3 cells (HER2 positive adenocarcinoma of the breast) were used as target cells in the assay. The calculated EC$_{50}$ values for afucosylated and fucosylated IgG samples incubated with BT-474 and SK-BR-3 cells are summarized in Table 2 (see below). The observed shift in EC$_{50}$ between wild type IgG and the variants H1 to H3 remained comparable regardless of the target cell line used in the ADCC assay (FIG. 8). In the presence of the HER2-positive BT474 and SK-BR-3 target cell lines and purified NK-cells, afucosylated IgG showed an average 16-fold antibody-mediated target cell depletion activity with average EC$_{50}$ values of 0.443 μg/ml and 0.00817 μg/ml which indicated a much higher efficacy compared to fucosylated IgG. It should be noted that the afucosylated IgG samples that had shown an increased FcγRIIIa-binding activity also induced a higher ADCC-response compared to the WT IgG.

TABLE 2

Summarized results of the ADCC-effector function of afucosylated (H1-3) and fucosylated (WT) IgG incubated with different antigen presenting target cells (BT-474, SK-BR-3).

| Sample name | BT-474 EC$_{50}$ [ng/mL] | BT-474 Ratio (WT/H) | SK-BR-3 EC$_{50}$ [ng/mL] | SK-BR-3 Ratio (WT/H) |
|---|---|---|---|---|
| WT | 6.03 | — | 1.31 | — |
| H1 | 0.454 | 13 | 0.0932 | 14 |
| H2 | 0.227 | 27 | 0.0602 | 22 |
| H3 | 0.647 | 9 | 0.0917 | 14 |

The calculated ratio EC$_{50}$ (fucosylated)/EC$_{50}$ (afucosylated) indicates the enhanced ADCC-effector function.

Figure 9:
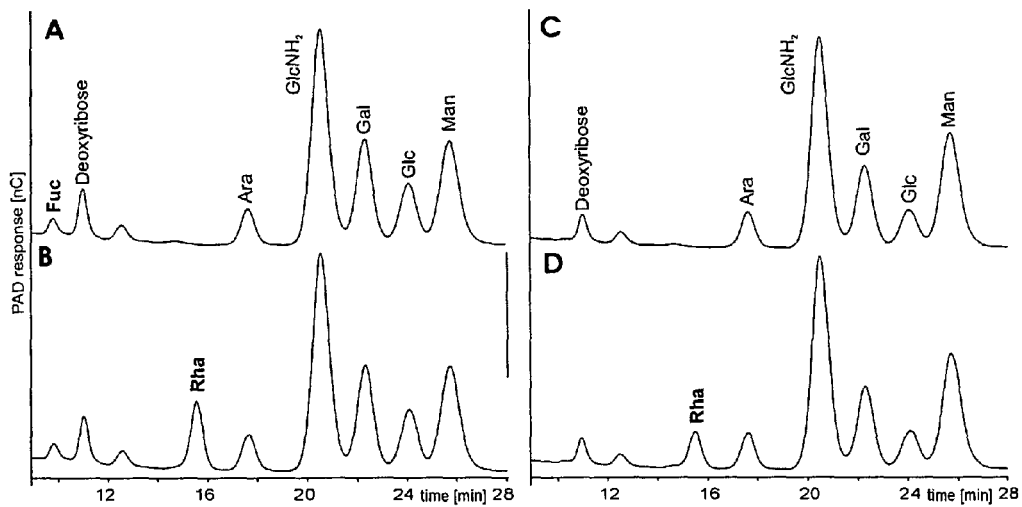
FIG. 9 shows a HPAEC-PAD profile of monosaccharides hydrolized from the cytosolic fraction of (A) unmodified CHO cells and (C) RMD-CHO clone H2. (B), (A) spiked with 10 pmol/μL-rhamnose and (D), (C) spiked with 10 pmol/μl L-rhamnose. As the monosaccharides were not re-N-acetylated after the TFA hydrolysis, GlcNAc was measured as GlcNH2. Under the selected conditions, the L-rhamnose peak elutes at a retention time of approximately 15.5 minutes. Note the absence of the fucose peak from the HPAEC-PAD chromatograms of the cell lysate from the modified clone H2.
Figure 10:
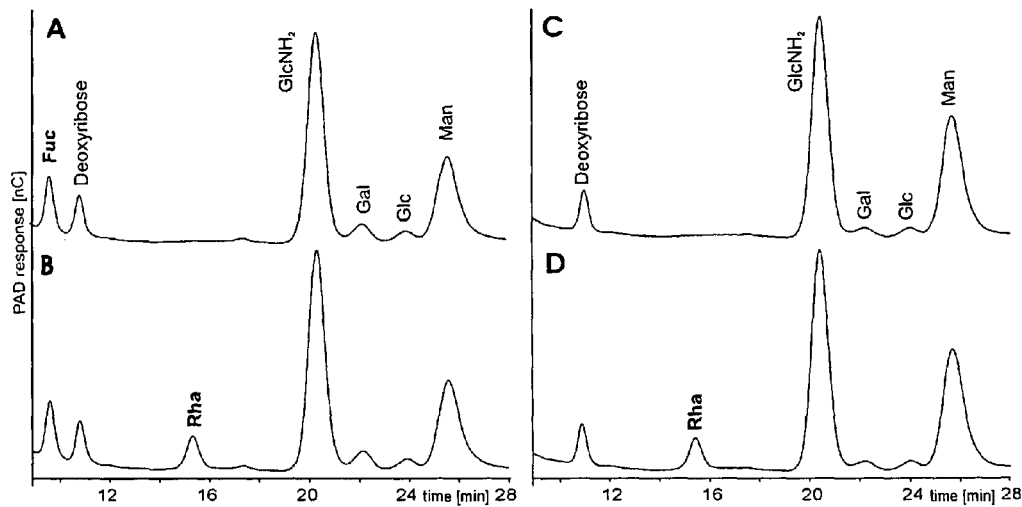
FIG. 10 shows a HPAEC-PAD profile of monosaccharides released from IgG N-glycans from (A), WT CHO and (C), the modified RMD-CHO clone H2, (B), (A) spiked with 10 pmol/μl L-rhamnose and (D), (C) spiked with 10 pmol/μl L-rhamnose. As the monosaccharides were not re-N-acetylated after the TFA hydrolysis, GlcNAc was measured as GlcNH$_2$. Under the selected conditions, the L-rhamnose peak elutes at a retention time of approximately 15.5 minutes. Note the absence of the fucose peak from the HPAEC-PAD chromatograms of the IgG N-glycan sample derived from RMD-CHO clone H2.

2.3.6 Monosaccharide Analysis—Absence of Detectable Amounts of D-Rhamnose in Cell Lysates as Well as in IgG N-Glycans Cell membranes, culture supernatants and cytosolic fractions were isolated from RMD-CHO cells. Monosaccharides were subsequently released and analyzed by HPAEC-PAD. As expected, fucose was present in CHO cells and not in RMD-CHO cells. A level of rhamnose exceeding the limit of detection (LOD) was not observed in the cytosolic fractions (FIG. 9). Based on the standard deviation of the y-intercept and slope of the calibration curve, the LOD were 1.2 pmol and 1.1 pmol per 10 μl sample injection volume for rhamnose and fucose, respectively. Similarly, N-glycans, released from purified antibodies produced using RMD-CHO cells, were hydrolyzed with TFA and the resulting monosaccharides were analyzed by HPAEC-PAD. The TFA-hydrolyzed N-glycans did not yield any rhamnose peak that exceeded the LOD (FIG. 10). To conclude, neither RMD-CHO cells nor the secreted antibodies contain detectable amounts of rhamnose.

2.4 Final Remarks

Figure 1:
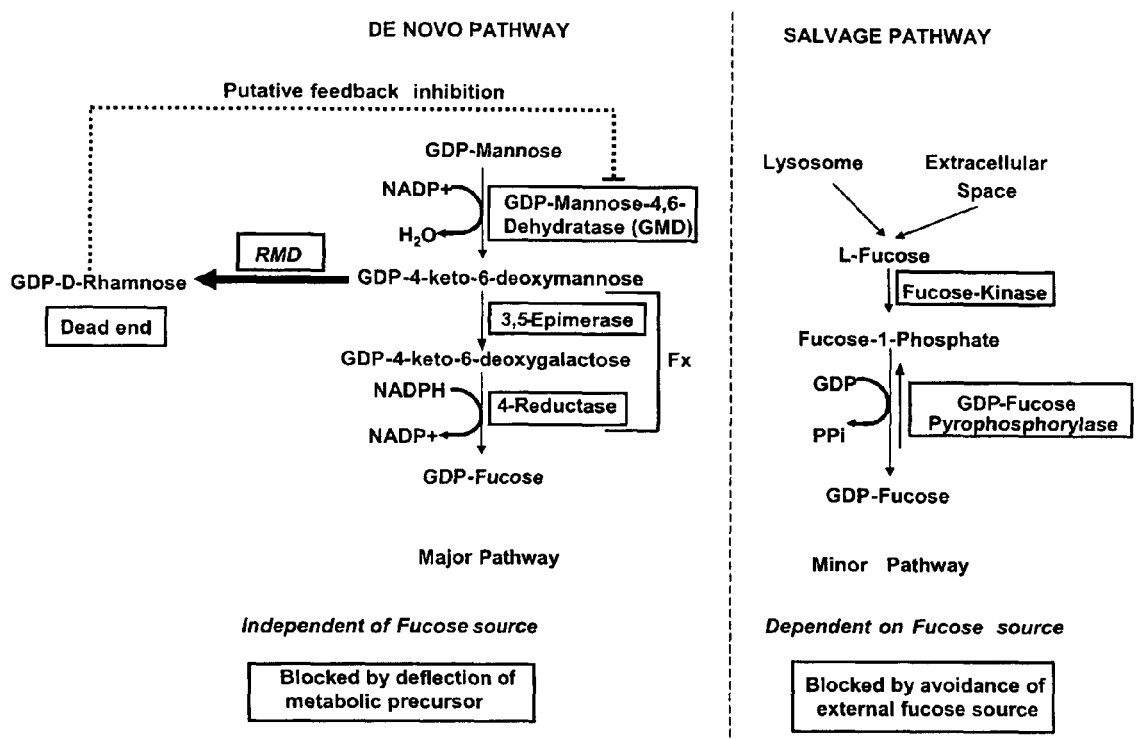
FIG. 1 shows an overview of the fucose salvage and de novo pathways in eukaryotic cells (e.g. vertrebrate cells). In the absence of fucose, cells are unable to synthesize GDP-fucose via the salvage pathway (see right hand panel). The de novo pathway can be blocked by enzymatic conversion of the intermediate GDP-4-keto-6-deoxymannose into a dead end product that typically does not occur in vertebrate cells (left hand panel). If the deflecting enzyme is RMD, for example, then the dead end product is GDP-D-rhamnose. GDP-deoxyhexoses such as GDP-D-rhamnose may exert a feedback inhibition on the GMD-enzyme thereby further blocking the fucose de novo pathway as well as the alternate GDP-rhamnose synthesis.

We evaluated a glycoengineering approach to achieve secretion of fucose-deficient mAbs from cell lines that were modified for continuous removal of a key metabolic intermediate from the cytosolic fucose de novo synthesis pathway (FIG. 1). Our data clearly show that a transgenic expression of a heterologous bacterial enzyme leads to the desired block in the synthesis of fucose on nascent glycoprotein N-glycans. The extent of fucose-depletion by this method also indicates that omission of fucose from the culture medium was sufficient to completely block the salvage pathway, which may otherwise have served as an alternate source of cytosolic GDP-fucose.

The key metabolic target in our approach was GDP-4-keto-6-deoxy-D-mannose, which is a common intermediate for the synthesis of several different GDP-monodeoxyhexoses including GDP-L-fucose, GDP-4-deoxy-D-talose, GDP-colitose, and GDP-D-perosamine, for example, in bacteria. Moreover, an active site Cys109Ser mutant of GDP-fucose synthase produces GDP-6-deoxy-D-altrose instead of GDP-fucose (Lau and Tanner, 2008).

The specific prokaryotic enzyme that we exemplarily selected for our approach was GDP-6-deoxy-D-lyxo-4-hexulose reductase (synonym with GDP-4-keto-6-deoxy-D-mannose reductase, abbreviated RMD) (Kneidinger et al., 2001; Maki et al., 2002). We demonstrated here that heterologous expression of the prokaryotic enzyme GDP-6-deoxy-D-lyxo-4-hexulose reductase (RMD) within the cytosol can efficiently deflect the fucose de novo pathway. Said enzyme utilizes NADH and NADPH as hydrogen donors and catalyzes the targeted reduction of the 4-keto group of the fucose pathway intermediate GDP-4-keto-6-deoxy-D-mannose to yield GDP-D-rhamnose. The conversion of GDP-4-keto-6- deoxy-D-mannose to GDP-D-rhamnose by RMD appears to proceed quantitatively, because no reverse reaction has been detected (Kneidinger et al., 2001).

Our data also show that GDP-rhamnose, a 6-deoxyhexose found only in glycoconjugates of certain bacteria but not in animals (Webb et al., 2004), is a dead-end product within the context of the vertebrate cytosol. Unmodified vertebrate cells lack rhamnosyltransferases (Webb et al., 2004) and membrane transporters so that the incorporation of GDP-D-rhamnose into nascent glycans is very unlikely within vertebrate cells. Our data could confirm this. They clearly show that artificial D-rhamnose was not incorporated into the secreted IgG or elsewhere in the cell (FIG. 9 and FIG. 10).

In addition to the lack of fucose on glucane structures, the IgGs secreted from the genetically engineered clones showed a higher level of high-mannose structures. This may arise from a feedback-inhibition of GMD by GDP-D-rhamnose. The lack of GMD-activity as an alternate metabolic sink for GDP-mannose may have contributed to an elevated pool of cytosolic GDP-D-mannose which in turn may have caused the elevation of high-mannose structures observed in products secreted from RMD-modified host cells (FIG. 4 and FIG. 5).

Our results for the FcγRIII-binding assay as well as for in vitro ADCC-assay also show that afucosylated IgGs have a significantly higher binding activity for FcγRIIIa and an enhanced ADCC-response. The observed $EC_{50}$ shift and fold-increase in target cell depletion activity (Table 2, FIG. 8) would have been even higher if the assay had been conducted in the presence of whole blood, serum or plasma. Interestingly, we observed that the afucosylated IgG sample H2 with the highest level of high-mannose structures, also showed the highest ADCC-activity, regardless of the target cell used in the assay (BT474 or SK-BR-3) (Table 2).

Taken together, this study demonstrates that overexpression of RMD in vertebrate host cells causes a depletion of an important key intermediate for the synthesis of cytosolic GDP-fucose, GDP-4-keto-6-deoxy-D-mannose. This approach allows generation of metabolically engineered cell lines but also offers a highly promising new strategy to convert existing antibody expressing cell clones into producer cells for fucose-depleted therapeutics. The ability to reliably engineer fucose deficiency in already existing cell lines may help to accelerate drug development for next generation monoclonal antibodies.

3. Abbreviations

ACN, Acetonitrile; CHO, Chinese Hamster Ovary; CV, coefficient of variation; dHex, deoxyhexose; $EC_{50}$, Half maximal effective concentration (i.e. the concentration of agonist that provokes a response halfway between the baseline and maximum response), Fuc, fucose; Gal, galactose; GalNAc, N-acetylgalactosamine; GlcNAc, N-acetylglucosamine; GMER, GDP-4-keto-6-deoxy-D-mannose-3,5-epimerase/4-reductase; HPLC, high-performance liquid chromatography; HPAEC-PAD, high-pH anion-exchange chromatography with pulsed amperometric detection; LOD Limit of Detection; mAb, monoclonal antibody; MALDI-TOF-MS matrix-assisted laser desorption ionization time-of-flight mass spectrometry; MEM, Modified Eagle's Medium; PBMCs, peripheral blood mononuclear cells; PBS, phosphate buffer saline; PNGase F, peptide-N4-(N-acetyl-β-glucosaminyl) asparagine amidase F; Rha, rhamnose; RMD, GDP-6-deoxy-D-lyxo-4-hexulose reductase; SDS, sodium dodecyl sulfate; TFA, Trifluoroacetic acid.

REFERENCES

Ceroni, A., Maass, K., Geyer, H., Geyer, R., Dell, A., Haslam, S. M. 2008. GlycoWorkbench: A Tool for the Computer-Assisted Annotation of Mass Spectra of Glycans, Journal of Proteome Research, 7 (4), 1650-1659.

Chen, P, Baker A G, Novotny M V. 1997. The use of osazones as matrices for the matrix-assisted laser desorption/ionization mass spectrometry of carbohydrates. Anal Biochem. 244(1):144-51.

Horton, D 2004 Advances in Carbohydrate Chemistry and Biochemistry. D. Horton, Editor, Elsevier Academic Press, Amsterdam and San Diego, Vol. 59, p. 11.

ICH Q2(R1): ICH Harmonized Tripartite Guideline: Validation of Analytical Procedures: Text and Methodology Q2(R1) Current Step 4 version, Parent Guideline dated 27 Oct. 1994.

Kneidinger B, Graninger M, Adam G, Puchberger M, Kosma P, Zayni S, Messner P. 2001. Identification of two GDP-6-deoxy-D-lyxo-4-hexulose reductases synthesizing GDP-D-rhamnose in *Aneurinibacillus thermoaerophilus* L420-91T. J Biol Chem. February 23; 276(8):5577-83.

Lasfargues E Y, Coutinho W G and Redfield E S. 1978. Isolation of two human tumor epithelial cell lines from solid breast carcinomas. J Natl Cancer Inst.; 61(4):967-78.

Lau S. T. B., Tanner, M. E. 2008. Mechanism and Active Site Residues of GDP-Fucose Synthase, Journal of the American Chemical Society, vol. 130, no 51, pp. 17593-17602

Mäki M, Järvinen N, Räbinä J, Roos C, Maaheimo H, Renkonen R; Pirkko; Mattila. 2002. Functional expression of *Pseudomonas aeruginosa* GDP-4-keto-6-deoxy-D-mannose reductase which synthesizes GDP-rhamnose. Eur J Biochem. January; 269(2):593-601.

Niwa R, Shoji-Hosaka E, Sakurada M, Shinkawa T, Uchida K, Nakamura K, Matsushima K, Ueda R, Hanai N, Shitara K. 2004. Defucosylated anti-CC chemokine receptor 4 IgG1 with enhanced antibody-dependent cellular cytotoxicity shows potent therapeutic activity to T cell leukemia and lymphoma. Cancer Res, 64:2127-2133.

Niwa R, Hatanaka S, Shoji-Hosaka E, Sakurada M, Kobayashi Y, Uehara A, Yokoi H, Nakamura K, Shitara K. 2004. Enhancement of the antibody-dependent cellular cytotoxicity of low-fucose IgG1 is independent of FcgammaRIIIa functional polymorphism. Clin Cancer Res, 10:6248-6255.

Shields R L, Lai J, Keck R, O'Connell L Y, Hong K, Meng Y G, Weikert S H, Presta L G. 2002. Lack of fucose on human IgG1 N-linked oligosaccharide improves binding to human FcgammaRIII and antibody-dependent cellular toxicity. J Biol Chem, 277:26733-26740.

Sondermann, P., Huber, R., Oosthuizen, V., and Jacob, U. 2000. The 3.2-A crystal structure of the human IgG1 Fc fragment-Fc gammaRIII complex. Nature 406, 267-273.

Urlaub G, Käs E, Carothers A M, Chasin L A. Deletion of the diploid dihydrofolate reductase locus from cultured mammalian cells. Cell. 1983 June; 33(2):405-12.

Urlaub G, Mitchell P J, Kas E, Chasin L A, Funanage V L, Myoda T T, Hamlin J. 1986. Effect of gamma rays at the dihydrofolate reductase locus: Deletions and inversions. Somatic Cell Mol Genet, 12:555-556.

Wada, Y.; Azadi, P.; Costello, C. E.; Dell, A.; Dwek, R. A.; Geyer, H.; Geyer, R.; Kakehi, K.; Karlsson, N. G.; Kato, K.; Kawasaki, N.; Khoo, K. H.; Kim, S.; Kondo, A.; Lattova, E.; Mechref, Y.; Miyoshi, E.; Nakamura, K.; Narimatsu, H.; Novotny, M. V.; Packer, N. H.; Perreault, H.; Peter-Katalinic, J.; Pohlentz, G.; Reinhold, V. N.; Rudd, P. M.; Suzuki, A.; Taniguchi, N. 2007. Comparison of the methods for profiling glycoprotein glycans—HUPO Human Disease Glycomics/Proteome Initiative multi-institutional study. Glycobiology; 17(4):411-22.

Webb N A, Mulichak A M, Lam J S, Rocchetta H L, Garavito R M. 2004. Crystal structure of a tetrameric GDP-D-mannose 4,6-dehydratase from a bacterial GDP-D-rhamnose biosynthetic pathway. Protein Sci. February; 13(2):529-39.

Zabrecky J R, Lam T, McKenzie S J and Carney W. 1991. The extracellular domain of p185/neu is released from the surface of human breast carcinoma cells, SK-BR-3. J Biol Chem.; 266(3):1716-20.

---

The invention claimed is:

1. A recombinant vertebrate cell for producing a protein molecule, lacking fucose or with a reduced amount of fucose on its glycomoieties, said cell comprising a polynucleotide that encodes
    at least one enzyme which uses GDP-6-deoxy-D-lyxo-4-hexylose as a substrate, wherein the enzyme does not catalyze the reaction which converts GDP-6-deoxy-D-lyxo-4-hexylose into GDP-L-fucose.

2. The vertebrate cell of claim 1, wherein the enzyme which uses GDP-6-deoxy-D-lyxo-4-hexylose as a substrate is selected from the group consisting of GDP-6-deoxy-D-lyxo-4-hexylose reductase (RMD), GDP-perosamine synthetase (Per), GDP-6-deoxy-D-talose synthetase (GTS), GDP-Fucose synthetase Cys109Ser-(GTS-Cys109Ser) mutant, GDP-4-keto-6-deoxymannose-3-dehydratase (ColD), and GDP-4-keto-6-deoxymannose-3-dehydratase (ColD) in combination with GDP-L-colitose synthase (ColC).

3. The vertebrate cell of claim 2, wherein the GDP-6-deoxy-D-lyxo-4-hexylose reductase (RMD) is from *Pseudornonas aeruginosa* (SE) ID NO: 1).

4. The vertebrate cell of claim 1 further comprising GDP-D-rhamnose, GDP-D-perosamine, GDP-deoxy-D-talose, GDP-6-deoxy-D-altrose, GDP-4-keto-3,6-dideoxy-D-mannose, and/or GDP-L-colitose.

5. The vertebrate cell of claim 1, wherein the polynucleotide is transiently present or stably maintained in said cell.

6. The vertebrate cell of claim 1, wherein the cell comprises said protein molecule which is capable of being a substrate for a fucosyltransferase.

7. The vertebrate cell of claim 6, wherein the molecule is a substrate protein.

8. The vertebrate cell of claim 1, wherein the protein molecule is an endogenous or an exogenous protein.

9. The vertebrate cell of claim 1, wherein the protein molecule is an antibody, an antibody fragment, a fusion protein, a virus protein, a virus protein fragment, an antigen, or a hormone.

10. The vertebrate cell of claim 1, wherein the vertebrate cell is a mammalian, a fish, an amphibian, a reptilian cell or an avian cell.

11. The vertebrate cell of claim 10, wherein
   i) the mammalian cell is a human, hamster, canine or monkey cell;
   ii) the fish cell is a lectalurus punctatus (channel catfish) ovary (CCO);
   iii) the amphibian cell is a *Xenopus laevis* kidney cell;
   iv) the reptilian cell is a *Iguana iguana* heart cells (IgH-2); or
   v) the avian cell is an avian retina cell, or an avian somite cell.

12. The vertebrate cell according to claim 1 which further comprises at least one glycosyltransferase for GDP-D-rhamnose, GDP-D-perosamine, GDP-deoxy-D-talose, GDP-6-deoxy-D-altrose, GDP-4-keto-3,6-dideoxy-D-mannose, or GDP-L-colitose.

13. A method for producing a protein rnolecle, lacking fucose or with a reduced amount of fucose on its glyconioieties comprising the steps of:
   i) providing a vertebrate cell according to claim 1,
   ii) isolating the protein molecule which is capable of being a substrate for a fucosyltransferase from the cell in i).

14. A protein molecule lacking fucose or with a reduced amount of fucose on its glycomoieties obtainable by the method of claim 13.

15. A composition of protein molecules according to claim 14.

16. A protein molecule which comprises glycomoieties containing D-rhamnose, D-perosamine, deoxy-D-talose, 6-deoxy-D-altrose, 4-keto-3,6-dideoxy-D-mannose, and/or L-colitose, wherein said protein molecule is obtainable by the method of claim 13.

17. An expression unit comprising one or more vertebrate expression control sequences operably linked to a polynucleotide comprising a nucleic acid sequence encoding an enzyme which uses GDP-6-deoxy-D-lyxo-4-hexylose as a substrate, wherein the enzyme does not catalyze the reaction which converts GDP-6-deoxy-D-lyxo-4-hexylose into GDP-L-fucose.

18. The expression unit of claim 17, wherein the enzyme which uses GDP-6-deoxy-D-lyxo-4-hexylose as a substrate is selected from the group consisting of GDP-6-deoxy-D-lyxo-4-hexylose reductase (RMD), GDP-perosamine synthetase (Per), GDP-6-deoxy-D-talose synthetase (GTS), GDP-Fucose synthetase Cys109Ser-(GFS-Cys109Ser) mutant, GDP-4-keto-6-deox:/mannose-3-dehydratase (ColD), and GDP-4-keto-6-dcoxymannose-3-dehydratase (ColD) in combination with GDP-L-colitosc synthase (ColC).

19. A recombinant eukaryotic cell for producing a protein, lacking fucose or with a reduced amount of fucose on its glycomoieties comprising:
   i) a first polynucleotide comprising a nucleic acid sequence encoding an enzyme which uses GDP-6-deoxy-D-lyxo-4-hexylose as a substrate, and
   ii) a second polynucleotide comprising a nucleic acid sequence encoding a protein, wherein the enzyme does not catalyze the reaction which converts GDP-6-deoxy-D-lyxo-4-hexylose into GDP-L-fucose.

20. The eukaryotic cell of claim 19, wherein the enzyme which uses GDP-6-deoxy-D-lyxo-4-hexylose as a substrate is selected from the group consisting of GDP-6-deoxy-D-lyxo-4-hexylose reductase (RMD), GDP-perosamine synthetase (Per), GDP-6-deoxy-D-talose synthetase (GTS), GDP-Fucose synthetase Cys109Ser-(GFS-Cys109Ser) mutant, GDP-4-keto-6-deoxymannose-3-dehydratase (ColD), and GDP-4-keto-6-deoxymannose-3-dehydratase (ColD) in combination with GDP-L-colitose synthase (ColC).

21. The eukaryotic cell of claim 19, wherein the protein is antibody, an antibody fragment, a fusion protein comprising the Fc region of an antibody, a virus protein, a virus protein fragment, an antigen, or a hormone.

22. A method for producing a protein lacking fucose or with a reduced amount of fucose on its glycomoieties comprising the steps of:
   i) providing an eukaryotic cell according to claim 19,
   ii) expressing the enzyme encoded by the first polynucleotide and the protein encoded by the second polynucleotide in said cell, and
   iii) isolating the protein from said cell.

23. A protein lacking fucose or with a reduced amount of fucose on its glycomoieties obtainable by the method of claim 22.

24. The vertebrate cell of claim 8, wherein the protein molecule is an antibody, an antibody fragment, a fusion protein, a virus protein, a virus protein fragment, an antigen, or a hormone.

* * * * *

UNITED STATES PATENT AND TRADEMARK OFFICE
CERTIFICATE OF CORRECTION

| | |
|---|---|
| PATENT NO. | : 8,642,292 B2 |
| APPLICATION NO. | : 13/496997 |
| DATED | : February 4, 2014 |
| INVENTOR(S) | : Volker Sandig et al. |

It is certified that error appears in the above-identified patent and that said Letters Patent is hereby corrected as shown below:

Delete Title Page, and replace with new Title Page. (Attached)

In the Claims

Claim 1, Column 53, Line 58, delete "hexylose" and insert --hexulose--.

Claim 1, Column 53, Line 60, delete "hexylose" and insert --hexulose--.

Claim 2, Column 53, Line 62, delete "hexylose" and insert --hexulose--.

Claim 2, Column 53, Line 64, delete "hexylose" and insert --hexulose--.

Claim 2, Column 53, Line 66, delete "(GTS-Cys109Ser)" and insert --(GFS-Cys109Ser)--.

Claim 3, Column 54, Line 55, delete "hexylose" and insert --hexulose--.

Claim 3, Column 54, Lines 55 and 56, delete "Pseudornonas aeruginosa (SE) ID NO: 1)" and insert --Pseudomonas aeruginosa (SEQ ID NO: 1)--.

Claim 7, Column 54, Lines 66 and 67, delete entire claim.

Claim 11, Column 55, Line 13, delete "lectalurus" and insert --Ictalurus--.

Claim 11, Column 55, Line 14, after "(CCO)" insert --cell--.

Claim 11, Column 55, Line 16, after "heart" delete "cells" and insert --cell--.

Claim 13, Column 55, Line 25, delete "rnolecle" and insert --molecule--.

Signed and Sealed this
Second Day of December, 2014

Michelle K. Lee
*Deputy Director of the United States Patent and Trademark Office*

Claim 13, Column 55, Line 26, delete "glyconioieties" and insert --glycomoieties--.

Claim 17, Column 55, Line 44, delete "hexylose" and insert --hexulose--.

Claim 17, Column 55, Line 46, delete "hexylose" and insert --hexulose--.

Claim 18, Column 55, Line 49, delete "hexylose" and insert --hexulose--.

Claim 18, Column 56, Line 1, delete "hexylose" and insert --hexulose--.

Claim 18, Column 56, Line 4, delete "GDP-4-keto-6-deox:/mannose-3-dehydratase" and insert --GDP-4-keto-6-deoxymannose-3-dehydratase--.

Claim 18, Column 56, Line 5, delete "GDP-4-keto-6-dcoxymannose-3-dehydratase" and insert --GDP-4-keto-6-deoxymannose-3-dehydratase--.

Claim 19, Column 56, Line 14, delete "hexylose" and insert --hexulose--.

Claim 19, Column 56, Line 18, delete "hexylose" and insert --hexulose--.

Claim 20, Column 56, Line 20, delete "hexylose" and insert --hexulose--.

Claim 20, Column 56, Line 22, delete "hexylose" and insert --hexulose--.

Claim 21, Column 56, Line 30, before "antibody" insert --an--.

United States Patent
Sandig et al.

(10) Patent No.: US 8,642,292 B2
(45) Date of Patent: Feb. 4, 2014

(54) PROCESS FOR PRODUCING MOLECULES CONTAINING SPECIALIZED GLYCAN STRUCTURES

(75) Inventors: Volker Sandig, Berlin (DE); Hans Henning von Horsten, Berlin (DE); Christiane Ogorek, Berlin (DE)

(73) Assignee: Probiogen AG, Berlin (DE)

( * ) Notice: Subject to any disclaimer, the term of this patent is extended or adjusted under 35 U.S.C. 154(b) by 0 days.

(21) Appl. No.: 13/496,997

(22) PCT Filed: Sep. 21, 2010

(86) PCT No.: PCT/EP2010/005772
§ 371 (c)(1),
(2), (4) Date: Apr. 26, 2012

(87) PCT Pub. No.: WO2011/035884
PCT Pub. Date: Mar. 31, 2011

(65) Prior Publication Data
US 2012/0214975 A1    Aug. 23, 2012

Related U.S. Application Data

(60) Provisional application No. 61/244,624, filed on Sep. 22, 2009.

(51) Int. Cl.
*C12P 21/06*     (2006.01)
*C12N 15/00*    (2006.01)
*C12N 1/20*     (2006.01)
*C07K 1/00*     (2006.01)

(52) U.S. Cl.
USPC ............ 435/69.1; 435/320.1; 435/252.3; 530/350

(58) Field of Classification Search
USPC ............ 435/69.1, 320.1, 252.3; 530/350
See application file for complete search history.

(56) References Cited

FOREIGN PATENT DOCUMENTS

| EP | 1 331 266 A1 | 7/2003 |
| EP | 1 642 971 A1 | 4/2006 |
| WO | WO 2006/133148 A2 | 12/2006 |

OTHER PUBLICATIONS

Satoh Mitsuo et al: "Non-fucosylated therapeutic antibodies as next-generation therapeutic antibodies.", Expert Opinion on Biological Therapy, Ashley, London, GB, vol. 6, No. 11, Nov. 1, 2006, pp. 1161-1173, ISSN: 1471-2598, DOI: DOI:10.1517/14712598.6.11.1161.

Katsuhiro Mori et al: "Non-fucosylated therapeutic antibodies: the next generation of therapeutic antibodies", Cytotechnology, Kluwer Academic Publishers, DO, vol. 55, No. 2-3, Oct. 31, 2007, pp. 109-114, ISSN: 1573-0778, DOI: DOI: 10.1007/S10616-007-9103-2.

Imai-Nishiya Harue et al: "Double knockdown of alpha 1,6-fucosyltransferase (FUT8) and GDP-mannose 4,6-dehydratase (GMD) in antibody-producing cells: a new strategy for generating fully non-fucosylated therapeutic antibodies with enhanced ADC", BMC Biotechnology, vol. 7, Nov. 2007, ISSN: 1472-6750.

Kanda et al: Establishment of a GDP-mannose 4,6-dehydratase (GMD) knockout host cell line: A new strategy for generating completely non-fucosylated recombinant therapeutics, Journal of Biotechnology. Elsevier Science Publishers, Amsterdam, NL, vol. 130, No. 3, Jun. 19, 2007, pp. 300-310, ISSN: 0168-1656, DOI: DOI:10.1016/J.JBIOTEC.2007.04.025.

Omasa T, et al. "Decrease in antithrombin III fucosylation by expressing GDP-fucose transportersiRNA in Chinese hamster ovary cells", Journal of Bioscience and Bioengineering, Elsevier, Amsterdam, NL, vol. 106, No. 2, Aug. 1, 2008, pp. 168-173, ISSN: 1389-1723; DOI: DOI:10.1263/JBB.106.168.

Shields, R. L. et al: "Lack of Fucose on Human IgG1 N-Linked Oligosaccharide Improves Binding to Human FcγRIII and Antibody-Dependent Cellular Toxicity", Journal of Biological Chemistry< American Society for Biochemistry and Molecular Biology<INC>, US, vol. 277, No. 30, Jul. 26, 2002, pp. 26733-26740, ISSN: 0021-9258, DOI: DOI:10.1074/JBC.M202069200.

Ohyama C, et al., "Molecular Cloning and Expression of GDP-D-mannose-4,6-dehydratase, a Key Enzyme for Fucose Metabolism Defective in Lec13 Cells", Journal of Biological Chemistry< American Society for Biochemistry and Molecular Biology, Inc>, US, vol. 273, No. 23, Jun. 5, 1998, pp. 14582-14587, ISSN: 0021-9258, DOI: DOI:10.1074/JBC.273.23.14582.

Maki Minna et al>: "Functional Expression of *Pseudomonas aeruginosa* GDP-4-keto-6-deoxy-D-mannose reductase which synthesizes BDP-rhamnose", European Journal of Biochemistry, vol. 269, No. 2, Jan. 2002, pp. 593-601, ISSN: 0014-2956.

Rocchetta Heather L. et al: "Synthesis of the A-band polysaccharide sugar D-rhamnose requires Rmd and WbpW: Identification of Multiple AlgA Homologues, WbpW and ORF488, in *Pseudomonas aeruginosa*", Molecular Microbiology, vol. 29, No. 6, Sep. 1998, pp. 1419-1434, ISSN: 0950-382X.

Kneidinger Bernd, et al.: "Identification of Two GDP-6-deoxy-D-lyxo-4-hexulose reductases Synthesizing GDP-D-rhamnose in *Aneurinibacillus thermoaerophilus* L420-91T", Journal of Biological Chemistry, vol. 276, No. 8, Feb. 23, 2001, pp. 5577-5583, ISSN: 0021-9258.

Yamane-Ohnuki, N. and Satoh, M. et al., Production of Therapeutic Antibodies with Controlled Fucosylation. mAbs, May-Jun. 2009, vol. 1, pp. 230-236, claims 1-15, 21-27.

Primary Examiner — Maryam Monshipouri
(74) Attorney, Agent, or Firm — Faegre Baker Daniels LLP

(57) ABSTRACT

The present invention relates to cells for producing a molecule lacking fucose, having a reduced amount of fucose, or having other atypical sugars on its glycomoieties. It also relates to methods for producing a molecule lacking fucose, having a reduced amount of fucose, or having other atypical sugars on its glycomoieties using said cells and to molecules obtainable by said methods. The present invention further relates to molecules having an artificial glycosylation pattern.

23 Claims, 9 Drawing Sheet